United States Patent
Yumoto et al.

(10) Patent No.: US 6,902,687 B2
(45) Date of Patent: Jun. 7, 2005

(54) OPTICALLY ACTIVE ISOSORBIDE DERIVATIVE AND OPTICALLY ACTIVE ISOMANNIDE DERIVATIVE, PRODUCTION METHODS THEREOF, PHOTO-REACTIVE CHIRAL AGENT, LIQUID CRYSTAL COMPOSITION, LIQUID CRYSTAL COLOR FILTER, OPTICAL FILM AND RECORDING MEDIUM, METHOD FOR CHANGING HELICAL STRUCTURE OF LIQUID CRYSTAL AND METHOD FOR FIXING HELICAL STRUCTURE OF LIQUID CRYSTAL

(75) Inventors: Masatoshi Yumoto, Shizuoka-ken (JP); Mitsuyoshi Ichihashi, Kanagawa (JP); Keiichiro Hayashi, Shizuoka-ken (JP); Ryuichi Kuroiwa, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 223 days.

(21) Appl. No.: 10/418,316

(22) Filed: Apr. 18, 2003

(65) Prior Publication Data

US 2004/0019228 A1 Jan. 29, 2004

(30) Foreign Application Priority Data

Apr. 18, 2002 (JP) .................................... 2002-116295
Apr. 22, 2002 (JP) .................................... 2002-119138

(51) Int. Cl.⁷ .................. C07D 493/04; C09K 19/52
(52) U.S. Cl. ................. 252/299.61; 349/2; 349/24; 349/106; 428/1.1; 430/7; 430/19; 549/464
(58) Field of Search .................. 252/299.61; 349/2, 349/24, 106; 428/1.1; 430/7, 19; 549/464

(56) References Cited

FOREIGN PATENT DOCUMENTS

| GB | 2 314 839 A | 1/1998 |
|---|---|---|
| JP | 2002-080478 A | 3/2002 |
| JP | 2002-080851 A | 3/2002 |
| JP | 2002-179681 A | 6/2002 |
| JP | 2002-179682 A | 6/2002 |
| JP | 2002-338575 A | 11/2002 |
| WO | WO 00/34808 A1 | 6/2000 |

Primary Examiner—Bernard Dentz
(74) Attorney, Agent, or Firm—Sughrue Mion, PLLC

(57) ABSTRACT

The invention relates to an optically active isosorbide derivative represented by general formula (I) and an optically active isomannide derivative represented by general formula (V), General formula (I)

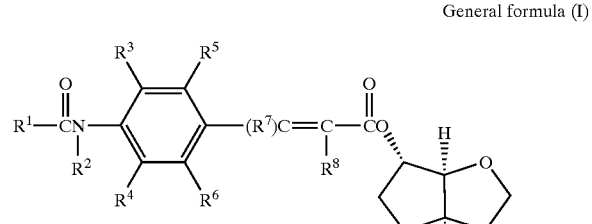

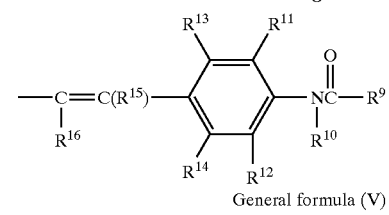

General formula (V)

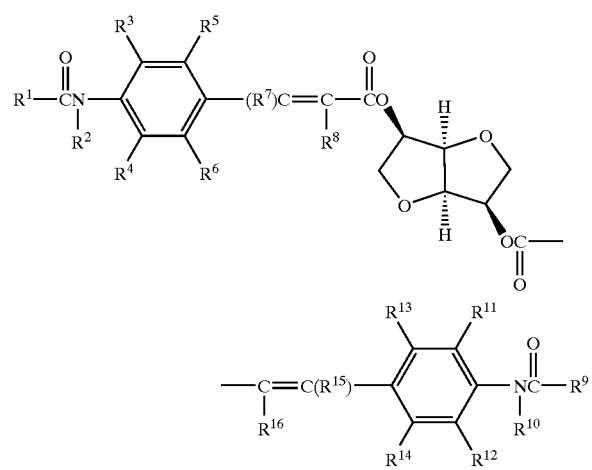

wherein $R^1$ and $R^9$ each independently represent an alkyl group, an alkenyl group, an aryl group, a heterocyclic group, an alkoxy group, an aryloxy group or —$NR^{17}R^{18}$, wherein $R^{17}$ and $R^{18}$ each independently represent a hydrogen atom, an alkyl group or an aryl group; $R^2$ and $R^{10}$ each independently represent a hydrogen atom, an alkyl group or an aryl group; $R^3$ to $R^6$ and $R^{11}$ to $R^{14}$ each independently represent a hydrogen atom, a halogen atom, an alkyl group or an alkoxy group; $R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

22 Claims, 3 Drawing Sheets

OPTICALLY ACTIVE ISOSORBIDE DERIVATIVE AND OPTICALLY ACTIVE ISOMANNIDE DERIVATIVE, PRODUCTION METHODS THEREOF, PHOTO-REACTIVE CHIRAL AGENT, LIQUID CRYSTAL COMPOSITION, LIQUID CRYSTAL COLOR FILTER, OPTICAL FILM AND RECORDING MEDIUM, METHOD FOR CHANGING HELICAL STRUCTURE OF LIQUID CRYSTAL AND METHOD FOR FIXING HELICAL STRUCTURE OF LIQUID CRYSTAL

BACKGROUND OF THE INVENTION

1. Field of the Invention

The present invention relates to an optically active isosorbide derivative and an optically active isomannide derivative which each have a photosensitive property, respective production methods thereof, a photo-reactive chiral agent which causes a change in a liquid crystal structure, a liquid crystal composition comprising the chiral agent, a liquid crystal color filter, an optical film and recording medium and a method for changing or fixing the helical structure of the liquid crystal.

2. Description of the Related Art

In recent years, a liquid crystal material has attracted people's attention; for example, a cholesteric liquid crystal compound which has a helical structure and exhibits a variety of selectively reflected colors caused by a twisting power (twisting angle) based on the helical structure is excellent in a selective reflection property or color purity of selectively reflected light, thereby being widely used in an optical film, a liquid crystal color filter, a recording medium and the like.

A present situation thereof will be explained below taking, for example, a color filter.

The color filter for use in, for example, a color liquid crystal display is ordinarily constituted by respective pixels of red (R), green (G) and blue (B), and a black matrix formed in a space between any two pixels for improving a display contrast.

As for such color filters, a color filter in which a pigment is dispersed in a resin or the resin is dyed with a coloring agent is prevailing. Further, as for production methods thereof, a production method in which a colored resist layer is formed by applying a colored resin solution on a glass substrate by spin coating or the like and, then, patterning is performed on the thus-formed colored resist layer by a photolithographic technique to form a color filter pixel or another production method in which a colored pixel is directly printed on the substrate has ordinarily been adopted.

However, for example, in the production method by the printing technique, there has been a drawback that resolution of the pixel is low and such low resolution makes it difficult to respond to formation of a high-definition image pattern, while in the production method by such spin coating technique, there has been a drawback that waste of a material is large and also large coating unevenness is generated when the substrate having a large area is coated. Further, according to a production method by an electrodeposition technique, there has been a drawback that, although the color filter in which the resolution is comparatively high and unevenness of a colored layer is small can be obtained, production steps are complicated and also solution control is difficult.

Under these circumstances, as for the production methods of the color filter, a production method in which the waste of the material is small and a high-quality color filter can be produced in an efficient and convenient manner is required.

On the other hand, as for properties of the color filter, high transmittance and high color purity are required. In recent years, various improvements have been attempted for responding to such requirements, for example, by optimizing a type of the coloring agent or a resin dyed with the coloring agent in a method using a coloring agent and by employing a finely dispersed pigment in a method using a pigment. However, requirements for transmittance and color purity of the color filter in a recent liquid crystal display (LCD) panel are extremely high and, particularly in the color filter for use in a reflection type LCD, it is difficult to simultaneously satisfy white representation of paper white, contrast and color reproducibility and, further, since the color filter which is produced by dying the resin by the coloring agent or dispersing the pigment therein by a conventional production method is of light-absorption type, an improvement of color purity by further enhancing transmittance has nearly reached the limit.

Against such situation as described above, the color filter of a polarization utilization type comprising a cholesteric liquid crystal as a main component has attracted people's attention. This color filter of the polarization utilization type performs an image display by reflecting a given quantity of light and transmitting the remaining quantity of light, thereby having inherently high utilization efficiency of light and also remarkable properties in the transmittance and color purity compared with the color filter of the light-absorption type. On the other hand, as for production methods, from the standpoint of capability of obtaining uniform thickness, a method of forming a film on a substrate by utilizing the spin coating technique or the like has ordinarily been adopted; however, since the waste of the material was large, this method was disadvantageous from the standpoint of cost.

For the purpose of solving the above-described problems, allowing the uniformity of the color purity or the like of the color filter film to be secured and realizing a reduction of a number of production steps, a method using a photo-reactive chiral compound is effective. This method utilizes a theory that, when light having a wavelength reactive to the photo-reactive chiral compound is patternwise irradiated on a liquid crystal composition containing the photo-reactive chiral compound, a reaction advances in the chiral compound in accordance with an intensity of irradiation energy to change a helical pitch (helical twisting angle) of the crystal compound whereupon, only by patternwise exposure having different light quantities, a selectively reflected color is formed per pixel. In other words, this method has a merit in frequency of patterning at the time of forming the color filter such that it can be completed by performing only one-time mask exposure using a mask having different transmission light quantities.

Therefore, after the patterning is performed by irradiating light imagewise, a film which functions as the color filter can be formed by fixing the cholesteric crystal compound which has been subjected to patterning. This technique can be utilized also for an optical film, image recording and the like.

Particularly, in a case in which the color filter is formed by one-time mask exposure or other appropriate cases, it is desired that three primary colors, that is, B (blue), G (green) and R (red), can be formed with favorable color purity by one-time exposure. However, when a helical twisting change ratio is small, sufficient color purity can not be obtained. Therefore, in view of allowing three primary colors of high color purity to be displayed by one-time exposure, as a photo-reactive chiral compound on a practical point of view, it is necessary to use a chiral compound (chiral agent) having a large helical twisting change ratio which can substantially change the twisting power of the helical structure of the crystal compound. Namely, by using the chiral compound having a large helical twisting change ratio, a range of hues which is selectively reflected in accordance with a light quantity change can be expanded.

As examples of such chiral compounds, the present inventor disclose a photo-reactive chiral agent, having a isosorbide skeleton which has been esterified by a cinnamic acid derivative, described in Japanese Patent Application Laid-Open (JP-A) Nos. 2002-80851, 2002-179682, 2002-179681 and 2002-338575. Further, a photo-reactive chiral agent of benzylidene menthone type is disclosed in WO 00/34808.

On the other hand, a light source for use in the mask exposure is ordinarily a mercury lamp of super high pressure type having a emission line at 365 nm whereupon it is desirable that, for the purpose of allowing sensitivity at the time of the mask exposure to be high, that is, a reaction of the chiral compound to be faster, a molar absorption coefficient of the chiral agent is large in this wavelength region.

However, the chiral agent disclosed above had a drawback that, since the molar absorption coefficient thereof at 365 nm is small, the sensitivity at the time of the mask exposure is low, or a cis form to be generated by performing photo-isomerization is lack in thermal stability.

Further, although the present inventor also discloses a photo-reactive chiral agent having an isomannide skeleton which has been esterified by a cinnamic acid derivative in JP-A No. 2002-80478 as a chiral agent, the chiral agent also had a drawback that the molar absorption coefficient at 365 nm was small and the sensitivity at the time of the mask exposure was low.

As described above, it is a present situation that a photo-reactive chiral agent which is imparted with a photo-reactive property capable of changing an orientation structure such as a helical pitch (helical twisting power, helical twisting angle) of the liquid crystal in accordance with an irradiated light quantity and, for example, in case of a cholesteric liquid crystal phase comprising a nematic liquid crystal compound, and can substantially change the helical pitch (helical twisting power) thereof such that it has a wide range of wavelength capable of performing selective reflection, thereby allowing a variety of selective reflection to be exhibited and, particularly, allowing 3 primary colors (B, G, R) to be displayed in high color purity has not been provided.

SUMMARY OF THE INVENTION

The present invention has an object to solve these conventional problems and to attain an object described below.

Namely, a first object of the invention is to provide a novel optically active compound having a photosensitive property which is capable of changing a structure thereof by being isomerized by light and, further, excellent in thermal stability of a cis-form to be generated after such photo-isomerization is performed.

A second object of the invention is to provide a photo-reactive chiral agent which can control an orientation structure of a liquid crystalline compound, and has a large change ratio of a helical pitch (helical twisting power) (hereinafter also referred to as "helical twisting change ratio") of liquid crystal by light and, for example, in a case of a cholesteric liquid crystal phase, can perform a wide selective reflection of colors comprising three primary colors (B, G, R) and can display three primary colors in high color purity.

A third object of the invention is to provide a liquid crystal composition capable of changing a helical pitch (helical twisting power) of liquid crystal by light, and comprising a photo-reactive chiral agent which has a large helical twisting change ratio thereof and can change optical properties by substantially controlling an orientation state of a liquid crystal molecule by light in a three-dimensional manner, wherein, for example, in a case of a cholesteric liquid crystal, a wide range of selectively reflected colors comprising three primary colors are exhibited by light irradiation and the three primary colors excellent in color purity can be displayed.

A fourth object of the invention is to provide a method capable of substantially changing a helical pitch (helical twisting power) of liquid crystal by irradiating light on a liquid crystal composition comprising a photo-reactive chiral agent having a large helical twisting change ratio and capable of changing a helical structure of liquid crystal.

A fifth object of the invention is to provide a method comprising the steps of:

exposing imagewise a liquid crystal composition containing a photo-reactive chiral agent having a large helical twisting change ratio;

allowing the resultant patterned helical pitch to be fixed such that it is maintained without being damaged; and particularly in a case in which the liquid crystal phase is a cholesteric liquid crystal phase, fixing a helical structure of liquid crystal in a desired selectively reflected color to obtain a hue of high color purity.

Further, a sixth object of the invention is to provide a liquid crystal color filter of high color purity comprising a photo-reactive chiral agent which can substantially change a helical pitch (helical twisting power) of liquid crystal by light irradiation.

A seventh object of the invention is to provide an optical film of non-light absorption type comprising a photo-reactive chiral agent which can substantially change a helical pitch (helical twisting power) of liquid crystal by light irradiation, wherein, particularly in a case of a cholesteric liquid crystal phase, a selective reflection range is wide and color purity is high.

An eighth object of the invention is to provide a recording medium comprising a photo-reactive chiral agent which can substantially change a helical twisting power of liquid crystal by light irradiation to form a sharp image by changing a light quantity imagewise, wherein, for example, when a liquid crystal phase is a cholesteric crystal liquid phase, an image comprising a selectively reflected colors having a wide hue range and high color purity can be formed.

Elements according to the invention to solve these problems are described below.

According to a first aspect of the invention, there is provided an optically active isosorbide derivative as represented by the following general formula (I):

General formula (I)

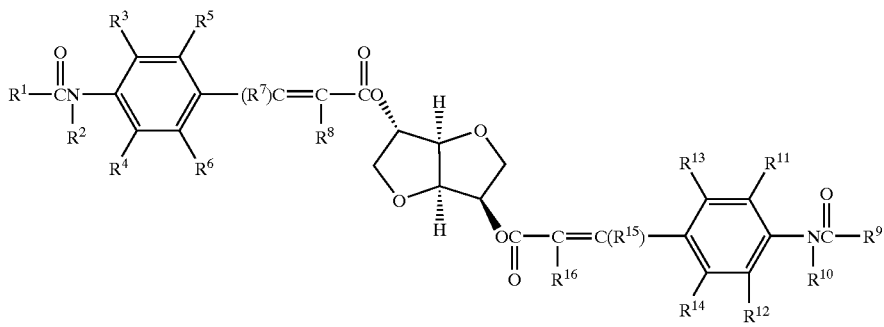

wherein $R^1$ and $R^9$ each independently represent a member selected from the group consisting of: an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of: a hydrogen atom, an alkyl group and an aryl group;

$R^2$ and $R^{10}$ each independently represent a member selected from the group consisting of: a hydrogen atom, an alkyl group and an aryl group;

$R^3$ to $R^6$ and $R^{11}$ to $R^{14}$ each independently represent a member selected from the group consisting of: a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

According to a second aspect of the invention, there is provided a production method of the optically active isosorbide derivative, wherein aryl halides as represented by the following general formulae (II) and (III) and an isosorbide derivative as represented by the following general formula (IV) are allowed to react with each other:

General Formula (II)

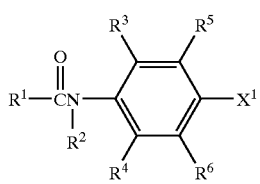

General Formula (III)

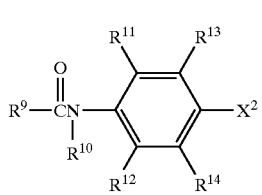

$X^1$, $X^2$; halogen atom

General Formula (IV)

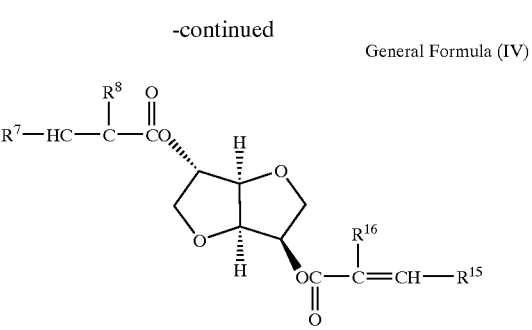

wherein $R^1$ to $R^{16}$ each independently represent a member equivalent to that as each independently represented by $R^1$ to $R^{16}$ in the general formula (I); and $X^1$ and $X^2$ each independently represent a halogen atom.

According to a third aspect of the invention, there is provided a photo-reactive chiral agent comprising the optically active isosorbide derivative as represented by the general formula (I).

According to a fourth aspect of the invention, there is provided a liquid crystal composition comprising at least one liquid crystalline compound and at least one type of the optically active isosorbide derivative as represented by the general formula (I).

According to a fifth aspect of the invention, there is provided a liquid crystal composition comprising a liquid crystalline compound having at least one polymerizable group, at least one type of the optically active isosorbide derivative as represented by the general formula (I) and a photo-polymerization initiator.

According to a sixth aspect of the invention, there is provided a liquid crystal composition comprising a liquid crystalline compound having at least one polymerizable group, at least one type of the optically active isosorbide derivative as represented by the general formula (I) and a photo-polymerization initiator, wherein the optically active isosorbide derivative as represented by the general formula (I) and the photo-polymerization initiator each have a different photosensitive wavelength region from each other.

According to the seventh aspect of the invention, there is provided a method for changing a helical structure of liquid crystal, wherein a structure of the optically active isosorbide derivative as represented by the general formula (I) is allowed to be changed by irradiating light on the liquid crystal composition comprising the optically active isosorbide derivative as represented by the general formula (I).

According to the eighth aspect of the invention, there is provided a method for fixing a helical structure of liquid crystal comprising the steps of:

irradiating imagewise light having a photosensitive wavelength region of the optically active isosorbide derivative as represented by the general formula (I) on the liquid crystal composition comprising the optically active isosorbide derivative as represented by the general formula (I); and irradiating light having a photosensitive wavelength region of the photo-polymerization agent on the thus-irradiated liquid crystal composition to perform photo-polymerization.

According to a ninth aspect of the invention, there is provided a liquid crystal color filter comprising at least one liquid crystalline compound and at least one type of the optically active isosorbide derivative as represented by the general formula (I).

According to a tenth aspect of the invention, there is provided an optical film comprising at least one liquid crystalline compound and at least one type of the optically active isosorbide derivative as represented by the general formula (I).

According to an eleventh aspect of the invention, there is provided a recording medium comprising at least one liquid crystalline compound and at least one type of the optically active isosorbide derivative as represented by the general formula (I).

According to a twelfth aspect of the invention, there is provided an optically active isomannide derivative as represented by the following general formula (V):

wherein $R^7$, $R^8$, $R^{15}$ and $R^{16}$ each independently represent a member equivalent to that as each independently represented by $R^7$, $R^8$, $R^{15}$ and $R^{16}$ in the general formula (I).

According to a fourteenth aspect of the invention, there is provided a photo-reactive chiral agent comprising the optically active isomannide derivative as represented by the general formula (V).

According to a fifteenth aspect of the invention, there is provided a liquid crystal composition comprising at least one liquid crystalline compound and at least one type of the optically active isomannide derivative as represented by the general formula (V).

According to a sixteenth aspect of the invention, there is provided a liquid crystal composition comprising a liquid crystalline compound having at least one polymerizable group, at least one type of the optically active isomannide derivative as represented by the general formula (V) and a photo-polymerization initiator.

According to a seventeenth aspect of the invention, there is provided a liquid crystal composition comprising a liquid crystalline compound having at least one polymerizable group, at least one type of the optically active isomannide derivative as represented by the general formula (V) and a photo-polymerization initiator, wherein the optically active General Formula (V)

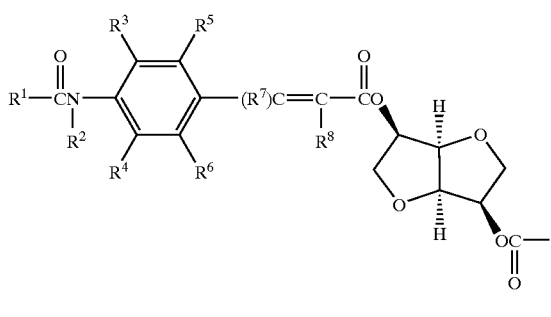

wherein $R^1$ to $R^{16}$ each independently represent a member equivalent to that as each independently represented by $R^1$ to $R^{16}$ in the general formula (I).

According to a thirteenth aspect of the invention, there is provided a production method of the optically active isomannide derivative as represented by the general formula (V), wherein aryl halides as represented by the general formulae (II) and (III) and an isomannide derivative as represented by the following general formula (VI) are allowed to react with each other:

General Formula (VI)

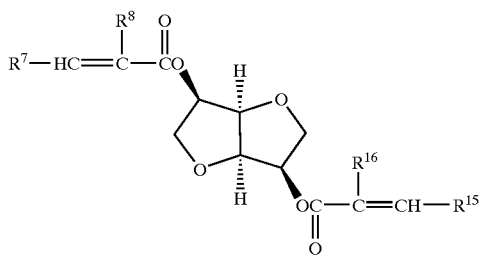

isomannide derivative as represented by the general formula (V) and the photo-polymerization initiator each have a different photosensitive wavelength region from each other.

According to the eighteenth aspect of the invention, there is provided a method for changing a helical structure of liquid crystal, wherein a structure of the optically active isomannide derivative as represented by the general formula (V) is allowed to be changed by irradiating light on the liquid crystal composition comprising the optically active isomannide derivative as represented by the general formula (V).

According to the nineteenth aspect of the invention, there is provided a method for fixing a helical structure of liquid crystal comprising the steps of:

irradiating imagewise light having a photosensitive wavelength region of the optically active isomannide derivative as represented by the general formula (V) on the liquid crystal composition comprising the optically active isomannide derivative as represented by the general formula (V); and irradiating light having a photosensitive wavelength region of the photo-polymerization agent on the thus-irradiated liquid crystal composition to perform photo-polymerization.

According to a twentieth aspect of the invention, there is provided a liquid crystal color filter comprising at least one liquid crystalline compound and at least one type of the optically active isomannide derivative as represented by the general formula (V).

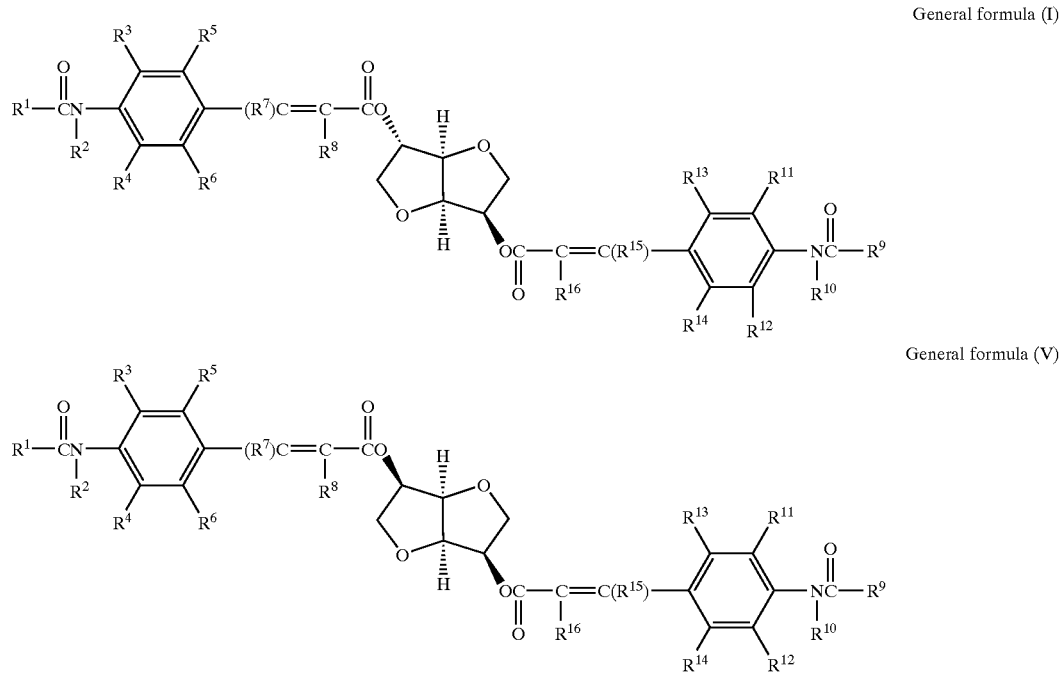

General formula (I)

General formula (V)

According to a twenty-first aspect of the invention, there is provided an optical film comprising at least one liquid crystalline compound and at least one type of the optically active isomannide derivative as represented by the general formula (V).

According to a twenty-second aspect of the invention, there is provided a recording medium comprising at least one liquid crystalline compound and at least one type of the optically active isomannide derivative as represented by the general formula (V).

DESCRIPTION OF THE PREFERRED EMBODIMENTS

Figure 1A:
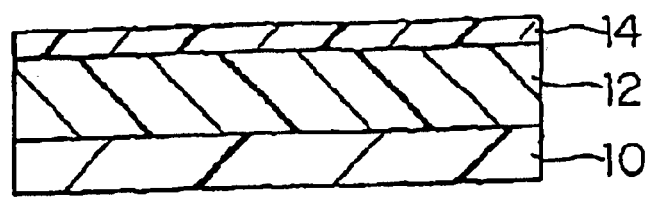
FIGS. 1A to 1D are each a schematic diagram showing a part of processes for producing a liquid crystal color filter according to the present invention.

Optically Active Isosorbide Derivative and Optically Active Isomannide Derivative Hereinafter, an optically active isosorbide derivative and an optically active isomannide derivative according to the present invention are described in detail.

The isosorbide derivative according to the invention and the isomannide derivative according to the invention are represented by the following general formulae (I) and (V), respectively, and are each an optically active compound whereupon they themselves each perform cis-trans isomerization by light, thereby changing a structure thereof and, particularly, have sensitivity in a wavelength region of 365 nm and a vicinity thereof:

wherein $R^1$ and $R^9$ each independently represent a member selected from the group consisting of: an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of: a hydrogen atom, an alkyl group and an aryl group;

$R^2$ and $R^{10}$ each independently represent a member selected from the group consisting of: a hydrogen atom, an alkyl group and an aryl group;

$R^3$ to $R^6$ and $R^{11}$ to $R^{14}$ each independently represent a member selected from the group consisting of: a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

The alkyl group as each independently represented by $R^1$ and $R^9$ may either be non-substituted or be substituted by a substituent and is preferably an alkyl group having from 1 to 30 carbon atoms in total and particularly preferably an alkyl group having from 1 to 20 carbon atoms in total.

Examples of preferable substituents in a case of such substitution include a halogen atom, an aryl group, an alkenyl group, an alkynyl group, an alkoxy group, an acyl group, an alkoxycarbonyl group, an aryloxycarbonyl group, an acyloxy group, a cyano group and a hydroxyl group and, thereamong, the halogen atom, the alkoxy group and the acyloxy group are particularly preferable.

Specific examples of such alkyl groups include a methyl group, a pentyl group, a cyclohexyl group, a trifluoromethyl group, a benzyl group, an allyl group, a methoxyethyl group and an acetyloxymethyl group.

The alkenyl group as each independently represented by $R^1$ and $R^9$ may either be non-substituted or be substituted by a substituent and is preferably an alkenyl group having from 2 to 30 carbon atoms in total and particularly preferably an alkenyl group having from 2 to 20 carbon atoms in total.

Examples of preferable substituents in a case of such substitution include a halogen atom, an aryl group, an alkynyl group, an alkoxy group, an acyl group, an alkoxycarbonyl group, an aryloxycarbonyl group, an acyloxy group, a cyano group and a hydroxyl group acid, thereamong, the aryl group, the alkoxy group and the acyloxy group are particularly preferable.

Specific examples of such alkenyl groups include a vinyl group, a phenylethenyl group, a 4-pentyloxyphenylethenyl group and a methoxyvinyl group.

The aryl group and the heterocyclic group as each independently represented by $R^1$ and $R^9$ may either be non-substituted or be substituted by a substituent and are preferably an aryl group and a heterocyclic group each having from 4 to 40 carbon atoms in total and particularly preferably an aryl group and a heterocyclic group each having from 4 to 30 carbon atoms in total.

Examples of preferable substituents in a case of such substitution include a halogen atom, an alkyl group, an alkenyl group, an alkynyl group, an alkoxy group, an acyl group, an alkoxycarbonyl group, an aryloxycarbonyl group, an acyloxy group, a cyano group and a hydroxyl group and, thereamong, the halogen atom, the alkyl group, the alkenyl group, the alkoxy group, the alkoxycarbonyl group, the acyloxy group and the hydroxyl group are particularly preferable.

Specific examples of such aryl groups include a phenyl group, a β-naphthyl group, a 4-methylphenyl group, a 4-vinylphenyl group, a 4-butyloxyphenyl group, a 4-benzoyloxyphenyl group and a pyrimidine-2-yl group.

Further, specific preferable examples of such heterocyclic groups include a pyridine ring, a pyrimidine ring, a furan ring and a benzofuran ring and, thereamong, the pyridine ring and the pyrimidine ring are particularly preferable.

The alkoxy group as each independently represented by $R^1$ and $R^9$ may either be non-substituted or be substituted by a substituent and is preferably an alkoxy group having from 1 to 30 carbon atoms in total and more preferably an alkoxy group having from 1 to 20 carbon atoms in total.

Examples of preferable substituents in a case of such substitution include a halogen atom, an aryl group, an alkenyl group, an alkynyl group, an alkoxy group, an acyl group, an alkoxycarbonyl group, an aryloxycarbonyl group, an acyloxy group, a cyano group, a hydroxyl group and a carboxyl group and, thereamong, the halogen atom, the aryl group, the alkoxy group, the acyloxy group and the alkoxycarbonyl group are particularly preferable.

Specific examples of such alkoxy groups include a methoxy group, a butyloxy group, a benzyloxy group, a methoxyethoxyethoxy group, an acetyloxyhexyloxy group and a benzoyloxydodecyloxy group.

The aryloxy group as each independently represented by $R^1$ and $R^9$ may either be non-substituted or be substituted by a substituent and is preferably an aryloxy group having from 4 to 40 carbon atoms in total and particularly preferably an aryloxy group having from 4 to 30 carbon atoms in total; further, an aryl portion thereof may be a heterocycle.

Examples of substituents in a case of such substitution include a halogen atom, an alkyl group, an alkenyl group, an alkynyl group, an alkoxy group, an acyl group, an alkoxycarbonyl group, an aryloxycarbonyl group, an acyloxy group and a cyano group and, thereamong, the halogen atom, the alkyl group, the alkoxy group, the aryloxycarbonyl group and the cyano group are particularly preferable.

Specific examples of such aryloxy groups include a phenoxy group, a biphenyloxy group, a β-naphthyloxy group, a 4-phenoxycarbonylphenoxy group and a methoxyphenoxy group.

$R^{17}$ and $R^{18}$ in the $-NR^{17}R^{18}$ group as each independently represented by $R^1$ and $R^9$ each independently represent a member selected from the group consisting of: a hydrogen atom, an alkyl group and an aryl group.

The alkyl group as each independently represented by $R^{17}$ and $R^{18}$ may either be non-substituted or substituted by a substituent and is preferably an alkyl group having from 1 to 20 carbon atoms in total and particularly preferably an alkyl group having from 1 to 12 carbon atoms in total. Examples of preferable substituents in a case of such substitution include a halogen atom, an alkoxy group and an aryl group.

Specific examples of such alkyl groups include a methyl group, a butyl group, a trifluoromethyl group, a methoxyethyl group and a benzyl group.

The aryl group each independently represented by $R^{17}$ and $R^{18}$ may either be non-substituted or substituted by a substituent and is preferably an aryl group having from 6 to 30 carbon atoms in total and particularly preferably an aryl group having from 6 to 20 carbon atoms in total. Examples of preferable substituents, in a case of such substitution, include a halogen atom, an alkyl group, an alkenyl group, an alkoxy group and a cyano group and, thereamong, the halogen atom, the alkyl group and the alkoxy group are particularly preferable.

Specific examples of such aryl groups include a phenyl group, a β-naphthyl group, a 4-methylphenyl group, a 4-butyloxyphenyl group and a 4-fluorophenyl group. Among groups represented by $-NR^{17}R^{18}$, $-NHR^{17}$ is particularly preferable.

Further, the alkyl group, the aryl group, the alkenyl group, the alkoxy group, the aryloxy group and $-NR^{17}R^{18}$ as each independently represented by $R^1$ and $R^9$ may each be substituted by at least one of the following groups:

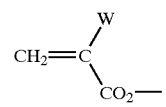 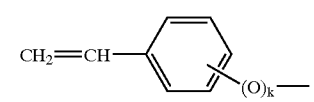

W: H, CH$_3$　　　　　　　　　k: 0, 1

Among the above-described groups each independently represented by $R^1$ and $R^9$, it is preferable that $R^1$ and $R^9$ each independently represent an alkyl group or an aryl group; it is particularly preferable that $R^1$ and $R^9$ represent a same alkyl or aryl group with each other.

The alkyl group as each independently represented by $R^2$ and $R^{10}$ may either be non-substituted or be substituted by a substituent and is preferably an alkyl group having from 1 to 20 carbon atoms in total and particularly preferably an alkyl group having from 1 to 8 carbon atoms in total.

Preferable examples of such substituents include a halogen atom and an alkoxy group. Specific examples of such alkyl groups include a methyl group, a butyl group, a trifluoromethyl group and a methoxyethyl group.

The aryl group as each independently represented by $R^2$ and $R^{10}$ may either be non-substituted or be substituted by a substituent and is preferably an aryl group having from 6 to 30 carbon atoms in total and particularly preferably an aryl group having from 6 to 20 carbon atoms in total. Examples of such substituents include a halogen atom, an alkyl group and an alkoxy group.

Specific examples of such aryl groups include a phenyl group, a β-naphthyl group, a 4-methylphenyl group, a 4-chlorophenyl group and a 4-methoxyphenyl group.

Among the above-described groups as each independently represented by $R^2$ and $R^{10}$, it is preferable that each of $R^2$ and $R^{10}$ and a hydrogen atom or, as described below, $R^2$ and $R^4$, and $R^{10}$ and $R^{12}$ may, in each combination, be combined with each other to form a 5- or 6-membered ring. Further, it is preferable that $R^2$ and $R^{10}$ represent a same group with each other.

Examples of preferable halogen atoms as each independently represented by $R^3$ to $R^6$, and $R^{11}$ to $R^{14}$ include a fluorine atom and a chlorine atom and, therebetween, the fluorine atom is particularly preferable.

Such alkyl groups as each independently represented by $R^3$ to $R^6$, and $R^{11}$ to $R^{14}$ are equivalent to the above-described alkyl groups as each independently represented by $R^2$ and $R^{10}$. Same applies to preferable groups.

The alkoxy group as each independently represented by $R^3$ to $R^6$, and $R^{11}$ to $R^{14}$ may either be non-substituted or be substituted by a substituent and is preferably an alkoxy group having from 1 to 20 carbon atoms in total and particularly preferably an alkoxy group having from 1 to 8 carbon atoms in total. As an example of the substituent, a halogen atom is preferable; specific examples of such alkoxy groups include a methoxy group and a trifluoromethoxy group.

Among the above-described groups as each independently represented by $R^3$ to $R^6$, and $R^{11}$ to $R^{14}$, it is preferable that $R^3$ to $R^6$, and $R^{11}$ to $R^{14}$ each independently represent a member selected from the group consisting of: a hydrogen atom, an alkyl group and an alkoxy group; a case in which all of $R^3$ to $R^6$ represent a hydrogen atom or any one of the substituents is an alkyl group or an alkoxy group, and all of $R^{11}$ to $R^{14}$ represent a hydrogen atom or any one of the substituents is an alkyl group or an alkoxy group are particularly preferable. Further, a case in which $R^3$ and $R^{11}$, $R^4$ and $R^{12}$, $R^5$ and $R^3$, and $R^6$ and $R^{14}$ represent, in each combination, a same group with each other is preferable.

Such alkyl groups as each independently represented by $R^7$ and $R^{15}$ are equivalent to the above-described alkyl groups as each independently represented by $R^2$ and $R^{10}$ and same applies to preferable groups. Particularly, as $R^7$ and $R^{15}$, a hydrogen atom is preferable, and $R^7$ and $R^{15}$ preferably represent a same group with each other.

Such alkyl groups as each independently represented by $R^8$ and $R^{16}$ are equivalent to the above-described alkyl groups as each independently represented by $R^2$ and $R^{10}$ and same applies to preferable groups. Particularly, as $R^8$ and $R^{16}$, a hydrogen atom is preferable, and $R^8$ and $R^{16}$ preferably represent a same group with each other.

When $R^2$ and $R^4$ are combined with each other to form a 5- or 6-membered ring, it is preferable that atoms constituting the ring are a combination of a carbon atom and a nitrogen atom, or another combination of a carbon atom, a nitrogen atom and an oxygen atom.

Particularly, a 5-membered ring or a 6-membered ring as represented by the following formula is preferable:

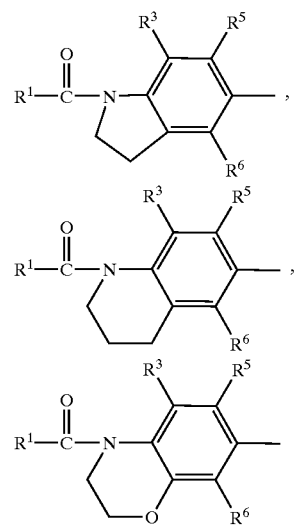

Also, when $R^{10}$ and $R^{12}$ are combined with each other to form a 5- or 6-membered ring, it is preferable that atoms constituting the ring are a combination of a carbon atom and a nitrogen atom, or another combination of a carbon atom, a nitrogen atom and an oxygen atom.

Same applies to particularly preferable 5- or 6-membered ring; on this occasion, it is preferable that $R^1$, $R^3$, $R^5$ and $R^6$ in the above-described formula are replaced by $R^9$, $R^{11}$, $R^{13}$ and $R^{14}$, respectively.

Since a double bond is present between an isosorbide nucleus and a benzene ring in the optically active isosorbide derivative as represented by the general formula (I) according to the invention and between an isomannide nucleus and a benzene ring in the optically active isomannide derivative as represented by the general formula (V) according to the invention, there exist geometric isomers (cis form and trans form) in each of these cases due to a difference in configurations of both cases. Although the optically active isosorbide derivative according to the invention and the optically active isomannide derivative according to the invention each include the cis form, the trans form and a combination thereof, from the standpoint of a large change ratio of helical twisting power and an easiness of synthesis, it is preferable that each derivative is in a trans form before being irradiated by light, while, when it is irradiated by light, it changes the structure thereof into a cis-form.

Specific examples of the optically active isosorbide derivatives as represented by the general formula (I) according to the invention are shown below as illustrative compounds: 1–1 to 1–49, 2–1 to 2–27, 3–1 to 3–7, 4–1 to 4–4 and 5–1 to 5–5. However, these examples are given to illustrate the invention and the invention is by no means limited thereto. It should be interpreted that the examples further include respective cis forms which are geometric isomers thereof.

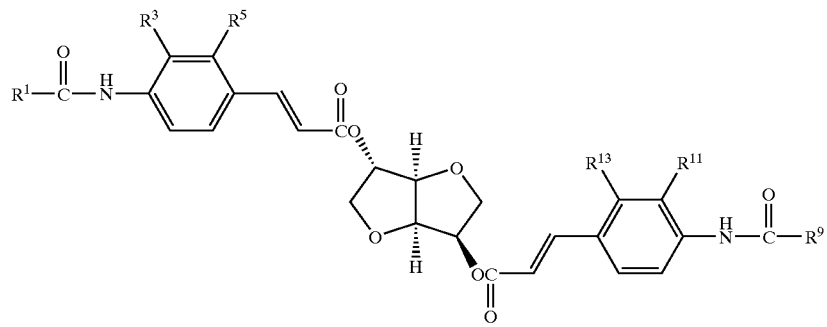

| No. | —$R^1$ | —$R^3$ | —$R^5$ | —$R^9$ | —$R^{11}$ | —$R^{13}$ |
|---|---|---|---|---|---|---|
| 1-1 | phenyl | —H | —H | —$R^1$ | —$R^3$ | —$R^5$ |
| 1-2 | o-methylphenyl | —H | —H | —$R^1$ | —$R^3$ | —$R^5$ |
| 1-3 | 6-(2-ethylhexyloxy)naphthalen-2-yl | —H | —H | —$R^1$ | —$R^3$ | —$R^5$ |
| 1-4 | —$C_7H_{15}(n)$ | —H | —H | —$R^1$ | —$R^3$ | —$R^5$ |
| 1-5 | —$OC_2H_5$ | —H | —H | —$R^1$ | —$R^3$ | —$R^5$ |
| 1-6 | —NH-phenyl | —H | —H | —$R^1$ | —$R^3$ | —$R^5$ |
| 1-7 | phenyl | —$OCH_3$ | —H | —$R^1$ | —$R^3$ | —$R^5$ |
| 1-8 | o-fluorophenyl | —$OCH_3$ | —H | —$R^1$ | —$R^3$ | —$R^5$ |
| 1-9 | o-methylphenyl | —$OCH_3$ | —H | —$R^1$ | —$R^3$ | —$R^5$ |
| 1-10 | 4-($CO_2CH_3$)phenyl | —$OCH_3$ | —H | —$R^1$ | —$R^3$ | —$R^5$ |
| 1-11 | 2,6-dimethylphenyl | —$OCH_3$ | —H | —$R^1$ | —$R^3$ | —$R^5$ |

-continued
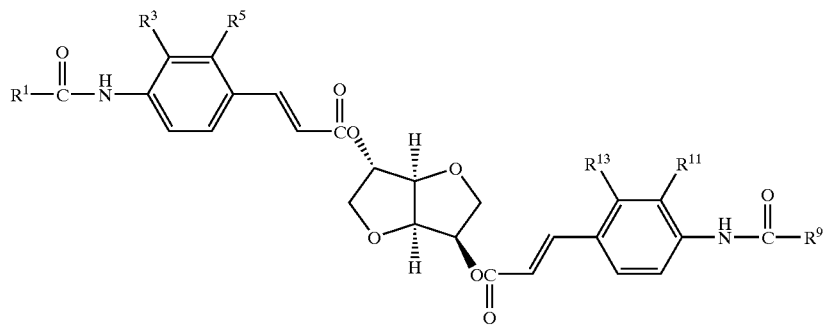
| No. | —R¹ | —R³ | —R⁵ | —R⁹ | —R¹¹ | —R¹³ |
|---|---|---|---|---|---|---|
| 1-12 | —C₆H₄—OC₃H₇(n) | —OCH₃ | —H | —R¹ | —R³ | —R⁵ |
| 1-13 | —C₆H₄(OCH₃) (ortho) | —OCH₃ | —H | —R¹ | —R³ | —R⁵ |
| 1-14 | —cyclohexyl | —OCH₃ | —H | —R¹ | —R³ | —R⁵ |
| 1-15 | —C₅H₁₁(n) | —OCH₃ | —H | —R¹ | —R³ | —R⁵ |
| 1-16 | —CH=CH₂ | —OCH₃ | —H | —R¹ | —R³ | —R⁵ |
| 1-17 | —NH—cyclohexyl | —OCH₃ | —H | —R¹ | —R³ | —R⁵ |
| 1-18 | —OC₆H₁₃(n) | —OCH₃ | —H | —R¹ | —R³ | —R⁵ |
| 1-19 | —NHCH₂—C₆H₅ | —OCH₃ | —H | —R¹ | —R³ | —R⁵ |
| 1-20 | —C₆H₅ | —CH₃ | —H | —R¹ | —R³ | —R⁵ |
| 1-21 | —C₆H₄—OC(O)C₆H₅ | —CH₃ | —H | —R¹ | —R³ | —R⁵ |
| 1-22 | —C₆H₄—C₅H₁₁(n) | —CH₃ | —H | —R¹ | —R³ | —R⁵ |
| 1-23 | —(CH₂)₃O—C(O)—CH=CH₂ | —F | —H | —R¹ | —R³ | —R⁵ |
| 1-24 | —NH—cyclohexyl | —C₂H₅ | —H | —R¹ | —R³ | —R⁵ |

-continued

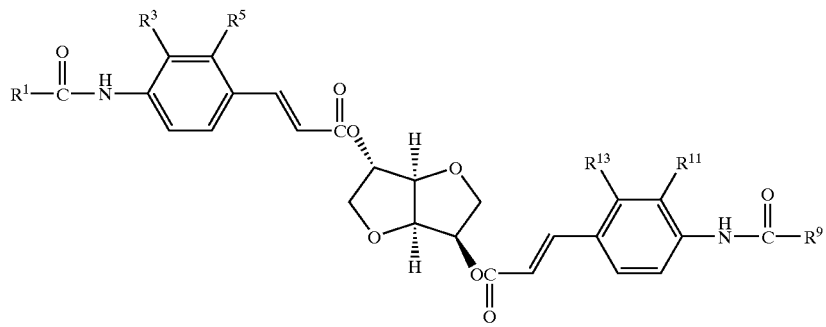

| No. | —R¹ | —R³ | —R⁵ | —R⁹ | —R¹¹ | —R¹³ |
|---|---|---|---|---|---|---|
| 1-25 | —⟨C₆H₄⟩—OH | —H | —OCH₃ | —R¹ | —R³ | —R⁵ |
| 1-26 | —⟨C₆H₅⟩ | —H | —OCH₃ | —R¹ | —R³ | —R⁵ |
| 1-27 | —⟨C₆H₄⟩—O—C(O)—⟨C₆H₅⟩ | —H | —OCH₃ | —R¹ | —R³ | —R⁵ |
| 1-28 | —⟨C₆H₄⟩—O—C(O)—⟨C₆H₄⟩—CH₃ | —H | —OCH₃ | —R¹ | —R³ | —R⁵ |
| 1-29 | —⟨C₆H₄⟩—O—C(O)—⟨C₆H₄⟩—F | —H | —OCH₃ | —R¹ | —R³ | —R⁵ |
| 1-30 | —⟨C₆H₄⟩—O—C(O)—⟨C₆H₄⟩—OCH₃ | —H | —OCH₃ | —R¹ | —R³ | —R⁵ |
| 1-31 | —⟨C₆H₄⟩—O—C(O)—⟨C₆H₄⟩—C(O)OCH₃ | —H | —OCH₃ | —R¹ | —R³ | —R⁵ |
| 1-32 | —⟨C₆H₄⟩—O—C(O)—⟨C₆H₄⟩—Cl | —H | —OCH₃ | —R¹ | —R³ | —R⁵ |
| 1-33 | —⟨C₆H₄⟩—O—C(O)—⟨C₆H₄⟩—⟨C₆H₅⟩ | —H | —OCH₃ | —R¹ | —R³ | —R⁵ |
| 1-34 | —⟨C₆H₄⟩—O—C(O)—⟨C₆H₅⟩ | —H | —OCH₃ | —R¹ | —R³ | —R⁵ |
| 1-35 | —C₇H₁₅(n) | —H | —OCH₃ | —R¹ | —R³ | —R⁵ |
| 1-36 | —⟨C₆H₄⟩—O—C(O)—CH=CH₂ | —H | —OCH₃ | —R¹ | —R³ | —R⁵ |

-continued

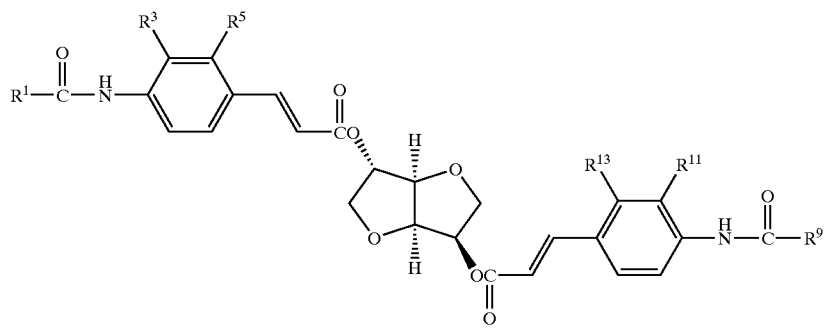

| No. | —R¹ | —R³ | —R⁵ | —R⁹ | —R¹¹ | —R¹³ |
|---|---|---|---|---|---|---|
| 1-37 | —CH=CH—C₆H₄—OCH₃ (4-methoxystyryl) | —H | —OCH₃ | —R¹ | —R³ | —R⁵ |
| 1-38 | —O—CH₂—CH(C₂H₅)—C₄H₉ | —H | —OCH₃ | —R¹ | —R³ | —R⁵ |
| 1-39 | —NH—CH₂—CH(C₂H₅)—C₄H₉ | —H | —OCH₃ | —R¹ | —R³ | —R⁵ |
| 1-40 | —O—C₆H₅ | —H | —OCH₃ | —R¹ | —R³ | —R⁵ |
| 1-41 | —C₆H₅ | —H | —CH₃ | —R¹ | —R³ | —R⁵ |
| 1-42 | —C₆H₁₁ (cyclohexyl) | —H | —CH₃ | —R¹ | —R³ | —R⁵ |
| 1-43 | —C₆H₄—C₆H₅ (4-biphenyl) | —H | —Cl | —R¹ | —R³ | —R⁵ |
| 1-44 | —C₆H₅ | —CH₃ | —CH₃ | —R¹ | —R³ | —R⁵ |
| 1-45 | —C₆H₄—OC₂H₅ (4-ethoxyphenyl) | —OCH₃ | —Cl | —R¹ | —R³ | —R⁵ |
| 1-46 | —C₆H₄—CH₃ (4-methylphenyl) | —OCH₃ | —H | —C₆H₄—C₆H₁₃(n) | —OCH₃ | —H |
| 1-47 | —C₆H₄—CH=CH₂ (4-vinylphenyl) | —OCH₃ | —H | —C₆H₄—CH=CH₂ | —H | —H |

-continued
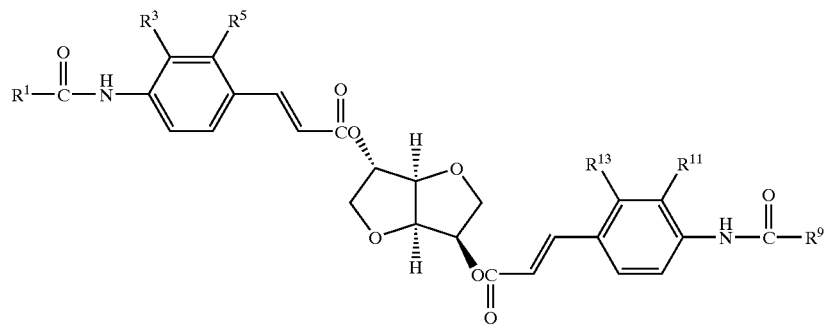
| No. | —R¹ | —R³ | —R⁵ | —R⁹ | —R¹¹ | —R¹³ |
|---|---|---|---|---|---|---|
| 1-48 | 4-ethylphenyl | —OCH₃ | —H | 2-methoxyphenyl | —H | —H |
| 1-49 | 4-acetylphenyl | —Cl | —OCH₃ | 4-acetylphenyl | —H | —OCH₃ |
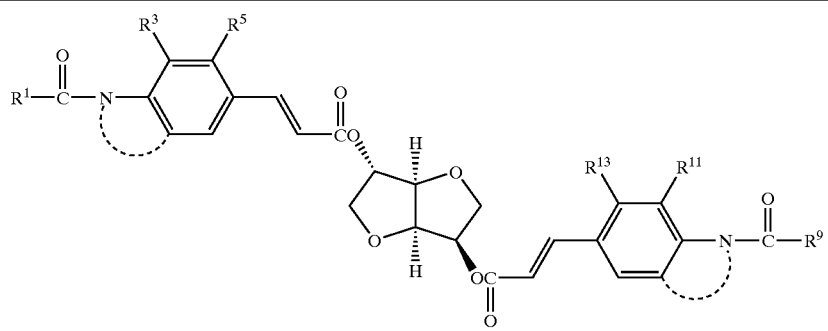
| No. | R¹–C(O)–N-indoline (left) | R⁹–C(O)–N-indoline (right) |
|---|---|---|
| 2-1 | phenyl-C(O)-(5-methylindolin-1-yl) | phenyl-C(O)-(5-methylindolin-1-yl) |
| 2-2 | 4-methylphenyl-C(O)-(5-methylindolin-1-yl) | 4-methylphenyl-C(O)-(5-methylindolin-1-yl) |
| 2-3 | 4-cyclohexylphenyl-C(O)-(5-methylindolin-1-yl) | 4-cyclohexylphenyl-C(O)-(5-methylindolin-1-yl) |

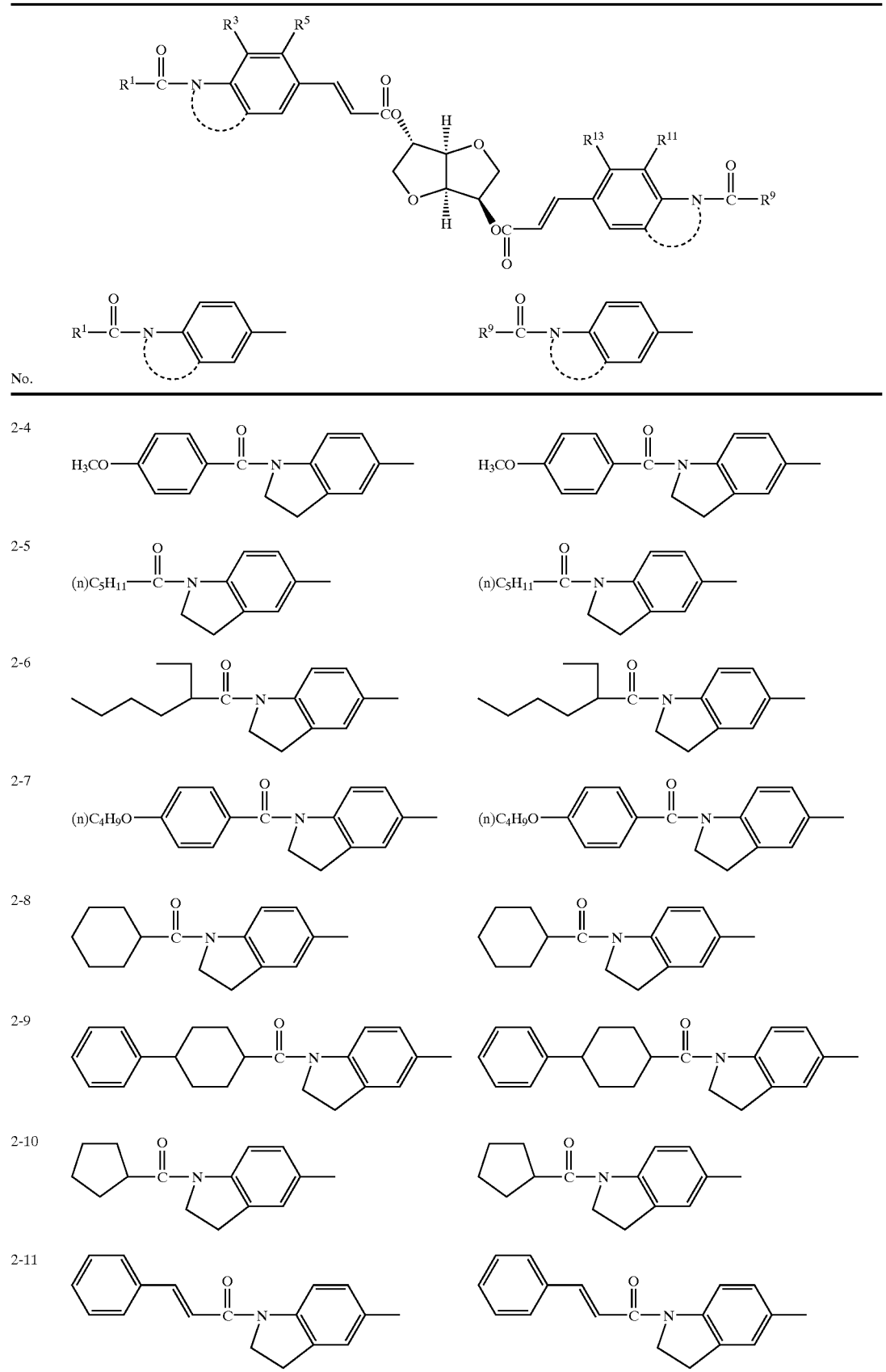

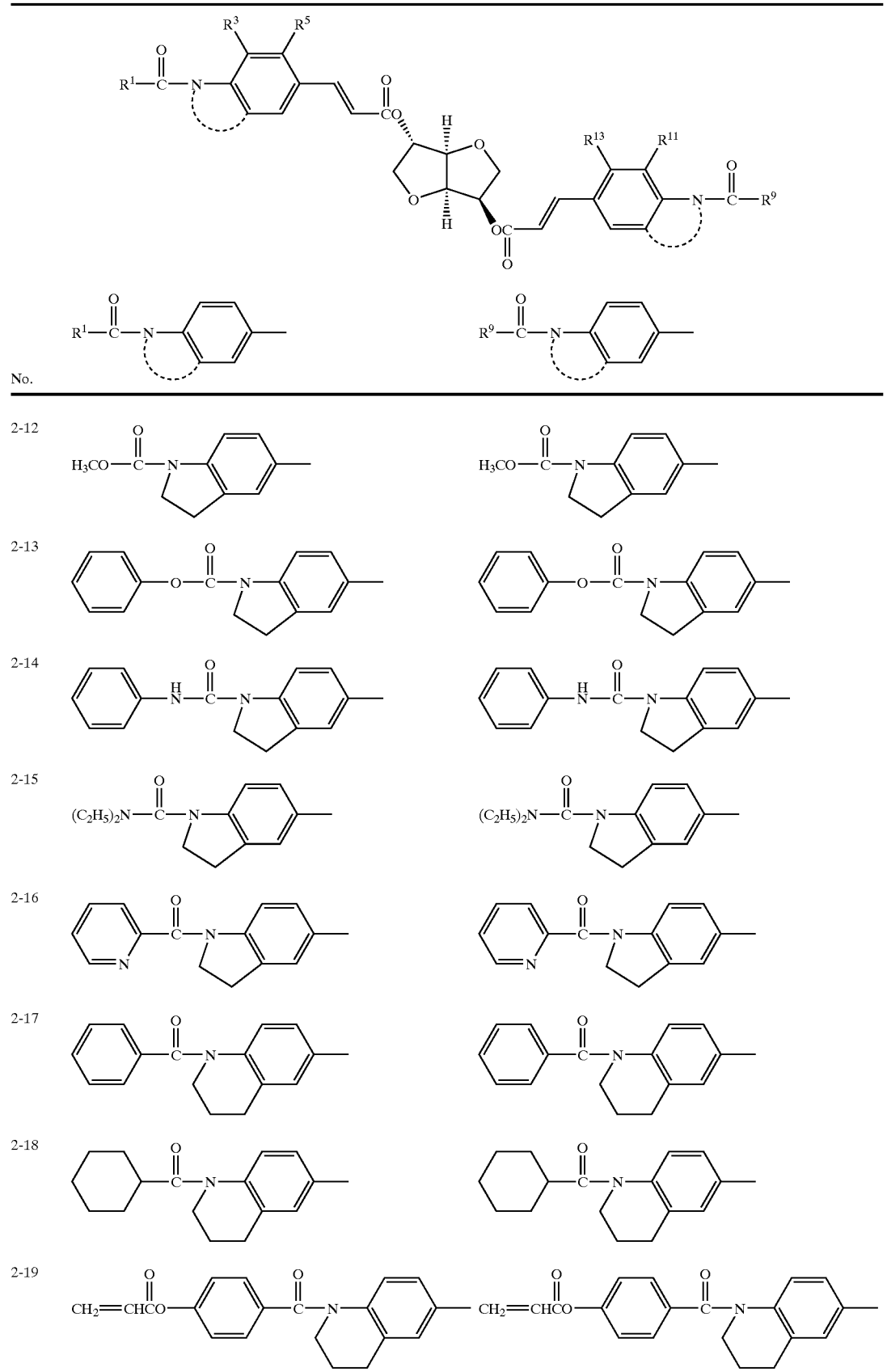

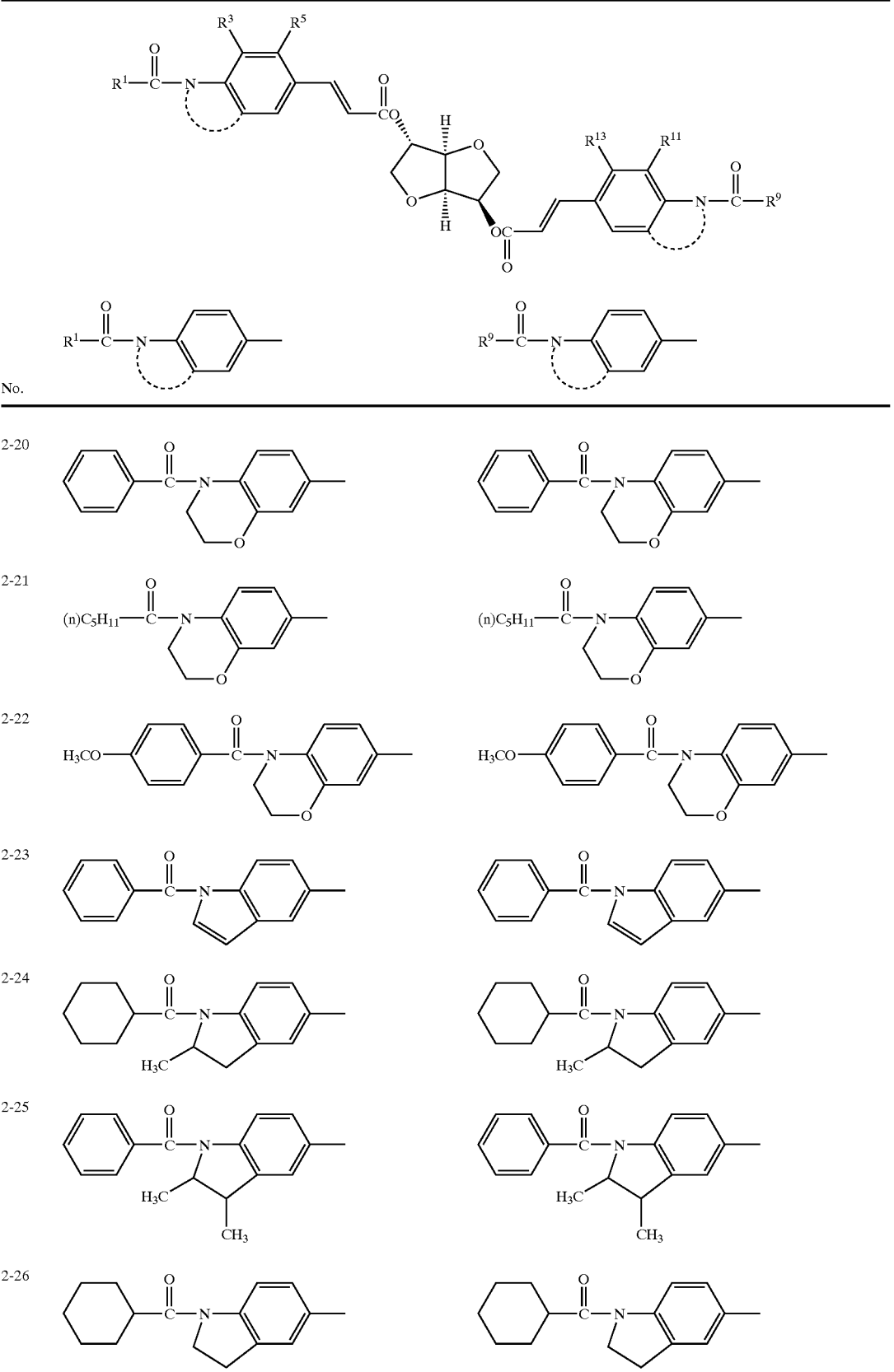

-continued
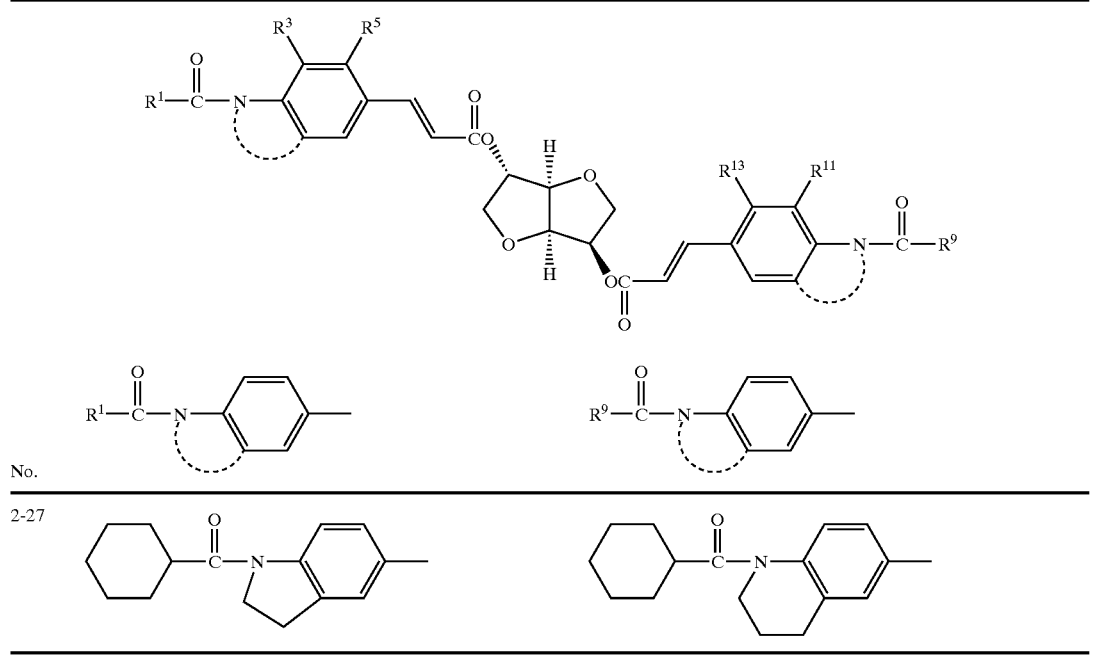
| No. | | |
|---|---|---|
| 2-27 | | |
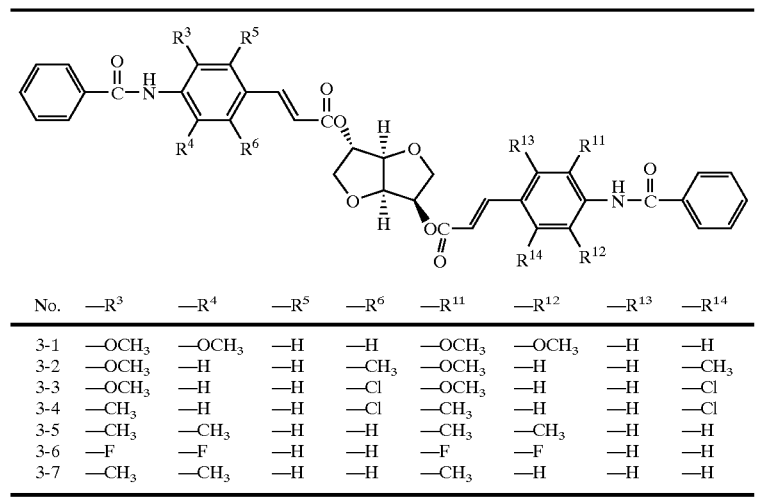
| No. | —R³ | —R⁴ | —R⁵ | —R⁶ | —R¹¹ | —R¹² | —R¹³ | —R¹⁴ |
|---|---|---|---|---|---|---|---|---|
| 3-1 | —OCH₃ | —OCH₃ | —H | —H | —OCH₃ | —OCH₃ | —H | —H |
| 3-2 | —OCH₃ | —H | —H | —CH₃ | —OCH₃ | —H | —H | —CH₃ |
| 3-3 | —OCH₃ | —H | —H | —Cl | —OCH₃ | —H | —H | —Cl |
| 3-4 | —CH₃ | —H | —H | —Cl | —CH₃ | —H | —H | —Cl |
| 3-5 | —CH₃ | —CH₃ | —H | —H | —CH₃ | —CH₃ | —H | —H |
| 3-6 | —F | —F | —H | —H | —F | —F | —H | —H |
| 3-7 | —CH₃ | —CH₃ | —H | —H | —CH₃ | —H | —H | —H |
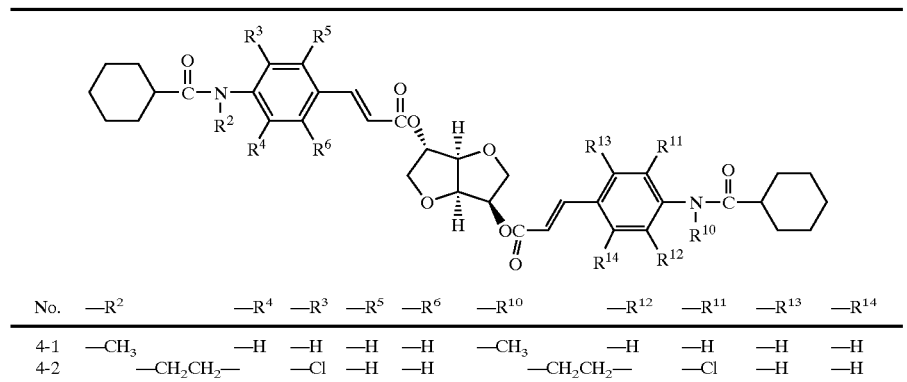
| No. | —R² | —R⁴ | —R³ | —R⁵ | —R⁶ | —R¹⁰ | —R¹² | —R¹¹ | —R¹³ | —R¹⁴ |
|---|---|---|---|---|---|---|---|---|---|---|
| 4-1 | —CH₃ | —H | —H | —H | —H | —CH₃ | —H | —H | —H | —H |
| 4-2 | —CH₂CH₂— | | —Cl | —H | —H | —CH₂CH₂— | | —Cl | —H | —H |

-continued
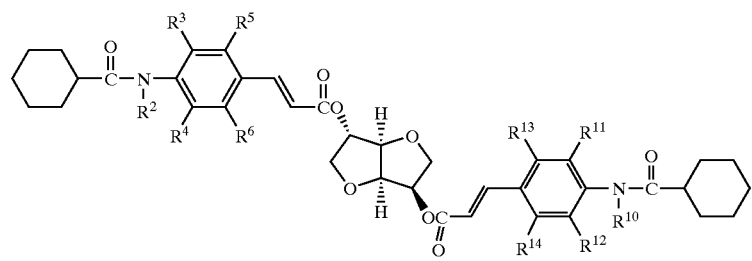
| No. | —R² | —R⁴ | —R³ | —R⁵ | —R⁶ | —R¹⁰ | —R¹² | —R¹¹ | —R¹³ | —R¹⁴ |
|---|---|---|---|---|---|---|---|---|---|---|
| 4-3 | 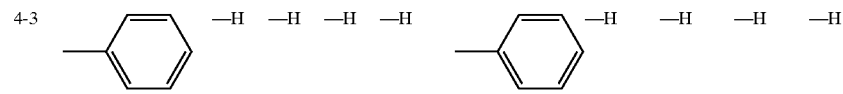 | —H | —H | —H | —H |  | —H | —H | —H | —H |
| 4-4 | —CH₂CH₂— | —H | —H | —CH₃ | | —CH₂CH₂— | —H | —H | —H | |
No. 5-1
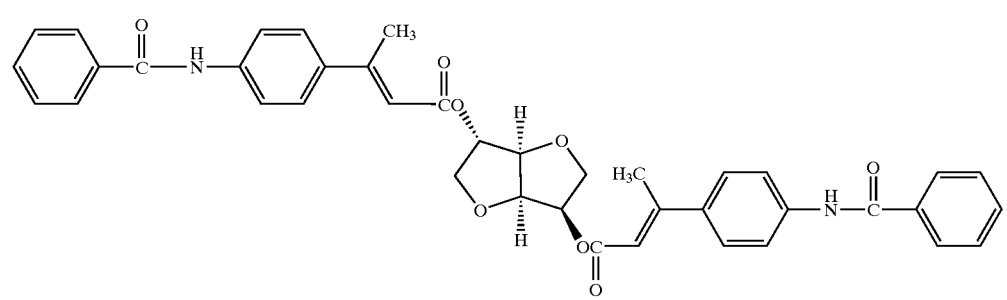
No. 5-2
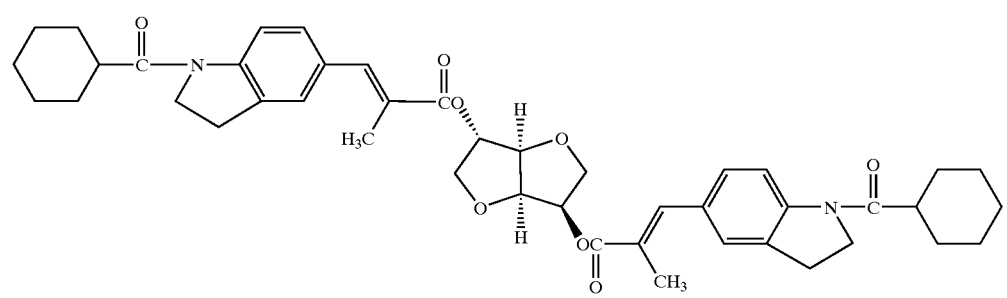
No. 5-3
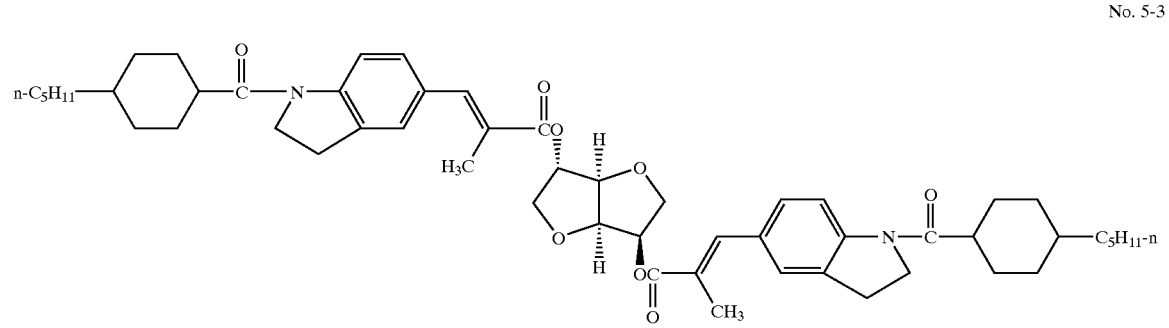

-continued

No. 5-4

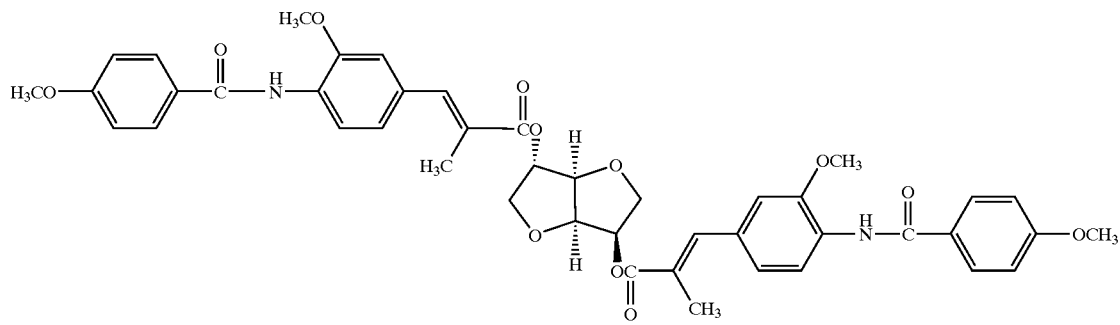

No. 5-5

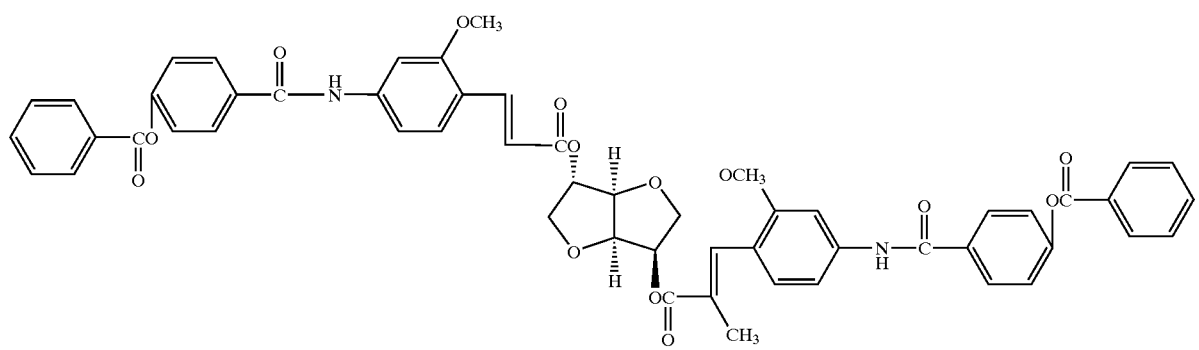

Specific examples of the optically active isomannide derivatives as represented by the general formula (V) according to the invention are shown below as illustrative compounds: 1'-1 to 1'-49, 2'-1 to 2'-27, 3'-1 to 3'-7, 4'-1 to 4'-4 and 5'-1 to 5'-5. However, these examples are given to illustrate the invention and the invention is by no means limited thereto. It should be interpreted that the examples further include respective cis forms which are geometric isomers thereof.

| No. | —$R^1$ | —$R^3$ | —$R^5$ | —$R^9$ | —$R^{11}$ | —$R^{13}$ |
|---|---|---|---|---|---|---|
| 1'-1 | phenyl | —H | —H | —$R^1$ | —$R^3$ | —$R^5$ |
| 1'-2 | 2-methylphenyl | —H | —H | —$R^1$ | —$R^3$ | —$R^5$ |

-continued

[Structure: R¹–C(=O)–NH–[phenyl with R³, R⁵]–CH=CH–C(=O)–O–[bicyclic dioxabicyclic sugar (isosorbide-like)]–O–C(=O)–CH=CH–[phenyl with R¹¹, R¹³]–NH–C(=O)–R⁹]

| No. | —R¹ | —R³ | —R⁵ | —R⁹ | —R¹¹ | —R¹³ |
|---|---|---|---|---|---|---|
| 1'-3 | 6-(2-ethylhexyloxy)naphthalen-2-yl | —H | —H | —R¹ | —R³ | —R⁵ |
| 1'-4 | —C₇H₁₅(n) | —H | —H | —R¹ | —R³ | —R⁵ |
| 1'-5 | —OC₂H₅ | —H | —H | —R¹ | —R³ | —R⁵ |
| 1'-6 | —NH—phenyl | —H | —H | —R¹ | —R³ | —R⁵ |
| 1'-7 | phenyl | —OCH₃ | —H | —R¹ | —R³ | —R⁵ |
| 1'-8 | 2-fluorophenyl | —OCH₃ | —H | —R¹ | —R³ | —R⁵ |
| 1'-9 | 2-methylphenyl | —OCH₃ | —H | —R¹ | —R³ | —R⁵ |
| 1'-10 | 4-(methoxycarbonyl)phenyl | —OCH₃ | —H | —R¹ | —R³ | —R⁵ |
| 1'-11 | 2,6-dimethylphenyl | —OCH₃ | —H | —R¹ | —R³ | —R⁵ |
| 1'-12 | 4-(n-propoxy)phenyl | —OCH₃ | —H | —R¹ | —R³ | —R⁵ |
| 1'-13 | 2-methoxyphenyl | —OCH₃ | —H | —R¹ | —R³ | —R⁵ |

-continued
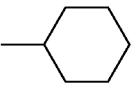
| No. | —R¹ | —R³ | —R⁵ | —R⁹ | —R¹¹ | —R¹³ |
|---|---|---|---|---|---|---|
| 1'-14 | 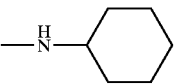 | —OCH₃ | —H | —R¹ | —R³ | —R⁵ |
| 1'-15 | —C₅H₁₁(n) | —OCH₃ | —H | —R¹ | —R³ | —R⁵ |
| 1'-16 | —CH=CH₂ | —OCH₃ | —H | —R¹ | —R³ | —R⁵ |
| 1'-17 | 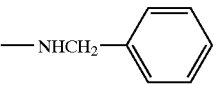 | —OCH₃ | —H | —R¹ | —R³ | —R⁵ |
| 1'-18 | —OC₆H₁₃(n) | —OCH₃ | —H | —R¹ | —R³ | —R⁵ |
| 1'-19 | 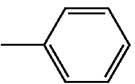 | —OCH₃ | —H | —R¹ | —R³ | —R⁵ |
| 1'-20 | 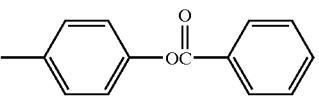 | —CH₃ | —H | —R¹ | —R³ | —R⁵ |
| 1'-21 | 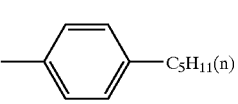 | —CH₃ | —H | —R¹ | —R³ | —R⁵ |
| 1'-22 | 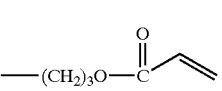 | —CH₃ | —H | —R¹ | —R³ | —R⁵ |
| 1'-23 | 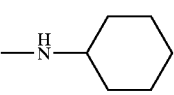 | —F | —H | —R¹ | —R³ | —R⁵ |
| 1'-24 | 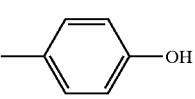 | —C₂H₅ | —H | —R¹ | —R³ | —R⁵ |
| 1'-25 | 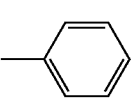 | —H | —OCH₃ | —R¹ | —R³ | —R⁵ |
| 1'-26 | 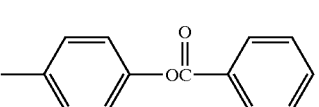 | —H | —OCH₃ | —R¹ | —R³ | —R⁵ |
| 1'-27 |  | —H | —OCH₃ | —R¹ | —R³ | —R⁵ |

-continued
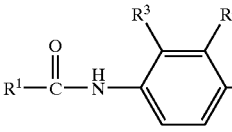
| No. | —R¹ | —R³ | —R⁵ | —R⁹ | —R¹¹ | —R¹³ |
|---|---|---|---|---|---|---|
| 1'-28 | 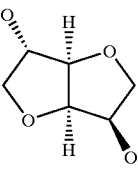 | —H | —OCH₃ | —R¹ | —R³ | —R⁵ |
| 1'-29 | 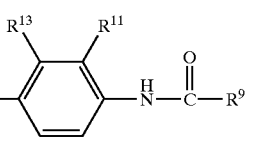 | —H | —OCH₃ | —R¹ | —R³ | —R⁵ |
| 1'-30 | 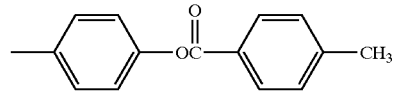 | —H | —OCH₃ | —R¹ | —R³ | —R⁵ |
| 1'-31 | 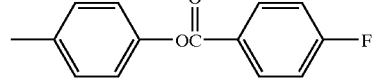 | —H | —OCH₃ | —R¹ | —R³ | —R⁵ |
| 1'-32 | 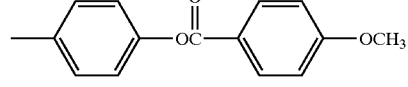 | —H | —OCH₃ | —R¹ | —R³ | —R⁵ |
| 1'-33 | 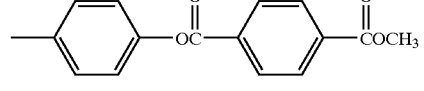 | —H | —OCH₃ | —R¹ | —R³ | —R⁵ |
| 1'-34 | 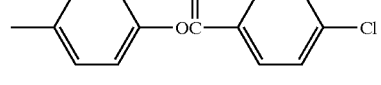 | —H | —OCH₃ | —R¹ | —R³ | —R⁵ |
| 1'-35 | —C₇H₁₅(n) | —H | —OCH₃ | —R¹ | —R³ | —R⁵ |
| 1'-36 | 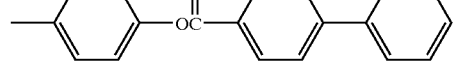 | —H | —OCH₃ | —R¹ | —R³ | —R⁵ |
| 1'-37 | 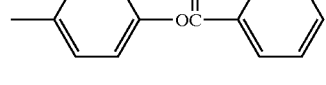 | —H | —OCH₃ | —R¹ | —R³ | —R⁵ |
| 1'-38 | 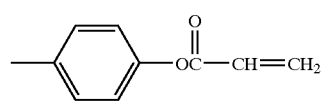 | —H | —OCH₃ | —R¹ | —R³ | —R⁵ |

-continued
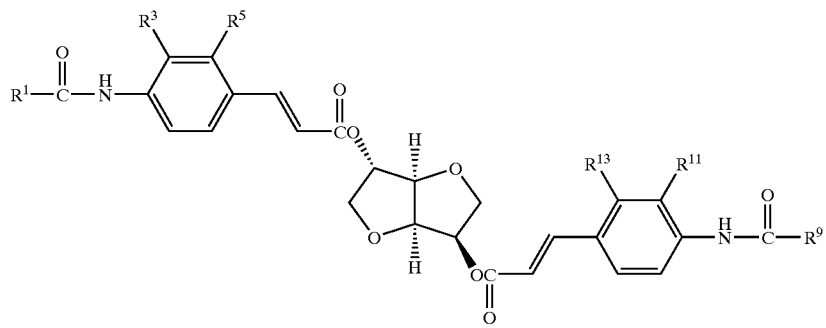
| No. | —R¹ | —R³ | —R⁵ | —R⁹ | —R¹¹ | —R¹³ |
|---|---|---|---|---|---|---|
| 1'-39 | —NH—CH₂—CH(C₂H₅)—C₄H₉ | —H | —OCH₃ | —R¹ | —R³ | —R⁵ |
| 1'-40 | —O—C₆H₅ | —H | —OCH₃ | —R¹ | —R³ | —R⁵ |
| 1'-41 | —C₆H₅ | —H | —CH₃ | —R¹ | —R³ | —R⁵ |
| 1'-42 | —C₆H₁₁ (cyclohexyl) | —H | —CH₃ | —R¹ | —R³ | —R⁵ |
| 1'-43 | —C₆H₄—C₆H₅ | —H | —Cl | —R¹ | —R³ | —R⁵ |
| 1'-44 | —C₆H₅ | —CH₃ | —CH₃ | —R¹ | —R³ | —R⁵ |
| 1'-45 | —C₆H₄—OC₂H₅ | —OCH₃ | —Cl | —R¹ | —R³ | —R⁵ |
| 1'-46 | —C₆H₄—CH₃ | —OCH₃ | —H | —C₆H₄—C₆H₁₃(n) | —OCH₃ | —H |
| 1'-47 | —C₆H₄—CH=CH₂ | —OCH₃ | —H | —C₆H₄—CH=CH₂ | —H | —H |
| 1'-48 | —C₆H₄—C₂H₅ | —OCH₃ | —H | —C₆H₄—OCH₃ | —H | —H |
| 1'-49 | —C₆H₄—COCH₃ | —Cl | —OCH₃ | —C₆H₄—COCH₃ | —H | —OCH₃ |

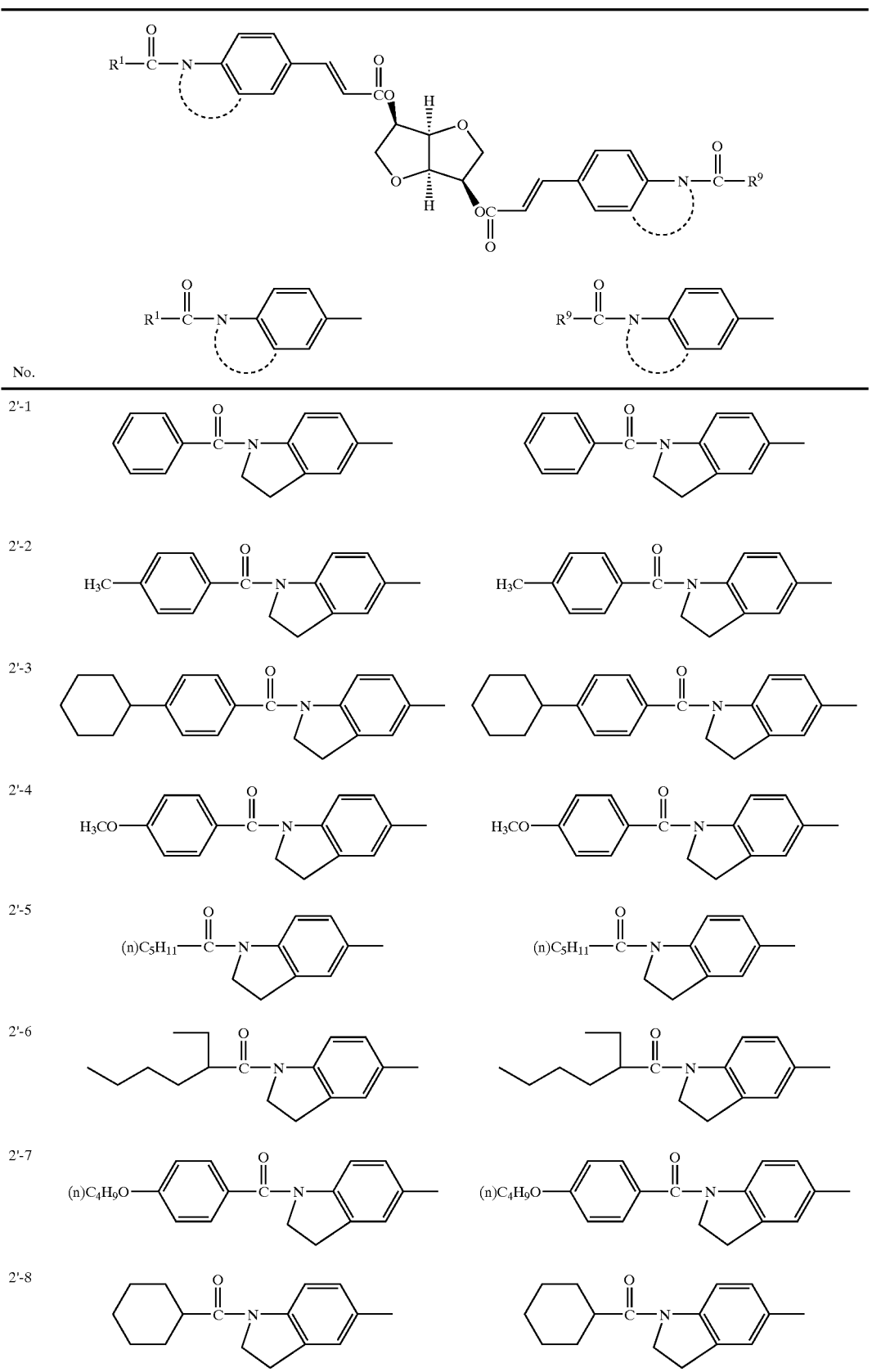

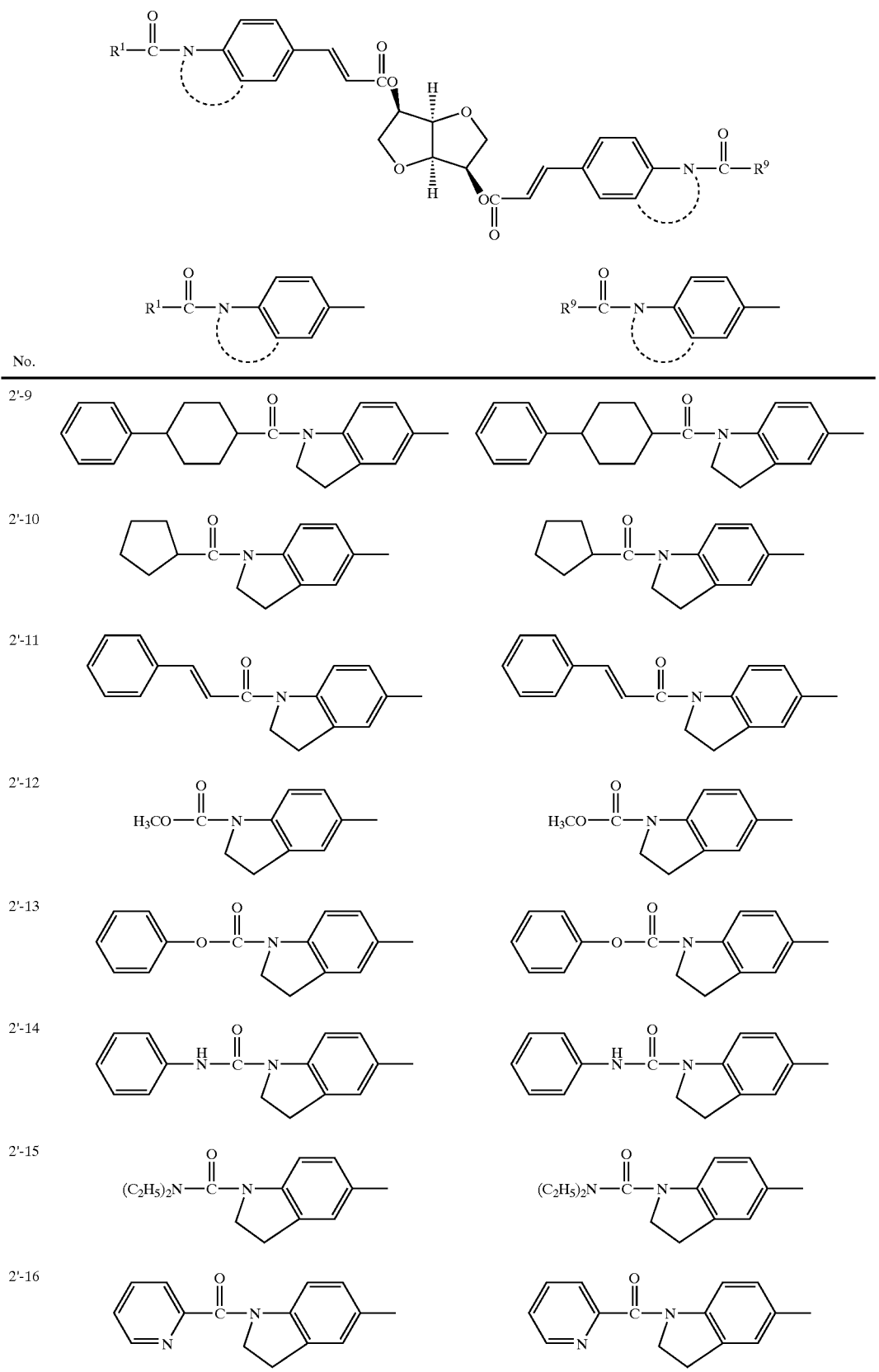

-continued
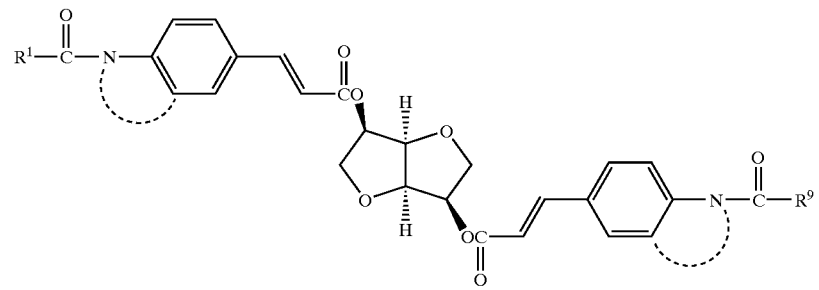
| No. | 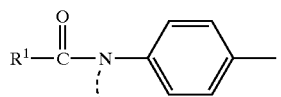 | 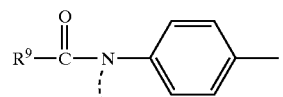 |
|---|---|---|
| 2'-17 | 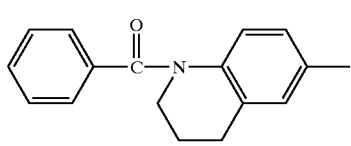 | 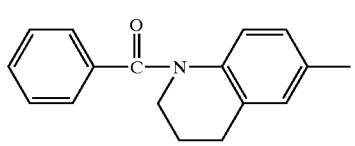 |
| 2'-18 | 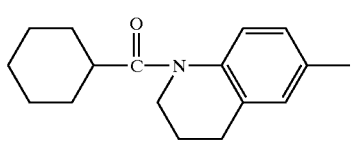 | 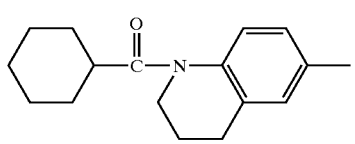 |
| 2'-19 | 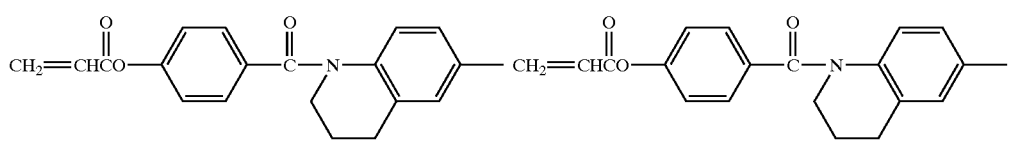 | |
| 2'-20 | 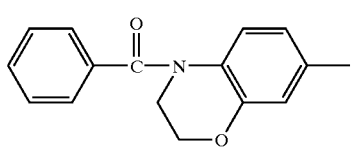 | 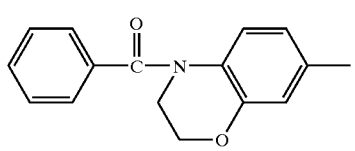 |
| 2'-21 | 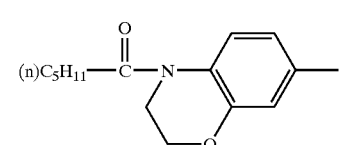 | 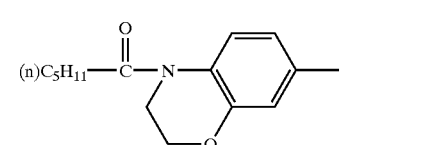 |
| 2'-22 | 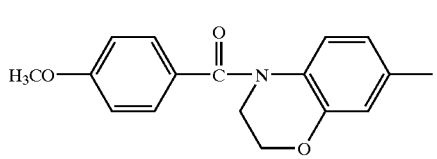 | 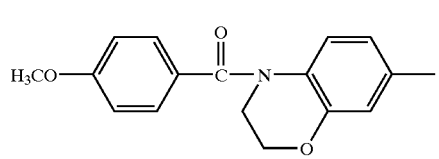 |
| 2'-23 | 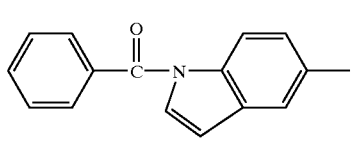 | 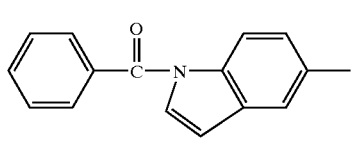 |

-continued
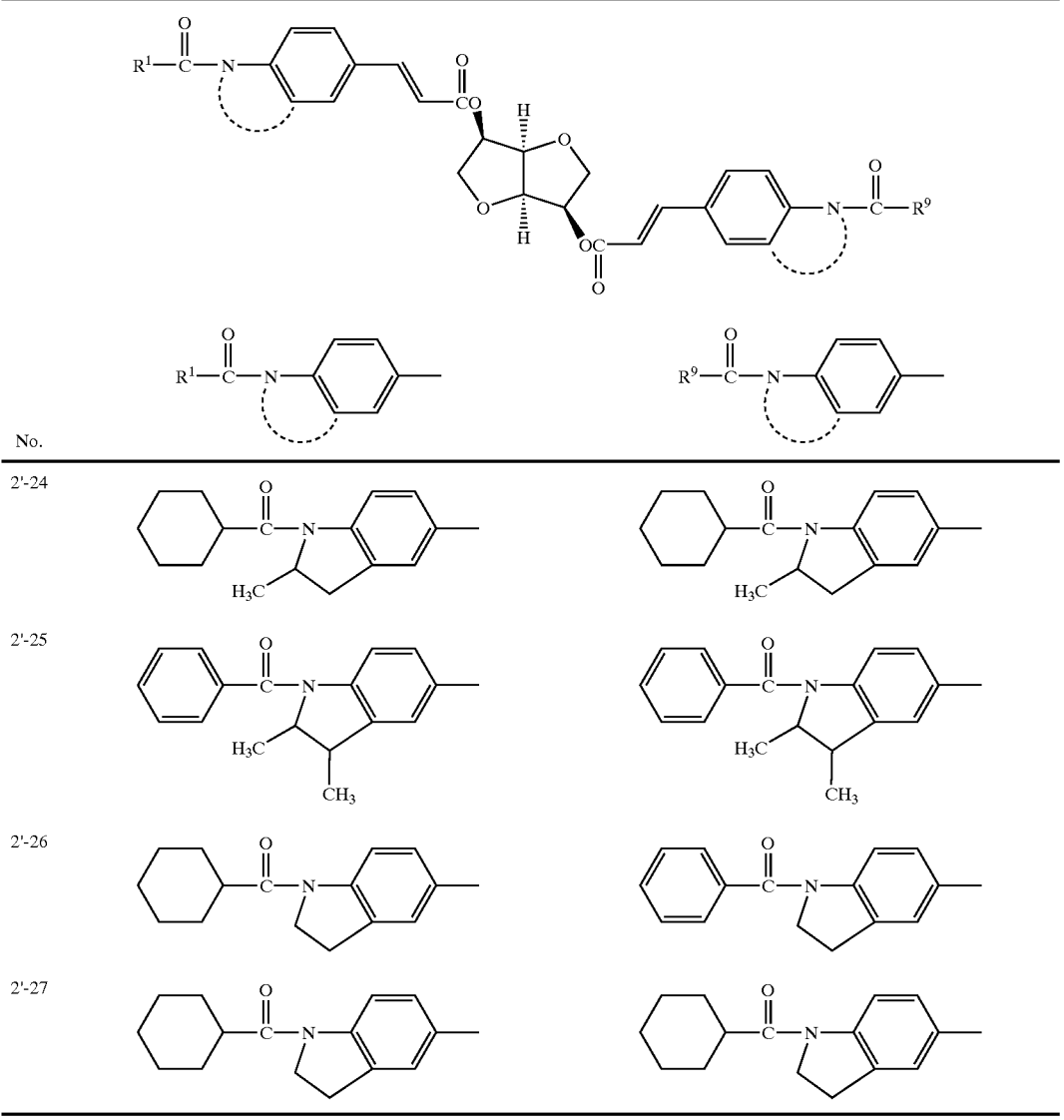
| No. | $-R^3$ | $-R^4$ | $-R^5$ | $-R^6$ | $-R^{11}$ | $-R^{12}$ | $-R^{13}$ | $-R^{14}$ |
|---|---|---|---|---|---|---|---|---|
| 3'-1 | $-OCH_3$ | $-OCH_3$ | $-H$ | $-H$ | $-OCH_3$ | $-OCH_3$ | $-H$ | $-H$ |
| 3'-2 | $-OCH_3$ | $-H$ | $-H$ | $-CH_3$ | $-OCH_3$ | $-H$ | $-H$ | $-CH_3$ |
| 3'-3 | $-OCH_3$ | $-H$ | $-H$ | $-Cl$ | $-OCH_3$ | $-H$ | $-H$ | $-Cl$ |
| 3'-4 | $-CH_3$ | $-H$ | $-H$ | $-Cl$ | $-CH_3$ | $-H$ | $-H$ | $-Cl$ |

-continued
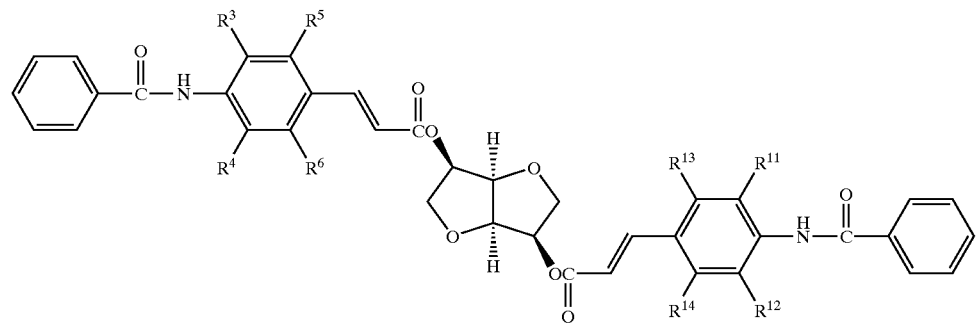
| No. | —R³ | —R⁴ | —R⁵ | —R⁶ | —R¹¹ | —R¹² | —R¹³ | —R¹⁴ |
|---|---|---|---|---|---|---|---|---|
| 3'-5 | —CH₃ | —CH₃ | —H | —H | —CH₃ | —CH₃ | —H | —H |
| 3'-6 | —F | —F | —H | —H | —F | —F | —H | —H |
| 3'-7 | —CH₃ | —CH₃ | —H | —H | —CH₃ | —H | —H | —H |
| No. | —R² | —R⁴ | —R³ | —R⁵ | —R⁶ | —R¹⁰ | —R¹² | —R¹¹ | —R¹³ | —R¹⁴ |
|---|---|---|---|---|---|---|---|---|---|---|
| 4'-1 | —CH₃ | —H | —H | —H | —H | —CH₃ | —H | —H | —H | —H |
| 4'-2 | —CH₂CH₂— | | —Cl | —H | —H | —CH₂CH₂— | | —Cl | —H | —H |
| 4'-3 | —C₆H₅ | —H | —H | —H | —H | —C₆H₅ | —H | —H | —H | —H |
| 4'-4 | —CH₂CH₂— | | —H | —H | —CH₃ | —CH₂CH₂— | | —H | —H | —H |
No. 5'-1
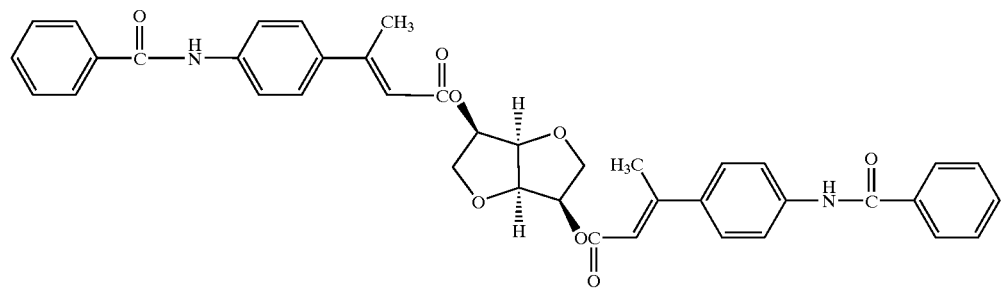
No. 5'-2
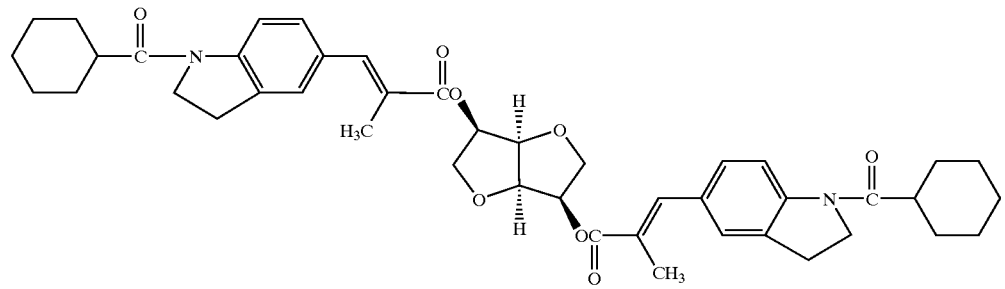

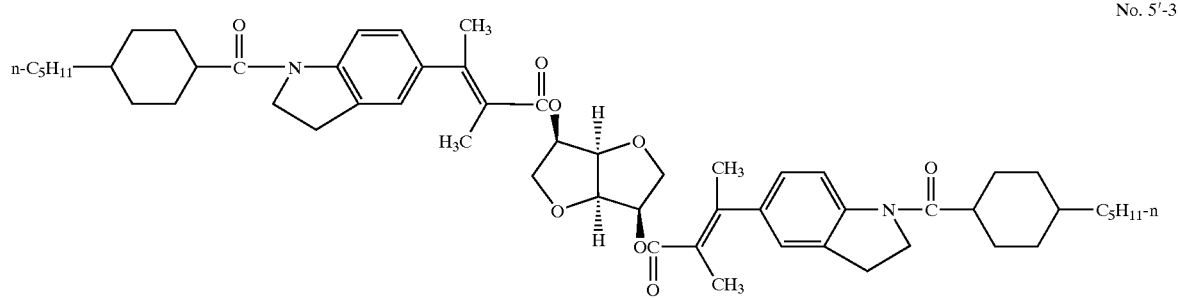

No. 5'-3

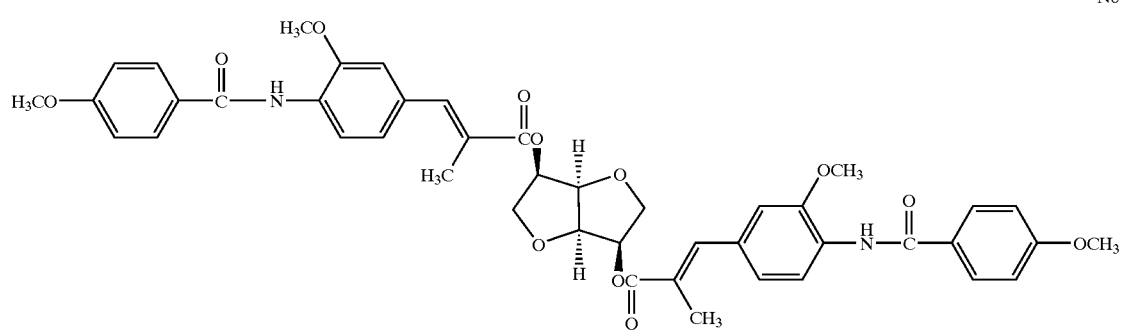

No. 5'-4

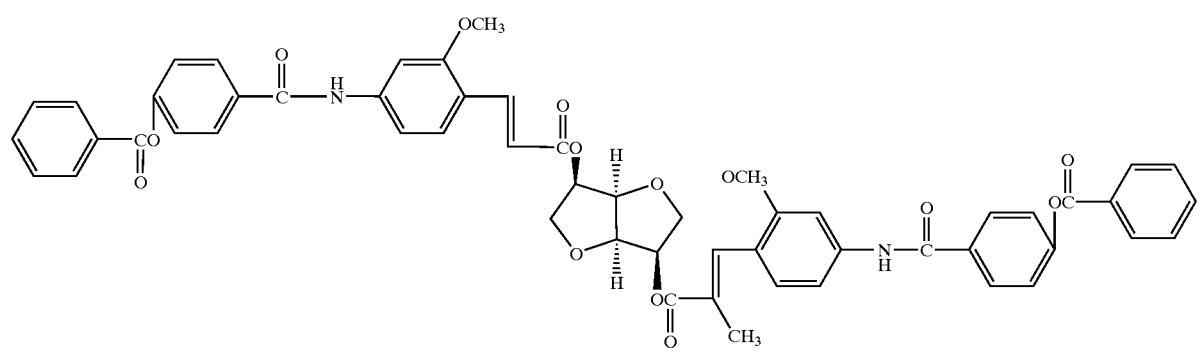

No. 5'-5

Syntheses of Isosorbide Derivative and Isomannide Derivative

Next, synthesis methods of the optically active isosorbide derivative as represented by the general formula (I) according to the invention and the optically active isomannide derivative as represented by the general formula (V) according to the invention will be described in detail below.

Synthesis of the optically active isosorbide derivative as represented by the general formula (I) and the optically active isomannide derivative as represented by the general formula (V) can be performed by a method (1) in which an isosorbide and a corresponding carboxylic acid chloride or an isomannide and a corresponding carboxylic acid chloride are esterified therebetween under a basic condition, a method (2) in which an isosorbide and a corresponding carboxylic acid or an isomannide and a corresponding carboxylic acid are condensed therebetween by using a dehydrating agent such as DCC, or a method (3) in which a Mitsunobu reaction is performed between an isosorbide and a corresponding carboxylic acid or an isomannide and a corresponding carboxylic acid.

The corresponding carboxylic acid chloride can be obtained by allowing a carboxylic acid and oxalyl chloride, thionyl chloride or the like to react with each other. Further, the corresponding carboxylic acid can be obtained by a knaevenagel reaction of a corresponding arylaldehyde and a malonic acid, a method in which a Wittig reaction of the corresponding arylaldehyde and carbomethoxymethylene triphenylphosphoran is performed and, then, the resultant reaction product is hydrolyzed, a method in which a Heck reaction of a corresponding aryl halide such as a corresponding aryl bromide and acrylic acid or an acrylic acid ester is performed or any other appropriate method.

Further, the optically active isosorbide derivative and the optically active isomannide derivative can also be produced by following reaction formulae, respectively:

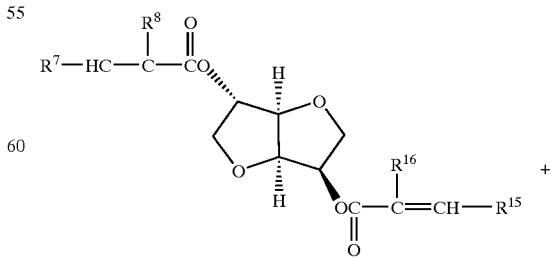

General formula (IV)

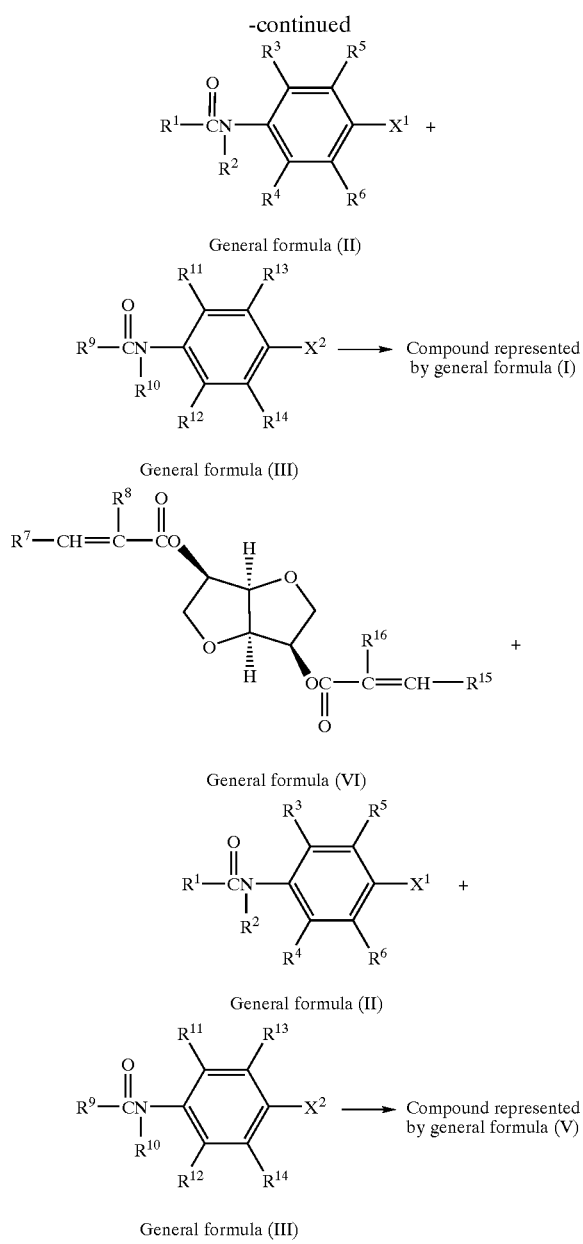

wherein, $X^1$, particularly in the general formula (II), and $X^2$, particularly in the general formula (III), each independently represent a halogen and, among other atoms, a bromine atom or an iodine atom is preferable and, therebetween, the iodine atom is particularly preferable.

In other words, the isosorbide derivative as represented by the general formula (I) and the isomannide derivative as represented by the general formula (V) can each be synthesized by a coupling reaction of aryl halides and an olefin.

In order to accelerate the coupling reaction, it is preferable that the coupling reaction is allowed to occur while a transition metal catalyst, a base, a solvent and, optionally, other additives are simultaneously present. Further, as for details of the coupling reaction, methods and the like described in "Organic Reactions"<27>, 345 (1982) can be employed.

The compounds as represented by the general formulae (II) and (III) are preferably used, based on compounds as represented by the general formula (IV) and (VI), in a quantity of from 1.0 molar equivalent to 5.0 molar equivalent, respectively and particularly preferably in a quantity of from 1.0 molar equivalent to 2.0 molar equivalent, respectively.

As for such transition metal catalysts, a palladium catalyst and a nickel catalyst are preferable and, therebetween, the palladium catalyst is particularly preferable.

As for such palladium catalysts, either a so-called zero-valent palladium catalyst or a bivalent palladium catalyst is permissible; specific examples thereof include $Pd(PPh_3)_4$, bis(dibenzylidene acetone)palladium (0), $Pd(OAc)_2$, $PdCl_2$ and $PdCl_2(PPh_3)_2$.

When the palladium catalyst is used as the transition metal catalyst, a quantity thereof to be added is, based on the compound as represented by the general formula (IV) or (VI), preferably from 0.005 molar equivalent to 0.3 molar equivalent and particularly preferably from 0.01 molar equivalent to 0.2 molar equivalent.

As for such bases, either an inorganic base or an organic base is permissible; specific examples thereof include calcium carbonate, triethyl amine, tributyl amine and potassium acetate. Further a quantity thereof to be added is, based on the compound as represented by the general formula (IV) or (VI), preferably from 2.0 molar equivalent to 10.0 molar equivalent and particularly preferably from 2.0 molar equivalent to 5.0 molar equivalent.

As for such solvents, DMF (dimethyl formamide), DMAc (dimethyl acetamide), acetonitrile and toluene are preferable and, thereamong, DMF and toluene are particularly preferable. Further, a quantity of the solvent to be added is, against 1 mol of the compound as represented by the general formula (IV) or (VI), preferably from 1.0 L to 10 L and particularly preferably from 1.0 L to 5.0 L.

As for the other additives, phosphine-type ligands, such as triphehylphosphine, tributylphosphine, 1,2-bis(diphenylphosphino)ethane, 1,3-bis(diphenylphosphino)propane, 1,4-bis(diphenylphosphino)butane, 1,1'-bis(diphenylphosphino)ferrocene and 2,2'-bis(diphenylphosphino)-1,1'-binaphthyl; quaternary ammonium salts such as tetrabutyl ammonium bromide and tetrabutyl ammonium chloride; and metallic salts such as silver nitrate can be used.

It is preferable that a quantity of the other additives to be added is appropriately adjusted in accordance with respective functions thereof. For example, in a case of the phosphine-type ligands, the quantity thereof is, based on the compound as represented by the general formula (IV) or (VI), preferably from 0.01 molar equivalent to 0.4 molar equivalent and particularly preferably from 0.05 molar equivalent to 0.3 molar equivalent.

Further, in a case of the quaternary ammonium salts, a quantity thereof to be added is, based on the compound as represented by the general formula (IV) or (VI), preferably from 1.0 molar equivalent to 5.0 molar equivalent and particularly preferably from 2.0 molar equivalent to 4.0 molar equivalent.

In a case of the metallic salts, a quantity thereof to be added is, based on the compound as represented by the general formula (IV) or (VI), preferably from 1.0 molar equivalent to 5.0 molar equivalent and particularly preferably from 2.0 molar equivalent to 4.0 molar equivalent.

Further, a reaction temperature is preferably from 20° C. to 200° C. and particularly preferably from 50° C. to 120° C.

Still further, when $R^2$ and $R^{10}$ in the general formula (I) or (V) each independently represent a hydrogen atom, the optically active isosorbide derivative and the optically active isomannide derivative can be synthesized by the following reaction formulae, respectively:

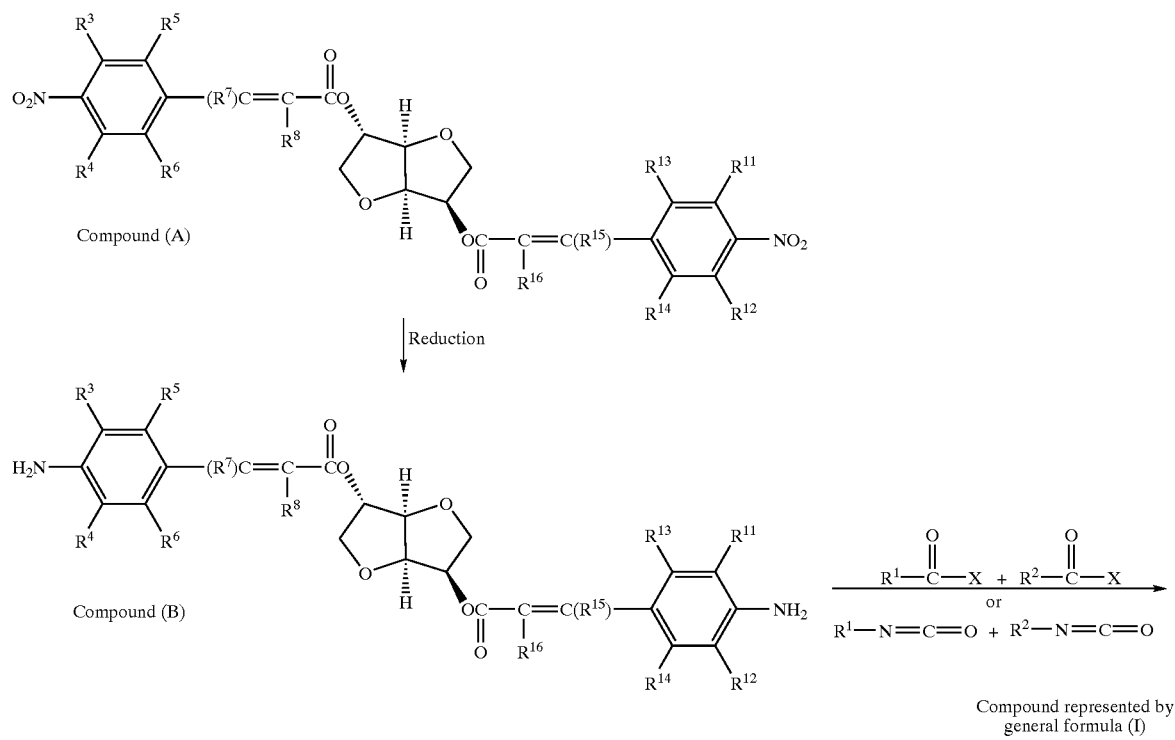

X represents a chlorine atom or hydroxyl group

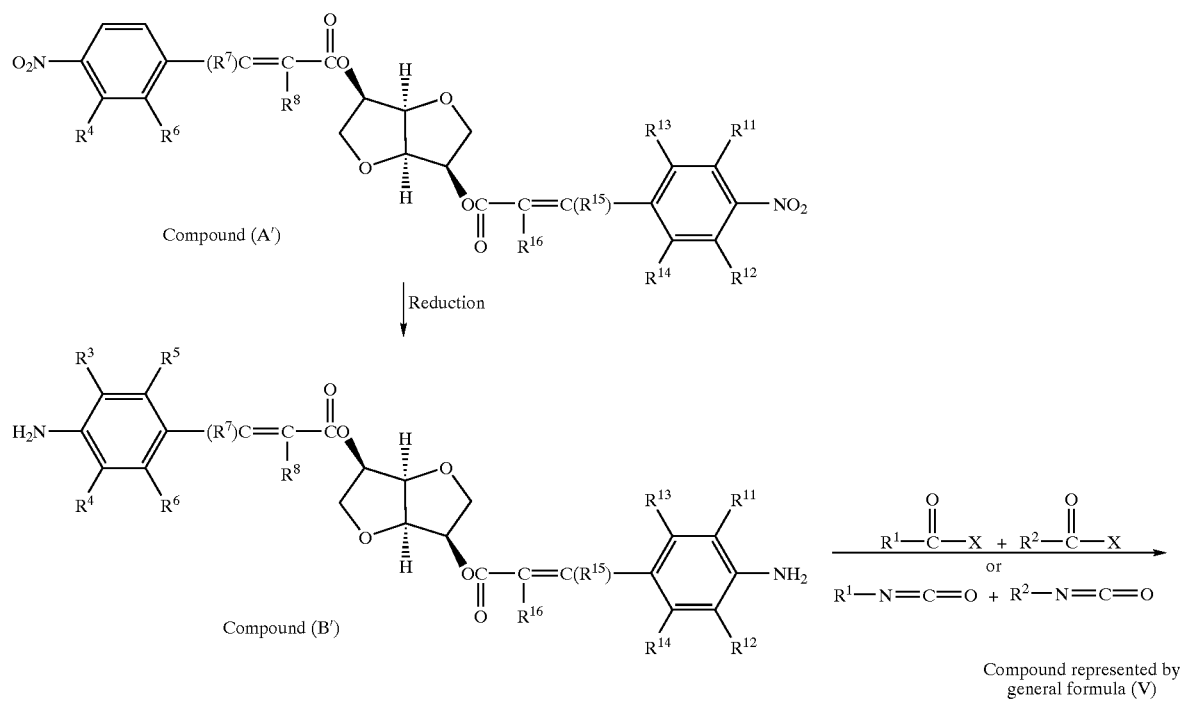

X represents a chlorine atom or hydroxyl group

Namely, after a compound (A) is obtained by the above-described method, an amino form (B) is obtained by reducing a nitro group therein. Whereas, after a compound (A') is obtained by the above-described method, an amino form (B') is obtained by reducing an nitro group therein. Such reduction reaction can utilize a known reduction method which uses iron powders, zinc or the like. The compound as represented by the general formula (I) can be synthesized by a method (1) in which the compound (B) and a corresponding acid chloride are allowed to react with each other under a basic condition, a method (2) in which the compound (B) and a corresponding carboxylic acid are condensed therebetween by using a dehydrating agent such as DCC, a method (3) in which the compound (B) and a corresponding isocyanate are allowed to react with each other or other appropriate methods. The compound as represented by the general formula (V) can also be synthesized by a method (1) in which the compound (B') and a corresponding acid chloride are allowed to react with each other under a basic condition, a method (2) in which the compound (B') and a corresponding carboxylic acid are condensed therebetween by using a dehydrating agent such as DCC, a method (3) in which the compound (B') and a corresponding isocyanate are allowed to react with each other or other appropriate methods.

Further, the compound as represented by the general formula (I) which has been synthesized by the above-described method can subsequently be subjected to a functional group change such as acylation or esterification, thereby leading to another compound also as represented by the general formula (I). In the same manner, the compound as represented by the general formula (V) can be led to another compound also as represented by the general formula (V).

Photo-Reactive Chiral Agent

The photo-reactive chiral agent according to the invention comprising the above-described optically active isosorbide derivative or the above-described optically active isomannide derivative has characteristics in which not only the orientation structure of the liquid crystalline compound can be controlled, but also the liquid crystalline compound is subjected to structural isomerization by the irradiation of light to allow a helical pitch of the liquid crystal, namely, helical twisting power (HTP) of the helical structure to be changed. That is, the photo-reactive chiral compound is such a compound as can cause, by irradiation of light (from ultraviolet ray to visible light ray to infrared ray), the change of the helical twisting power (hereinafter also referred to as "HTP" in short) of the helical structure which is induced in the liquid crystalline compound or, preferably, a nematic liquid crystal compound whereupon the photo-reactive chiral compound comprises, as required portions (molecular structure units), a chiral portion and a portion which causes the structural change by light irradiation.

Further, the photo-reactive chiral agent comprising the optically active isosorbide derivative or the optically active isomannide derivative can substantially change the HTP of, particularly, a liquid crystal molecule. Therefore, for example, in a case of a cholesteric liquid crystal (liquid crystal phase) in which the nematic liquid crystal compound is used as a liquid crystalline compound, selective reflection in a wide range of wavelength region comprising three primary colors, that is, B (blue), G (green) and R (red), can be realized. Namely, selective reflection characteristics of the wavelength of light is determined in accordance with the helical twisting angle of the helical structure of the liquid crystal molecule whereupon, as the angle thereof is larger, color width which is selectively reflected becomes larger; this feature is useful.

Still further, when the photo-reactive chiral agent comprising the optically active isosorbide derivative or the optically active isomannide derivative has a structure in which one or more polymerizable connecting groups are introduced in one molecule thereof, thermal resistance of the liquid crystal composition comprising the photo-reactive chiral compound, for example, a liquid crystal color filter and an optical film can be enhanced.

A molecular weight of the isosorbide derivative or the isomannide derivative is preferably 500 or more. Further, it is preferable that solubility of the isosorbide derivative or the isomannide derivative to the liquid crystalline compound to be described below is high whereupon a solubility parameter (SP) value thereof is preferably approximate to that of the liquid crystalline compound.

Furthermore, the above-described HTP shows the helical twisting power of the helical structure of the liquid crystal, namely, HTP=1/[pitch×chiral agent concentration (mass fraction)] and, for example, is determined by first measuring the helical pitch (one cycle of the helical structure: $\mu$m) of the liquid crystal molecule at a given temperature and, then, converting (in terms of $\mu m^{-1}$) the resulting value based on the chiral agent concentration.

When the selectively reflected color is formed in accordance with light irradiation by the photo-reactive chiral agent, a change ratio of the HTP (=HTP before light irradiation/HTP after light irradiation) is, in a case in which the HTP becomes smaller after the light irradiation, preferably 1.5 or more and more preferably 2.5 or more and is, in a case in which the HTP becomes larger after the light irradiation, preferably 0.7 or less and more preferably 0.4 or less.

Further, the photo-reactive chiral agent according to the invention can be used together with a known non-photo-reactive chiral agent such as that having the helical twisting power which largely depends on temperature.

Examples of such known non-photo-reactive chiral agents include chiral agents described in JP-A No. 2000-44451, WO 96/17901, WO 98/00428, WO 97/34886 and WO 95/16007, "Liquid Crystals"<21>, 327 (1996), "Liquid Crystals"<24>, 219 (1998) and the like.

Liquid Crystal Composition

The liquid crystal composition according to the invention comprises at least one type of liquid crystalline compound (preferably nematic liquid crystal compound) and at least one type selected from the group consisting of optically active isosorbide derivatives (namely, photo-reactive chiral agents) according to the invention, or comprises at least one type of liquid crystalline compound (preferably nematic liquid crystal compound) and at least one type selected from the group consisting of optically active isomannide derivatives (namely, photo-reactive chiral agents according to the invention) whereupon the liquid crystalline compound may or may not contain a polymerizable group.

Further, the liquid crystal composition according to the invention may optionally contain a polymerizable monomer, a polymerization initiator and other components such as a binder resin, a solvent, a surfactant, a polymerization inhibitor, a thickener, a coloring agent, a pigment, an ultraviolet ray absorbing agent, a gelling agent and the like. It is preferable that the liquid crystal composition according to the invention simultaneously contains, particularly, the surfactant. By simultaneously containing the surfactant therein, for example, in a case in which the liquid crystal composition in a coating solution state is applied to form a layer, the orientation state of the liquid crystal molecule on a layer surface at the air interface thereof can be controlled in a three-dimensional manner and, particularly in a case of a cholesteric liquid crystal phase, selective reflection wavelength which is higher in color purity can be obtained.

Optically Active Isosorbide Derivative and Optically Active Isomannide Derivative The above-described optically active isosorbide derivative contains the optically active isosorbide derivative as represented by the general formula (I) as a photo-reactive chiral agent while the above-described optically active isomannide derivative contains the optically active isomannide derivative as represented by the general formula (V) as a photo-reactive chiral agent whereupon, in each of such cases, not only the orientation structure of the liquid crystal molecule can be controlled in a three-dimensional manner, but also the helical structure of the coexistent liquid crystalline compound, preferably, a nematic liquid crystal compound, is allowed to be changed by irradiating light having a desired pattern and a desired light quantity.

A quantity of the above-described optically active isosorbide derivative (photo-reactive chiral agent) or the above-described optically active isomannide derivative (photo-reactive chiral agent) to be contained can be selected without any restriction but is, based on the entire solid content of the liquid crystal composition (in terms of mass), preferably from about 0.1% by mass to about 30% by mass.

Liquid Crystalline Compound

The liquid crystalline compound can appropriately be selected from the group consisting of: a liquid crystal compound having a refraction index anisotropy $\Delta n$ of from 0.10 to 0.40, a polymer liquid crystal compound and a polymeric liquid crystal compound. For example, a smectic liquid crystal compound and a nematic liquid crystal compound can be mentioned. Therebetween, the nematic liquid crystal compound is preferable. For example, the cholesteric liquid crystal composition (cholesteric liquid crystal phase) can be prepared by using the nematic liquid crystal compound as the liquid crystalline compound and simultaneously employing the optically active isosorbide derivative as represented by the general formula (I) in the liquid crystalline compound, or by using the nematic liquid crystal compound as the liquid crystalline compound and simultaneously employing the optically active isomannide derivative as represented by the general formula (V) in the liquid crystalline compound.

The liquid crystalline compound can be oriented by using an oriented substrate which has been subjected to an orientation treatment, for example, a rubbing treatment while the liquid crystalline compound is in a liquid crystalline state at the time of melting. Further, when the liquid crystalline state is fixed to be a solid phase, a device for cooling, polymerization or the like can be used.

Specific examples of the liquid crystalline compounds include such compounds as described in WO 95/22586, Japanese Patent Application Nos. 2000-51089, 2000-68479 and 11-91162. However, these compounds should not be interpreted as limiting the invention in any way. Some of these liquid crystalline compounds are illustrated as follows:

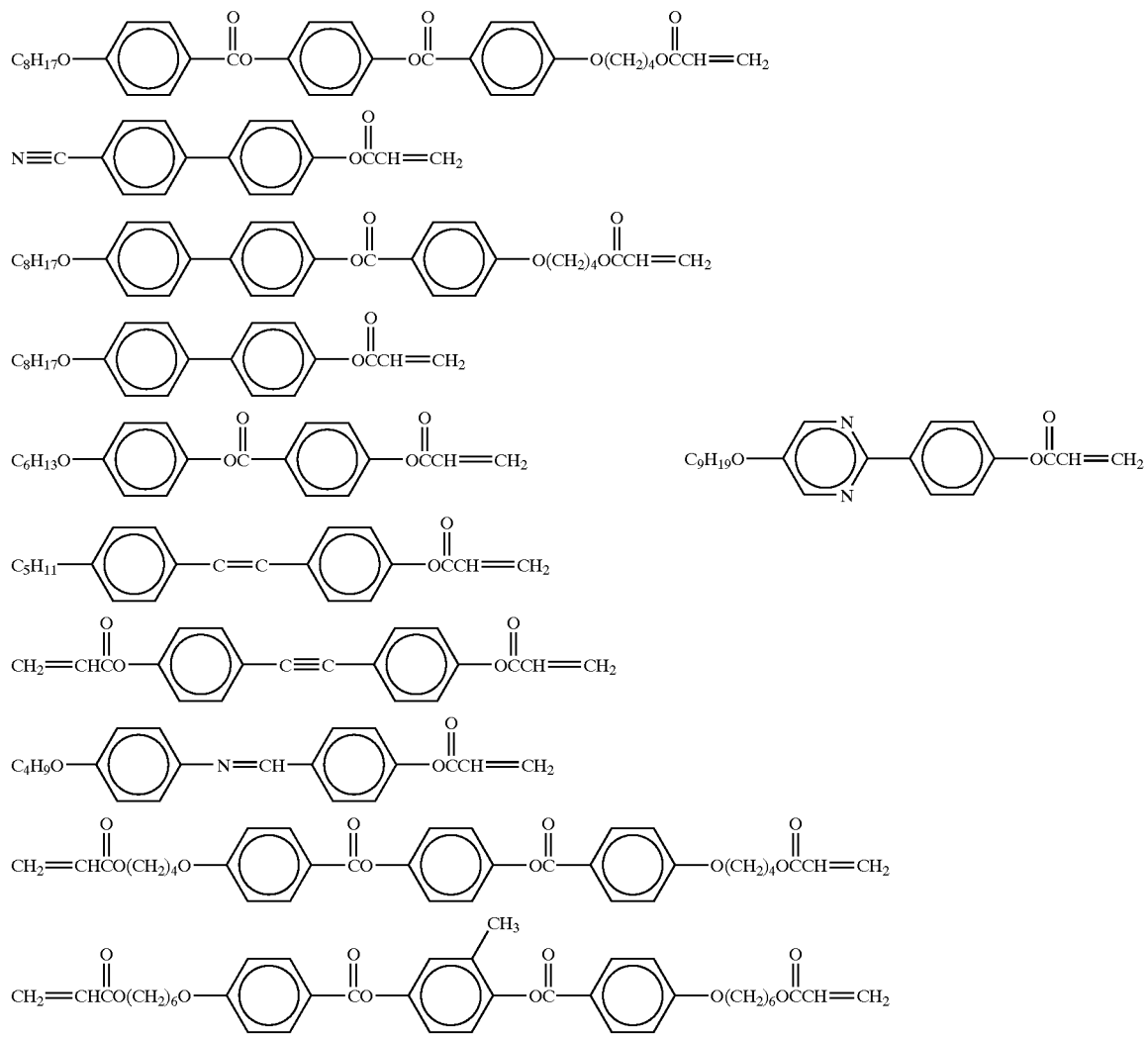

-continued

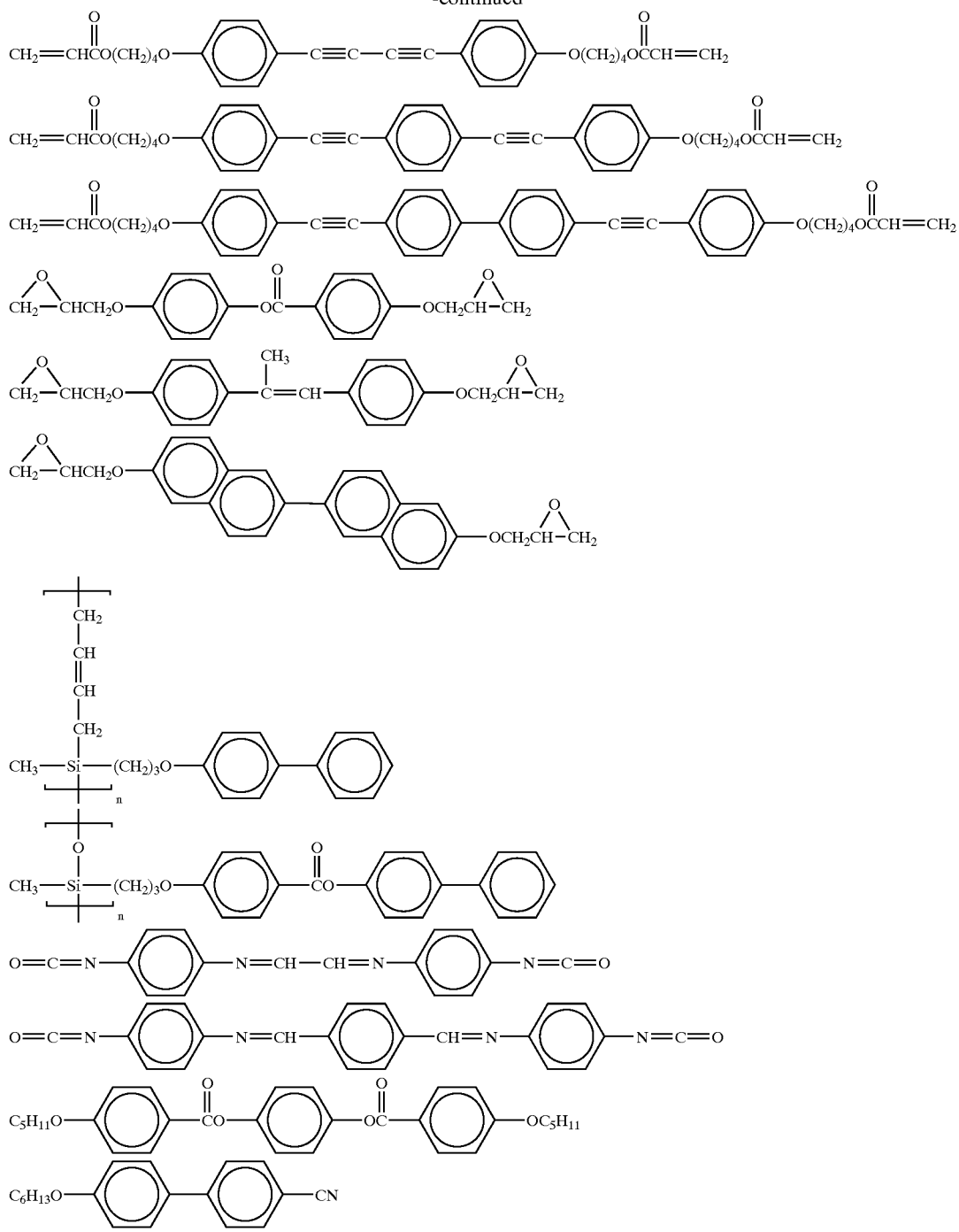

In the above-described chemical formulae, n represents an integer of from 1 to 1000.

In such illustrative compounds, those in which a connecting group of an aromatic ring is changed into any one of structures described below are also favorable.

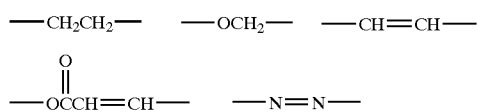

-continued

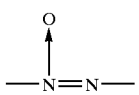

Thereamong, from the standpoint of securing a sufficient hardening property and enhancing thermal resistance of a layer, a liquid crystalline compound having a polymerizable group or a cross-linking group in a molecule is favorable.

A quantity of the liquid crystalline compound to be contained is, based on the entire solid content (by mass) of the liquid crystal composition, preferably from 30% by mass to 99.9% by mass and more preferably from 50% by mass to 95% by mass.

Photo-Polymerization Initiator

The liquid crystal composition according to the invention may contain a photo-polymerization initiator whereupon, by simultaneously using the photo-polymerization initiator, a polymerization reaction of a polymerizable group is promoted and the helical structure of the liquid crystal to be generated after the helical pitch (helical twisting power) of the liquid crystal is changed by light irradiation is fixed, thereby being capable of enhancing strength of the thus-fixed liquid crystal composition. When the polymerization reaction depending on the polymerizable liquid crystalline compound is utilized in fixing the helical structure of the liquid crystal, it is preferable that the photo-polymerization initiator is added thereto.

For example, when the liquid crystal phase is the cholesteric liquid crystal phase, the desired helical pitch can consistently be obtained to secure the selectively reflected color of high purity.

As for such photo-polymerization initiators, any type of known photo-polymerization initiators can appropriately be selected. Examples of the photo-polymerization initiators include p-methoxyphenyl-2,4-bis(trichloromethyl)-s-triazine, 2-(p-butoxystyryl)-5-trichloromethyl-1,3,4-oxadiazol, 9-phenylacrydine, 9,10-dimethylbenzphenazine, benzophenone/Michler's ketone, hexaarylbiimidazol/mercaptobenzimidazol, benzyl dimethyl ketal, thioxanthone/amine and triarylsulfonium hexafluorophosphate. Examples thereof further include bisacyl phosphine oxides, such as a bis-(2,4,6-trimethylbenzoyl)-phenylphosphine oxide, disclosed in JP-A No. 10-29997 and acylphosphine oxides, such as Lucirin TPO, disclosed in DE4230555.

A quantity of the photo-polymerization initiator to be added is, based on the entire solid contents (by mass) of the liquid crystal composition, preferably from 0.1% by mass to 20% by mass and more preferably 0.5% by mass to 5% by mass.

As described above, in the liquid crystal composition according to the invention, the optically active isosorbide derivative as represented by the general formula (I) and the photo-polymerization initiator, or the optically active isomannide derivative as represented by the general formula (V) and the photo-polymerization initiator are simultaneously contained whereupon the optically active isosorbide derivative or the optically active isomannide derivative is isomerized (trans-cis) by light to allow the helical pitch of the liquid crystal to be changed while the photo-polymerization initiator can promote the polymerization reaction of the polymerizable group by light; therefore, it is preferable that the optically active isosorbide derivative or the optically active isomannide derivative and the photo-polymerization initiator have different photosensitive wavelength regions from one the other against a light source wavelength. The term "having different photosensitive wavelength regions" as used herein is intended to mean that photosensitive central wavelengths of both compounds are not overlapped with each other whereupon, for example, the liquid crystal orientations thereof are not interfered at the time of imagewise exposure or hardening due to the other factor to such an extent as does not cause deterioration of display characteristics of the image or selectively reflected hue purity. Such overlapping of the photosensitive central wavelengths can be prevented by appropriately selecting the molecular structures of both compounds, and also by controlling a wavelength of an irradiation light by allowing it to pass through a band pass filter or the like.

Since they are sensitive to the light having different wavelength from each other, the liquid crystal composition according to the invention is imagewise irradiated whereupon the liquid crystal molecule therein is oriented in a pattern state and, then, fixed without giving any detrimental effect on the helical pitch of the liquid crystal in which the liquid crystal molecule is thus oriented in the pattern state. For example, when the liquid crystal phase is a cholesteric liquid crystal phase, the selectively reflected color based on the desired helical pitch can be displayed and the hue of excellent color purity can be obtained.

Polymerizable Monomer

In the liquid crystal composition according to the invention, for the purpose of enhancing an extent of hardening of, for example, film strength, a polymerizable monomer may simultaneously be used. When the polymerizable monomer is simultaneously used, after the helical twisting power is subjected to a change (patterning) (for example, after a distribution of selective reflection wavelength is formed), the resultant helical structure (selective reflection property) is fixed whereupon strength of the liquid crystal composition after being fixed can be further enhanced. However, when the liquid crystalline compound has the polymerizable group in a same molecule, it is not necessary to add the polymerizable monomer therein.

As an example of the polymerizable monomer, mentioned is a monomer having an ethylenically unsaturated bond. Specific examples of such monomers include multi-functional monomers such as pentaerythritol tetraacrylate and dipentaerythritol hexaacrylate.

As specific examples of the monomers each having the ethylenically unsaturated bond, following compounds are illustrated, although the invention is by no means limited thereto:

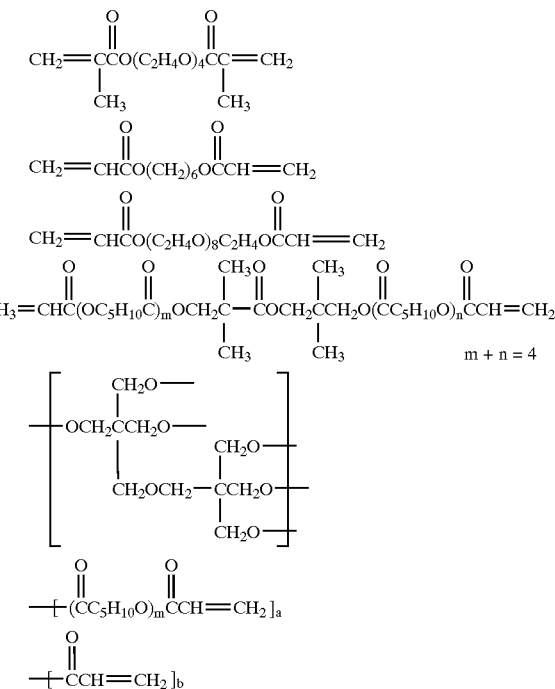

-continued

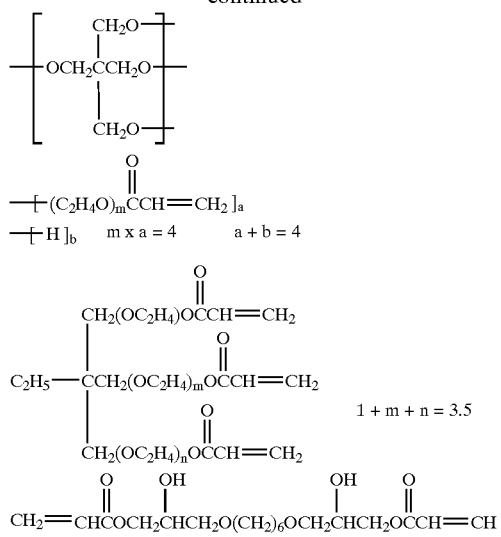

A quantity of the polymerizable monomer to be added is, based on the entire solid contents (by mass) of the liquid crystal composition, preferably from 0.5% by mass to 50% by mass.

Other Components

Further, other components such as a binder resin, a solvent, a surfactant, a polymerization inhibitor, a thickener, a coloring agent, a pigment, an ultraviolet ray absorbing agent and a gelling agent may be added.

Examples of such binder resins include polystyrene compounds such as polystyrene and poly-α-methylstyrene; cellulose resins such as methyl cellulose, ethyl cellulose and acetyl cellulose; acidic cellulose derivatives having a carboxyl group in a side chain; acetal resins, such as polyvinyl formal and polyvinyl butyral; methacrylic acid copolymers, acrylic acid copolymers, itaconic acid copolymers, crotonic acid copolymers, maleic acid copolymers and partially esterified maleic acid copolymers disclosed in JP-A No. 59-44615, JP-B Nos. 54-34327, 58-12577, 54-25957, JP-A Nos. 59-53836 and 59-71048.

As further examples thereof, homopolymers of an alkyl acrylate and homopolymers of an alkyl methacrylate are mentioned. Examples of such alkyl groups in these homopolymers include a methyl group, an ethyl group, an n-propyl group, an n-butyl group, an isobutyl group, an n-hexyl group, a cyclohexyl group and a 2-ethylhexyl group.

As still further examples thereof, mentioned are a polymer in which an acid anhydride is added to a polymer having a hydroxyl group, a benzyl(meth)acrylate/acrylic acid copolymer, multi-component copolymers such as a benzyl (meth)acylate/(meth)acrylic acid/another monomer and the like.

A quantity of the binder resin to be contained in the liquid crystal composition is preferably from 0% by weight to 50% by weight and more preferably from 0% by weight to 30% by weight.

In a liquid crystal composition of the present invention, it is preferable to use a surfactant together with a photo-reactive chiral agent and a liquid crystalline compound. As the surfactant, a surfactant having an excluded volume effect is preferable. The term "have an excluded volume effect" as used herein is intended to mean a three-dimensional control of the spatial orientation state of the layer surface at the air interface thereof at the time of, for example, forming a layer containing the liquid crystal composition by coating.

Specifically, a nonionic surfactant is preferable, whereupon it can appropriately be selected from known nonionic surfactants.

The polymerization inhibitor can be added for the purpose of improving a storage property. Examples of such polymerization inhibitors include hydroquinone, hydroquinone monomethyl ether, phenothiazine, benzoquinone and derivatives thereof. A quantity of the polymerization inhibitor to be added is, based on the polymerizable monomer, preferably from 0% by weight to 10% by weight and more preferably from 0% by weight to 5% by weight.

The liquid crystal composition according to the invention can be prepared by dissolving or dispersing the above-described components in an adequate solvent. It can be formed in a suitable shape, or formed on a support or the like. Examples of such solvents include 2-butanone, cyclohexanone, methylene chloride and chloroform.

Method of Changing Helical Structure of Liquid Crystal

As described above, the liquid crystal composition according to the invention comprises a photo-reactive chiral agent (optically active isosorbide derivative according to the invention or optically active isomannide derivative according to the invention). In a method for changing the helical structure of the liquid crystal according to the invention, the helical pitch (helical twisting power) of the liquid crystal is allowed to be changed by irradiating the liquid crystal composition according to the invention by light at a desired light quantity in a desired pattern whereupon the helical structure of the liquid crystal, that is, a region with a different degree of helical twisting (helical twisting power; HTP) can be formed.

Further, particularly in a case in which the liquid crystal phase is a cholesteric liquid crystal phase, the selectively reflected color displayed by the liquid crystal can arbitrarily be changed in accordance with the helical twisting power thereof. When a change ratio of the helical twisting power (twist change ratio) is large, color width of the selectively reflected color capable of being selectively reflected by the liquid crystal is large whereupon the selective reflection in a wide wavelength range comprising the three primary colors (B, G, R) can be obtained. This feature is important, since the three primary colors, that is, B, G, and R, of high color purity can be displayed. In this regard, since the optically active isosorbide derivative as represented by the general formula (I) or the optically active isomannide derivative as represented by the general formula (V) can substantially change the helical twisting power of the liquid crystal helical structure, by using the liquid crystal composition containing the compound (chiral agent), a wide hue comprising the three primary colors, that is, blue (B), green (G), and red (R), can be displayed and, further, the three primary colors which are excellent in color purity can be obtained.

Specifically, a procedure as described below can be performed.

Namely, the liquid crystal composition is imagewise irradiated with a light in a photosensitive wavelength region of the optically active isosorbide derivative or the optically active isomannide derivative in the liquid crystal composition in the same manner as in the patterning as described in the "Method of Changing Helical Structure of Liquid Crystal". By such irradiation by light, the optically active isosorbide derivative or the optically active isomannide derivative is exposed to change the helical structure of the liquid crystal, thereby forming a pattern imagewise (patterning). After this pattering is performed, light in a photosensitive wavelength region of the photo-polymerization initiator is imagewise irradiated. Thus, the liquid crystalline compound is polymerized by the photo-polymerization initiator and, then, fixed such that the helical structure after being changed is maintained. Prior to this step, for example, a step of nitrogen displacement may be provided.

When the photosensitive wavelength region of the optically active isosorbide derivative or the optically active isomannide derivative and that of the photo-polymerization initiator are different from one the other, there is no chance in which the light irradiation for changing the HTP and the light irradiation for performing the photo-polymerization interfere with each other. Therefore, when the exposure is imagewise performed for changing the HTP, the photo-polymerization does not proceed whereupon patterning having the HTP change ratio can be performed in a predetermined manner and also, when the photo-polymerization is performed for fixing the helical structure, the optically active isosorbide derivative or the optically active isomannide derivative does not respond to the light whereupon a formed change pattern of the HTP can be assuredly fixed.

When a liquid crystal color filter, an optical film or the like to be described below is formed, after patterning is performed by imagewise irradiation with the light having a wavelength by which the optically active isosorbide derivative or the optically active isomannide derivative, the light having a wavelength by which the photo-polymerization initiator is exposed is irradiated for photo-polymerize-hardening a polymerizable group in the liquid crystal composition to fix the helical structure of the liquid crystal at a desired selectively reflected color. Details of the methods for forming the liquid crystal color filter and the optical film will be described below.

A light source to be used for the above-described light irradiation is a same light source as illustrated in the "Method of Changing Helical Structure of Liquid Crystal".

Liquid Crystal Color Filter

Hereinafter, a liquid crystal color filter, an optical film and a recording medium will be described in detail.

The liquid crystal color filter according to the invention at least comprises the liquid crystalline compound and at least one type of the optically active isosorbide derivative according to the invention, or the liquid crystalline compound and at least one type of the optically active isomannide derivative according to the invention. As the liquid crystalline compound, a nematic liquid crystal compound is most favorable. Still, as needed, the liquid crystal color filter according to the invention further comprises a polymerizable monomer, a photo-polymerization initiator, other components illustrated in the liquid crystal composition according to the invention, a surfactant having the excluded volume effect and the like.

For example, the liquid crystal color filter according to the invention can be produced by irradiation with the light in a desired pattern and at a desired light quantity which have appropriately been selected based on the above-described "Method of Changing Helical Structure of Liquid Crystal" and the "Method of Fixing Helical Structure of Liquid Crystal".

The liquid crystal color filter according to the invention will now be explained in detail by means of explaining a production method thereof.

The liquid crystal color filter according to the invention can be produced by appropriately selecting one member from the group consisting of the liquid crystal compositions according to the invention and known compositions each containing an optically active isosorbide derivative represented by the general formula (I), or by appropriately selecting one member from the group consisting of the liquid crystal compositions according to the invention and known compositions each containing an optically active isomannide derivative represented by the general formula (V).

On this occasion, the liquid crystal color filter may be in sheet-like form comprising only the liquid crystal composition, or may be in a shape in which a layer (liquid crystal layer) containing the liquid crystal composition is provided on a desired support or a temporary support, or may be in a shape in which other layers (films) such as an orientation film and a protection film are further provided on the resultant desired support or temporary support. In the latter case, two or more liquid crystal layers may be laminated whereupon the exposure step to be described below is performed a plurality of times.

As for the nematic liquid crystal compound, the polymerizable monomer, the photo-polymerization initiator and other components, same types of those which are usable in the liquid crystal composition according to the invention can be used. Quantities of those to be contained, preferable ranges thereof and the like are also same as in the liquid crystal composition. Further, it is preferable that a surfactant having an excluded volume effect is simultaneously used.

Still further, a quantity to be contained of the optically active isosorbide derivative as represented by the general formula (I) or the optically active isomannide derivative as represented by the general formula (V) in the liquid crystal composition constituting the liquid crystal color filter is same as in the liquid crystal composition according to the invention.

The liquid crystal color filter according to the invention can favorably be produced by using, for example, the liquid crystal composition according to the invention.

Further, the method for producing the liquid crystal color filter is not particularly limited. For example, a production method comprising at least one cycle of a step consisting of performing patterning by image-wise exposure with a first light and, then, performing hardening by photo-polymerization with a second light (hereinafter also referred to as "exposure step") can be adopted. Namely, "Method for Fixing Helical Structure of Liquid Crystal" according to the invention may be adopted. Furthermore, in accordance with production types to be selected, the liquid crystal color filter according to the invention may be formed by optionally passing through a step of applying an orientation treatment on a surface in contact with the liquid crystal composition (orientation treatment step), a step of transferring a liquid crystal layer by adhesion/peeling (transfer step), a step of forming a liquid crystal layer by applying a cholesteric liquid crystal composition (coating step) or the like.

Hereinafter, as an example of a production method comprising the above-described exposure step, a specific embodiment using a cholesteric liquid crystal composition will be described.

Exposure Step

In the exposure step, both patterning of the liquid crystal compound and fixation (polymerize-hardening) are performed by light irradiation.

That is, after performing patterning by image-wise exposure with a first light of a wavelength to which the optically active isosorbide derivative or the optically active isomannide derivative (hereinafter also referred to sometimes as "photo-reactive chiral agent") is highly sensitive, photo-polymerization is performed by a second light to which the polymerization initiator is highly sensitive for hardening whereupon the helical structure of the liquid crystal compound is fixed at a desired selectively reflected color.

When the liquid crystal composition is irradiated with the first light, the co-existent photo-reactive chiral agent is exposed in accordance with an irradiation degree thereof to change the helical structure of the liquid crystal compound. According to such structural change, a different selectively reflected color is exhibited to form image-wise pattern. Therefore, by irradiation with light having different irradiation intensities for respective desired regions, a plurality of colors can be exhibited corresponding to the irradiation intensities. For example, by exposure through a mask for use in exposure which has been produced such that it has different light transmittance, an image, that is, colored regions in which different selective reflections are performed, can simultaneously be formed by one-time light irradiation. Subsequently, by further irradiation with the second light to the thus-exposed liquid crystal composition for hardening (fixing), the liquid crystal color filter can be produced.

The wavelength of the first light is preferably set in a photosensitive wavelength region of the photo-reactive chiral agent, in particular, at a wavelength in the vicinity of the photo-sensitivity peak wavelength thereof in order to obtain sufficient patterning sensitivity. Further, the wavelength of the second light is preferably set in a photosensitive wavelength region of the polymerization initiator, in particular, at a wavelength in the vicinity of the photosensitivity peak wavelength thereof in order to obtain sufficient photo-polymerization sensitivity.

Still further, the irradiation degree (irradiation intensity) of each of the first and second light is not particularly limited and can appropriately be selected in accordance with the material to be used so as to obtain a sufficient light sensitivity at the time of patterning and polymerize-hardening. As for the light source used for the first and second light irradiation, a same light source which is usable for the light irradiation for the above-described liquid crystal composition can be used as well.

More specifically, production methods of first and second embodiments described below can be used as well. The liquid crystal color filter according to the invention can more advantageously be produced by these two embodiments.

First Embodiment (1) Step for providing a liquid crystal composition in coating solution form on a temporary support to form a transfer material having at least a liquid crystal layer.

The liquid crystal composition in the coating solution form can be prepared by dissolve-dispersing each component in an appropriate solvent. Here, as for such solvents, for example, 2-butanone, cyclohexanone, methylene chloride and chloroform can be used. In production of the liquid crystal color filter, a cholesteric liquid crystal composition is preferable.

A cushion layer comprising a thermoplastic resin or the like can be provided between the liquid crystal layer and the temporary support from the viewpoint of ensuring an adhesion property at the time of transfer, for example, in a case in which a foreign substance or the like is present on a member to be transferred. It is also preferable that a surface of the cushion layer is subjected to an orientation treatment such as a rubbing treatment (orientation treatment step).

(2) Step of laminating the transfer material on a light transmissible substrate.

Other than the light transmissible substrate, an image receiving material having an image receiving layer on the substrate may be used as well. Further, the liquid crystal composition can be coat-formed directly on the substrate without using the transfer material (coating step). Such coating operation can be performed by selecting an appropriate method from known coating methods which use, for example, a bar coater or a spin coater. However, in view of material loss and cost, a method using a transfer technique is preferable.

(3) Step of forming a cholesteric liquid crystal layer on the substrate by peeling off the transfer material from the light transmissible substrate (transfer step).

The liquid crystal layer may be formed in a plurality of layers by further laminating after performing a step (4) to be described below.

(4) Step of forming a pixel pattern showing a selectively reflected color by imagewise irradiation of an ultraviolet ray having an illuminance intensity of $v^1$ on the cholesteric liquid crystal layer via an exposure mask and, subsequently, hardening the layer by further irradiating the ultraviolet ray having an illuminance intensity of $v^2$ thereon (exposure step).

Second Embodiment (1) Step of forming a liquid crystal layer by providing a liquid crystal composition directly on a support constituting a color filter.

Here, the liquid crystal layer can be formed by applying the liquid crystal composition prepared in coating solution form in the same manner as described above by a known application method using a bar coater, a spin coater or the like.

Further, the orientation film may be formed between the cholesteric liquid crystal layer and the temporary support in the same manner as described above. It is also preferable that a surface of the orientation film is subjected to an orientation treatment (orientation treatment step) such as a rubbing treatment.

(2) Exposure step in the same manner as in the step (4) of the first embodiment.

Thickness of the liquid crystal layer (sheet-like liquid crystal composition) to function as the liquid crystal color filter is preferably from 1.5 µm to 4 µm.

An example will be illustrated below with reference to FIGS. 1A to 3C. FIGS. 1A to 3C are each a schematic diagram showing an exemplary embodiment of production steps of a liquid crystal color filter according to the invention.

First, the respective components described above are dissolved in an appropriate solvent to prepare a coating solution-like cholesteric liquid crystal composition. The components and the solvent are same as those described above.

Figure 1B:
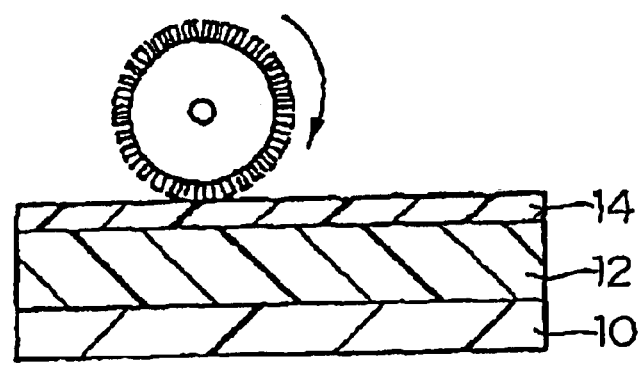

As shown in FIG. 1A, a support 10 (hereinafter also referred to as "temporary support") is prepared. By coating on the support 10, for example, an acrylic resin, polyester or polyurethane, a cushion layer (thermoplastic resin layer) 12 is provided. And, further, an orientation film 14 made of a polyvinyl alcohol or the like is laminated thereon. The orientation film, as shown in FIG. 1B, is subjected to a rubbing treatment. The rubbing treatment is not necessarily required, but the orientation property can further be improved by performing the rubbing treatment.

Figure 1C:
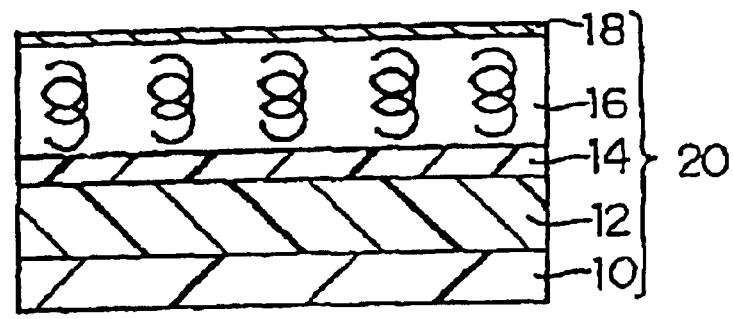

Next, as shown in FIG. 1C, after applying a coating solution-like cholesteric liquid crystal composition on the orientation film 14 and drying to form a cholesteric liquid crystal layer 16, a cover film 18 is provided on the thus-formed cholesteric liquid crystal layer 16 to produce a transfer material. Hereinafter, the transfer material is referred to as a transfer sheet 20.

Figure 1D:
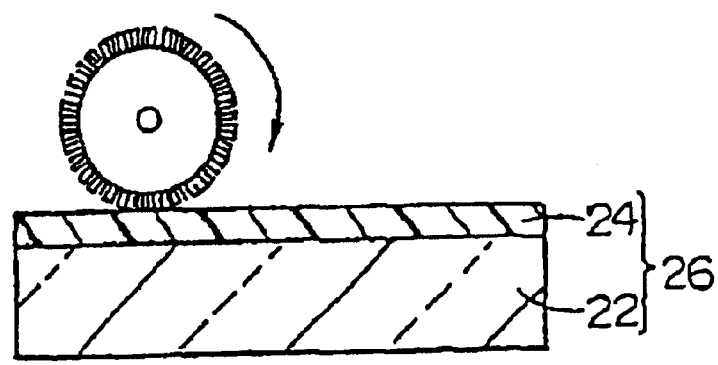

On the other hand, as shown in FIG. 1D, another support 22 is prepared. In the same manner as described above, an orientation film 24 is formed on the support, and further the surface thereof is subjected to a rubbing treatment. Hereinafter, this will be referred to as a substrate for a color filter 26.

Figure 2A:
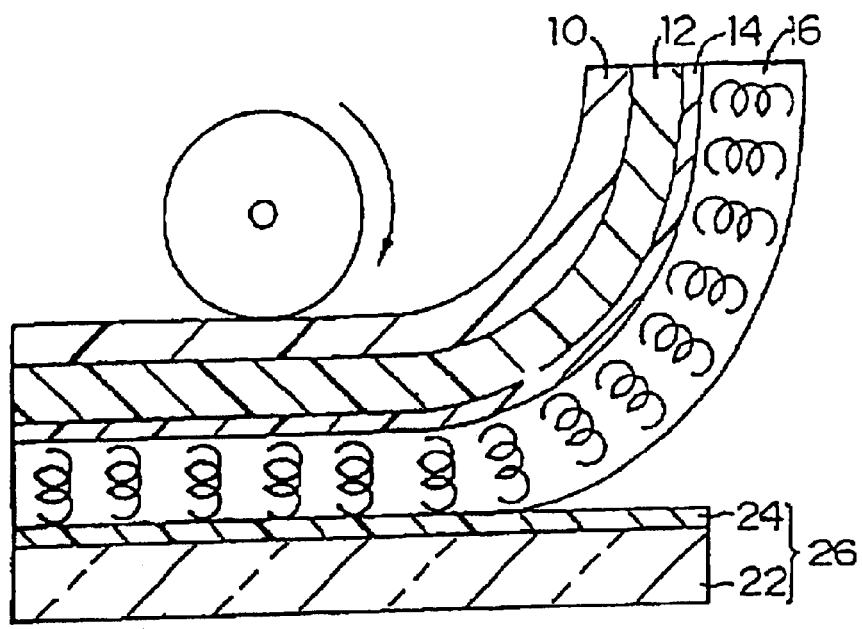
FIGS. 2A and 2B are each a schematic diagram showing a part of processes for producing a liquid crystal color filter according to the present invention.
Figure 2B:
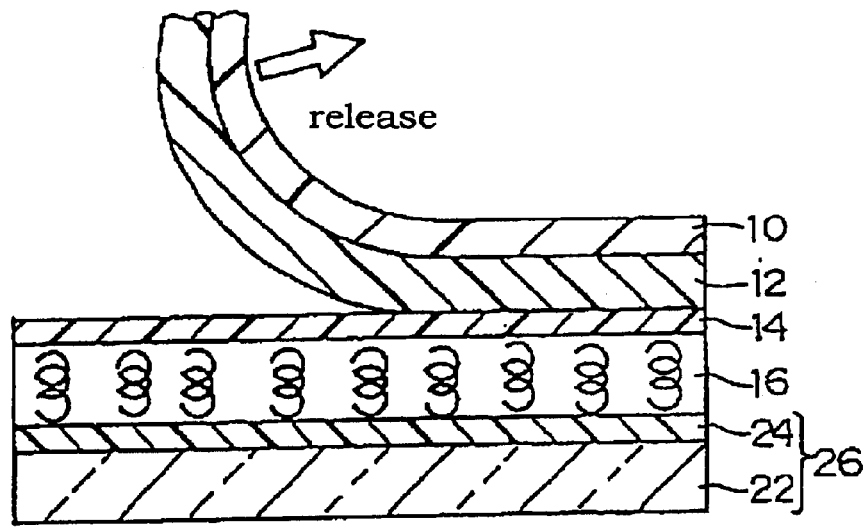

Next, after peeling off the cover film 18 of the transfer sheet 20, as shown in FIG. 2A, the surface of the cholesteric liquid crystal layer 16 of the transfer sheet 20 and the surface of the orientation film 24 of the substrate for a color filter 26 are superimposed such that they come in contact with each other. Using a roll rotating in an arrow direction as shown in FIG. 2A, they are laminated. Thereafter, as shown in FIG. 2B, peeling between the orientation film 14 and the cushion layer 12 of the transfer sheet 20 is performed whereupon the cholesteric liquid crystal layer is transferred onto the substrate for the color filter together with the orientation film 14. On this occasion, the cushion layer 12 may not necessarily be peeled off together with the temporary support 10.

Figure 3A:
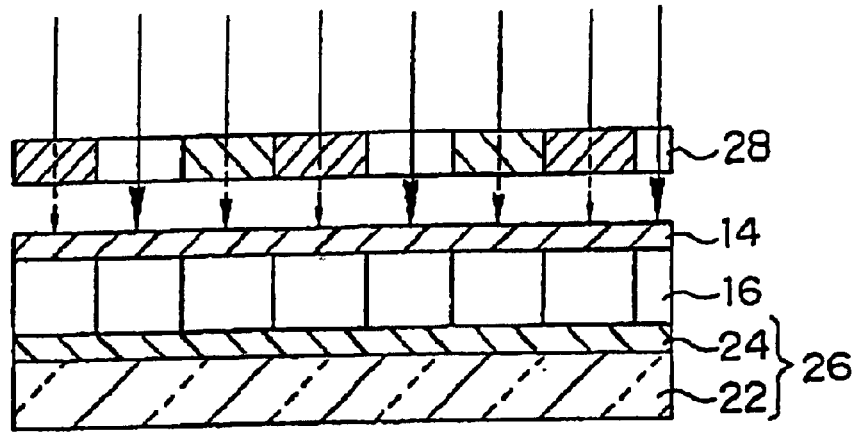
FIGS. 3A to 3C are each a schematic diagram showing a part of processes for producing a liquid crystal color filter according to the present invention.

After the transfer, as shown in FIG. 3A, an exposure mask 28 having a plurality of regions with different light transmittance is disposed above the orientation film 14. Through the mask 28, the cholesteric liquid crystal layer 16 is irradiated with a first light in a pattern state. A liquid crystalline compound, a chiral compound and the like are contained in the cholesteric liquid crystal layer 16 such that helical pitches differ from one another in accordance with quantities of light irradiation. A structure having different helical pitches is formed per pattern such that, for exmple, a region in which green (G) is reflected while blue (B) and red (R) are allowed to be transmitted, a region in which blue (B) is reflected while green (G) and red (R) are allowed to be transmitted, and a region in which red (R) is reflected while green (G) and blue (B) are allowed to be transmitted are formed.

Figure 3B:
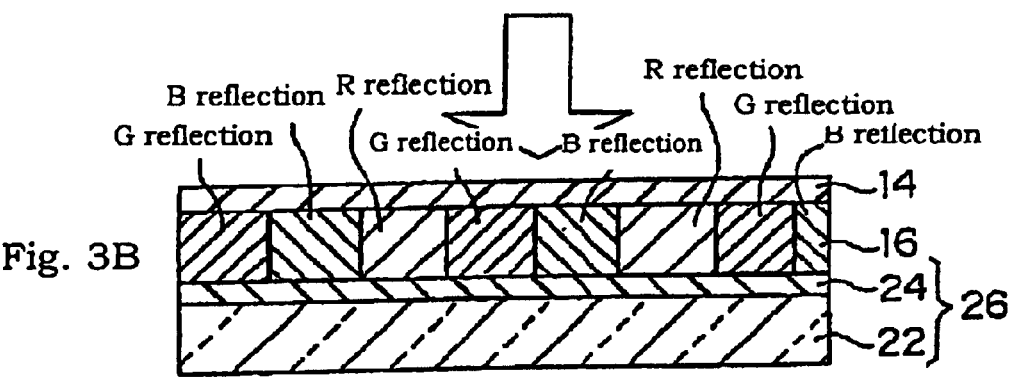

Next, as shown in FIG. 3B, the pattern is fixed by further irradiating the the cholesteric liquid crystal layer 16 with ultraviolet ray having an irradiation intensity different from that of the light irradiation in the above-described step (G). Thereafter, by removing unnecessary portions (for example, residual portions of the cushion layer and the intermediate layer, and unexposed portions) on the cholesteric liquid crystal layer 16 using 2-butanone, chloroform or the like, a cholesteric liquid crystal layer having the BGR reflection regions can be formed as shown in FIG. 3C.

Figure 3C:
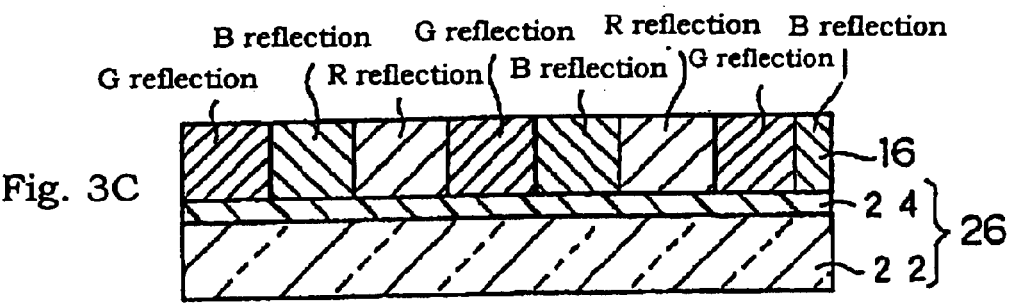

Although the method as shown in the FIGS. 1A to 3C is an embodiment of a production method for a color filter in which the laminate method is used, a production method using a coating method in which the liquid crystal layer is coat-formed directly on a substrate for a color filter may be used as well. On this occasion, according to the above-described embodiment, after the cholesteric liquid crystal layer is applied on the orientation film 24 of the substrate 26 for a color filter as shown in FIG. 1D and, then, dried, same steps as shown in FIGS. 3A to 3C are executed successively.

The steps and the materials to be used, such as the transfer material, and the support material are described in detail in Japanese Patent Application Nos. 11-342896 and 11-343665 which have previously been proposed by the present inventors.

As described above, when the liquid crystal composition containing the optically active isosorbide derivative or the optically active isomannide derivative is used, since the change ratio of the helical twisting power of the liquid crystal helical structure is large in accordance with the light quantity, the color width of the selectively reflected color to be exhibited by the liquid crystal can be expanded whereupon a liquid crystal color filter having the three primary colors, blue (B), green (G), and red (R) with excellent color purity can be obtained.

Optical Film

An optical film according to the invention comprises at least the liquid crystalline compound and at least one type of the optically active isosorbide derivative according to the invention and an optical wavelength is arbitrarily set therein from among a wide range of wavelengths. Alternatively, the optical film according to the invention comprises at least the liquid crystalline compound and at least one type of the optically active isomannide derivative according to the invention and an optical wavelength is arbitrarily set therein from among a wide range of wavelengths. The optical film according to the invention may optionally further comprise other components such as a polymerizable monomer, a photo polymerization initiator and a surfactant having the excluded volume effect in the same manner as in the liquid crystal composition according to the invention whereupon the optical film according to the invention can be produced by light irradiation with desired pattern and light quantity which have appropriately been selected. For example, the optical film according to the invention can be produced by being based on the above-described "Method for Changing Helical Structure of Liquid Crystal" and "Method for Fixing Helical Structure of Liquid Crystal".

The optical film according to the invention can be produced by appropriately selecting one member from the group consisting of the liquid crystal compositions according to the invention and known compositions each containing an optically active isosorbide derivative as represented by the general formula (I), or by appropriately selecting one member from the group consisting of the liquid crystal compositions according to the invention and known compositions each containing an optically active isomannide derivative as represented by the general formula (V). Here, the form of the optical film is not particularly limited, and it can be sheet-like form comprising only the above-described liquid crystal composition, the sheet-like form in which the layer comprising the liquid crystal composition (liquid crystal layer) is provided on a desired support or a temporary support, or the sheet-like form in which other layers (films) such as an orientation film and a protection film are further provided.

As for the liquid crystalline compound, the polymerizable monomer, the photo polymerization initiator and other components, those components which are same as those usable for the liquid crystal compositions can be used. A quantity of each of the components to be contained, preferable range or the like, is same as in the liquid crystal composition. Further, a quantity of the optically active isosorbide derivative as represented by the general formula (I) to be contained in the liquid crystal composition constituting the optical film or a quantity of the optically active isomannide derivative as represented by the general formula (V) to be contained in the liquid crystal composition constituting the optical film is also same as that of the liquid crystal composition according to the invention.

The optical film according to the invention can be produced preferably, for example, by using the liquid crystal composition according to the invention.

Further, as for the method for producing the optical film, the substantially same production method as that of the liquid crystal color filter can be adopted. It can be a method in which the exposure step is performed at least once. That is, the method can adopt the above-described "Method for Fixing Helical Structure of Liquid Crystal". Still further, the optical film can be produced via steps such as the orientation treatment step, the transfer step and the coating step in accordance with an embodiment of the production thereof to be selected.

More specifically, the optical film according to the invention can be produced by employing the substantially same production method as in the first and second embodiments.

As heretofore described, by using the liquid crystal composition containing the optically active isosorbide derivative or the liquid crystal composition containing the optically active isomannide derivative, an optical film of non-light absorption type which can substantially change the helical pitch of the liquid crystal in accordance with the light quantity can be obtained. For example, in a case in which the liquid crystal phase is a cholesteric liquid crystal phase, an optical film having various selectively reflected colors in a wide color range of the liquid crystal selective reflection, an optical film having the primary colors (B, G, R) with excellent color purity and the like can be obtained.

Recording Medium

A recording medium according to the invention comprises the liquid crystalline compound and at least one type of the optically active isosorbide derivative according to the invention or the liquid crystalline compound and at least one type of the optically active isomannide derivative according to the invention and optionally further comprises a polymerizable monomer, a photo polymerization initiator and other components described in the liquid crystal composition according to the invention, such as a surfactant having the excluded volume effect.

The recording medium according to the invention is not limited to any particular shape, and it may be in sheet-like form comprising only the liquid crystal composition, or in a shape in which a layer comprising the liquid crystal composition containing a photo-reactive chiral agent (liquid crystal layer) is provided on a desired support or a temporary support (hereinafter referred to as "support or the like"). Here, the liquid crystal composition can appropriately be selected from the group consisting of the liquid crystal compositions according to the invention and known compositions each containing an optically active isosorbide derivative as represented by the general formula (I), or appropriately selected from the group consisting of the liquid crystal compositions according to the invention and known compositions each containing an optically active isomannide derivative as represented by the general formula (V). Further, other layers (films) such as an orientation film and a protection film can be provided thereto.

As for the liquid crystalline compound, the polymerizable monomer, the photo polymerization initiator and other components, those components which are same as those usable for the liquid crystal composition can be used. A quantity of each of the components to be contained, preferable range or the like, is same as in the liquid crystal composition. Further, a quantity of the optically active isosorbide derivative as represented by the general formula (I) to be contained in the liquid crystal composition constituting the optical film or a quantity of the optically active isomannide derivative as represented by the general formula (V) to be contained in the liquid crystal composition constituting the optical film is also same as that of the liquid crystal composition according to the invention.

The recording medium according to the present invention can preferably be produced by providing the liquid crystal composition according to the present invention on a support or the like.

Examples of methods for providing the liquid crystal composition on the support or the like include (1) a method of transferring a liquid crystal layer on a support by using a transfer material in which the liquid crystal layer containing the liquid crystal composition according to the invention is provided on a temporary support, and (2) a method of directly applying the liquid crystal composition prepared in coating solution form on a support.

In the above-described methods (1) and (2), the transfer material, the coating method and the like can be adapted in accordance with the embodiments (first and second embodiments) illustrated in the liquid crystal composition according to the invention and explanations with reference to FIGS. 1A to 3C.

In the recording medium according to the present invention produced in a manner as described above, an image, or, particularly in a case of a cholesteric liquid crystal, a colored image constituted by selectively reflected colors to be determined by a change ratio of the helical pitch can be formed in accordance with a change ratio of the helical twisting power of the liquid crystal by light irradiation with the appropriately selected desired pattern and light quantity. The image can also be formed, for example, based on the above-described "Method for Changing Helical Structure of Liquid Crystal" and the "Method for Fixing Helical Structure of Liquid Crystal".

Further, by using the optically active isosorbide derivative as represented by the general formula (I) or the optically active isomannide derivative as represented by the general formula (V) as a chiral agent for changing the liquid crystal structure, since a change ratio of the helical twisting power of the liquid crystal helical structure is large, an image having a wide range of color reproduction can be formed. Particularly in a case of a cholesteric liquid crystal, the hue width in which the liquid crystal is capable of performing the selective reflection can be expanded whereupon a colorful multi-colored image of high color purity can be formed. Still further, the large change ratio of the helical twisting power substantially contributes also to achievement of high sensitivity (high speed) at the time of image formation.

Furthermore, by using a polymerizable liquid crystal compound or a polymerizable monomer, for example, the liquid crystal after patterning can be fixed whereupon an image excellent in image stability can be formed.

As for the light source for irradiation, by using a same light source as that usable in the liquid crystal composition according to the invention, optical recording can favorably be performed. Further, the same applies to a case of the light irradiation for fixing the liquid crystal.

As heretofore explained, by using the optically active isosorbide derivative or the optically active isomannide derivative as a chiral agent for changing the helical structure of the liquid crystal molecule, the helical twisting power (twist angle) of the liquid crystal can substantially be changed. Particularly in a case of a cholesteric liquid crystal using a nematic liquid crystal compound, the selective reflection wavelength range obtained by the light irradiation can be expanded. As a result, the color purity of the three primary colors BGR can further be improved. Therefore, the hue selectivity and the sharpness of the liquid crystal can be improved. Particularly in a liquid crystal color filter, an optical film or the like, a clear and sharp color image can be displayed. In the recording medium, an image to be formed can have diversified hues.

EXAMPLES

Hereinafter, illustrative syntheses of the optically active isosorbide derivative and the optically active isomannide derivative according to the invention are described and should not be interpreted as limiting the invention in any way. Unless otherwise stated, all parts and percentages (%) in examples are given by mass.

Example 1

Synthesis of Illustrative Compound 1-2

4 mmol (0.52 ml) of 2-methylbenzoyl chloride was dropwise added to a mixture of 2 mmol (0.87 g) of a compound (A-1) as described below, 4.4 mmol (0.45 g) of triethyl amine and 10 ml of acetonitrile under an ice-cooled condition. The resultant mixture was stirred at room temperature for 2 hours. The resultant reaction product was poured into water, thereby obtaining a resultant solid material. The solid material was dissolved in ethanol and, then, recrystallized to obtain 0.83 g of an illustrative compound (1-2) which was a light yellow solid. The yield rate thereof was 62%.

$[\alpha]_D^{25}$ -183° (c0.10, $CHCl_3$)

Results of identification of the thus-obtained crystal by an analysis using $^1$H-NMR ($CDCl_3$) are shown below.

δ (in ppm from TMS); 7.89–7.20 (m, 20H), 6.52–6.28 (m, 2H), 5.40–5.23 (m, 2H), 5.00–4.90 (m, 1H), 4.66–4.58 (m, 1H), 4.18–3.83 (m, 4H), 2.51 (s, 6H)

Compound (A-1)

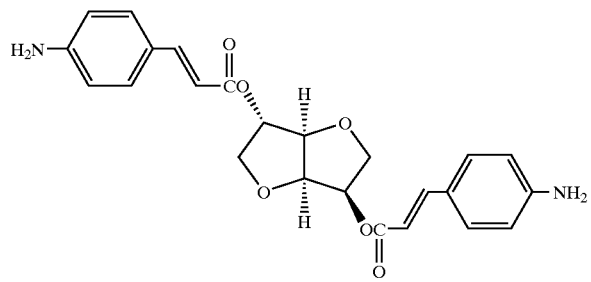

Example 2

Synthesis of Illustrative Compound 1-7

2 mmol (0.23 g) of benzoyl chloride was dropwise added to a mixture of 1 mmol (0.50 g) of a compound (A-2) as described below, 2.1 mmol (0.21 g) of triethyl amine, 5 ml of acetonitrile and 5 ml of THF under an ice-cooled condition. The resultant mixture was stirred at room temperature for 2 hours. The resultant reaction product was poured into water and, then, extracted by ethyl acetate. The resultant ethyl acetate layer was condensed to obtain a residue. The thus-obtained residue was recrystallized by acetone/methanol to obtain 0.54 g of an illustrative compound (1-7). The yield rate thereof was 77%.

$[\alpha]_D^{25}$ -213° (c0.10, $CHCl_3$)

Results of identification of the thus-obtained crystal by an analysis using $^1$H-NMR ($CDCl_3$) are shown below.

δ (in ppm from TMS); 8.68 (s, 2H), 8.60 (H, 2H), 7.97–7.85 (m, 4H), 7.73 (d, 1H), 7.69 (d, 1H), 7.62–7.44 (m, 6H), 7.27–7.03 (m, 4H), 6.48 (d, 1H), 6.39 (d, 1H), 5.43–5.27 (m, 2H), 5.01–4.92 (m, 1H), 4.67–4.59 (m, 1H), 4.20–3.82 (m, 10H)

Compound (A-2)

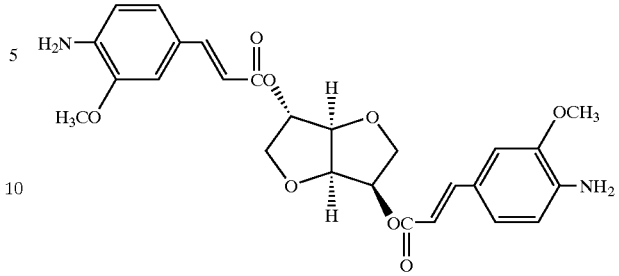

Example 3

Synthesis of Illustrative Compound (1-8)

An illustrative compound (1-8) was obtained in the same manner as in Example 2. The yield rate thereof was 68%.

$[\alpha]_D^{25}$ -187° (c0.10, $CHCl_3$)

Results of identification performed by using $^1$H-NMR ($CDCl_3$) are shown below.

δ (TMS); 9.39 (s, 1H), 9.33 (s, 1H), 9.33 (s, 1H), 8.62 (d, 2H), 8.23–8.12 (m, 2H), 7.74 (d, 1H), 7.70 (d, 1H), 7.60–7.14 (m, 8H), 7.09 (d, 2H), 6.47 (d, 1H), 6.39 (d, 1H), 5.42–5.28 (m, 2H), 5.02–4.92 (m, 1H), 4.68–4.60 (m, 1H), 4.20–3.82 (m, 10H)

Example 4

Synthesis of Illustrative Compound (1-9)

An illustrative compound (1-9) was obtained in the same manner as in Example 2. The yield rate thereof was 79%.

$[\alpha]_D^{25}$ -180° (c0.10, $CHCl_3$)

Results of identification performed by using $^1$H-NMR ($CDCl_3$) are shown below.

δ (TMS); 8.60 (d, 2H), 8.21 (s, 2H), 7.74 (d, 1H), 7.69 (d, 1H), 7.59–7.17 (m, 10H), 7.07 (d, 2H), 6.47 (d, 1H), 6.39 (d, 1H), 5.42–5.27 (m, 2H), 5.00–4.92 (m, 1H), 4.68–4.60 (m, 1H), 4.20–3.81 (m, 10H), 2.53 (s, 6H)

Example 5

Synthesis of Illustrative Compound (1-10)

An illustrative compound (1-10) was obtained in the same manner as in Example 2. The yield rate thereof was 73%.

$[\alpha]_D^{25}$ -216° (c0.10, $CHCl_3$)

Results of identification performed by using $^1$H-NMR ($CDCl_3$) are shown below.

δ (TMS); 8.68 (s, 2H), 8.59 (d, 2H), 8.18 (d, 4H), 7.96 (d, 4H), 7.73 (d, 1H), 7.69 (d, 1H), 7.25 (s, 1H), 7.22 (s, 1H), 7.08 (d, 2H), 6.49 (d, 1H), 6.40 (d, 1H), 5.42–5.27 (m, 2H), 5.01–4.92 (m, 1H), 4.68–4.60 (m, 1H), 4.20–3.82 (m, 16H)

Example 6

Synthesis of Illustrative Compound (1-20)

A mixture of 5.5 mmol (1.4 g) of a compound (A-3) as described below, 12.1 mmol (3.9 g) of a compound (A-4) as described below, 0.02 g of palladium acetate, 0.13 g of tri(o-tolyl)phosphine, 12.1 mmol (1.2 g) of trimethyl amine and 20 ml of DMF was stirred while heated at an external temperature of 100° C. for 30 minutes. The resultant reaction product was cooled and, then, poured into diluted hydrogen chloride to generate a solid. The thus-generated solid was filtered to recover the solid. The thus-recovered solid was purified by a column chromatography and, then, rinsed with methanol to obtain 1.4 g of an illustrative compound (1-20) which was a light yellow solid. The yield rate thereof was 38%.

$[\alpha]_D^{25}$ -177° (c0.10, $CHCl_3$)

Results of identification of the thus-obtained crystal by an analysis using ¹H-NMR (CDCl₃) are shown below.

δ (TMS); 9.90 (6s, 1H), 8.00–7.50 (m, 18H), 6.70 (d, 1H), 6.65 (d, 1H), 5.30–5.20 (m, 2H), 4.90 (t, 1H), 4.35 (d, 1H), 4.00–3.80 (m, 4H), 2.30 (s, 6H)

Compound (A-3)

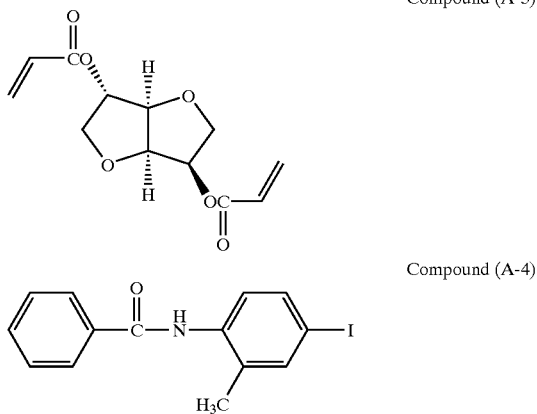

Compound (A-4)

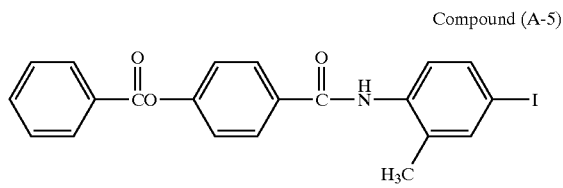

Example 7

Synthesis of Illustrative Compound (1-21)

An illustrative compound (1-21) was obtained in the same manner as in Example 6 except that the illustrative compound (A-4) was changed into an illustrative compound (A-5) as described below. The yield rate thereof was 36%.

$[\alpha]_D^{25}$ –158° (c0.10, CHCl₃)

Results of identification by using ¹H-NMR (CDCl₃) are shown below.

δ (TMS); 8.25–7.35 (m, 28H), 6.45 (d, 1H), 6.40 (d, 1H), 5.40–5.30 (m, 2H), 4.95 (t, 1H), 4.60 (d, 1H), 4.15–3.90 (m, 4H), 2.35 (s, 6H)

Compound (A-5)

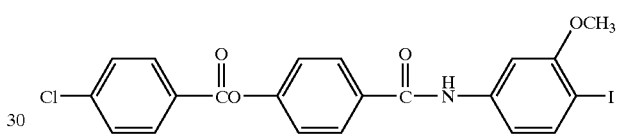

Example 8

Synthesis of Illustrative Compound 1-26

An illustrative compound (1-26) was obtained in the same manner as in Example 6 except that the illustrative compound (A-4) was changed into an illustrative compound (A-6) as described below. The yield rate thereof was 50%.

$[\alpha]_D^{25}$ –169° (c0.10, CHCl₃)

Results of identification of the thus-obtained crystal by an analysis using ¹H-NMR (DMSO-d⁶) are shown below.

δ (TMS); 8.05–7.45 (m, 18H), 6.60 (d, 1H), 6.55 (d, 1H), 5.30–5.20 (m, 2H), 4.90 (t, 1H), 4.52 (d, 1H), 3.96–3.80 (m, 10H), 3.32 (s, 6H)

Compound (A-6)

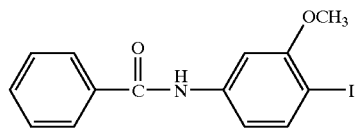

Example 9

Synthesis of Illustrative Compound 1-32

An illustrative compound (1-32) was obtained in the same manner as in Example 6 except that the illustrative compound (A-4) was changed into an illustrative compound (A-7) as described below. The yield rate thereof was 67%.

$[\alpha]_D^{25}$ –139° (c0.10, CHCl₃)

Results of identification by using ¹H-NMR (CDCl₃) are shown below.

δ (TMS); 8.14 (d, 4H), 8.05 (s, 2H), 7.95–7.90 (m, 6H), 7.70 (s, 2H), 7.60–7.45 (m, 6H), 7.30 (d, 4H), 7.0 (d, 2H), 6.55 (d, 1H), 6.50 (d, 1H), 5.40–5.25 (m, 2H), 4.95 (t, 1H), 4.60 (d, 1H), 4.20–3.90 (m, 4H), 3.90 (s, 6H)

Compound (A-7)

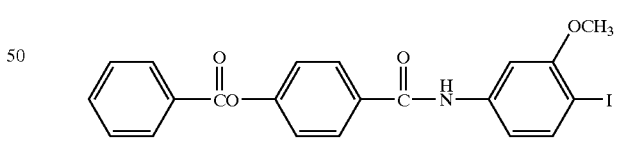

Example 10

Synthesis of Illustrative Compound 1-33

An illustrative compound (1-33) was obtained in the same manner as in Example 6 except that the illustrative compound (A-4) was changed into an illustrative compound (A-8) as described below. The yield rate thereof was 21%.

$[\alpha]_D^{25}$ –152° (c0.10, CHCl₃)

Results of identification by using ¹H-NMR (CDCl₃) are shown below.

δ (TMS); 8.30 (d, 4H), 8.13–7.35 (m, 30H), 7.00 (d, 2H), 6.55 (d, 1H), 6.50 (d, 1H), 5.40–5.25 (m, 2H), 4.95 (t, 1H), 4.64 (d, 1H), 4.20–3.86 (m, 4H), 3.92 (s, 6H)

Compound (A-8)

Example 11

Synthesis of Illustrative Compound 1-25

An illustrative compound (1-25) was obtained in the same manner as in Example 6 except that the illustrative compound (A-4) was changed into an illustrative compound (A-9) as described below. The yield rate thereof was 80%.

Results of identification of the thus-obtained crystal by an analysis using ¹H-NMR (DMSO-d⁶) are shown below.

δ (TMS); 7.93–7.61 (m, 10H), 7.52–7.41 (m, 2H), 6.94–6.82 (m, 4H), 6.64–6.50 (m, 2H), 5.30–5.18 (m, 2H), 4.92–4.82 (m, 1H), 4.56–4.49 (m-1H), 4.00–3.64 (m, 10H)

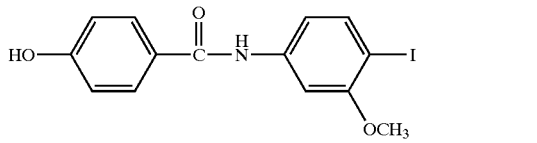

Compound (A-9)

Example 12
Synthesis of Illustrative Compound 1-27

1.66 mmol (0.23 g) of benzoyl chloride was dropwise added to a mixture of 0.81 mmol (0.60 g) of the illustrative compound (1-25), 1.78 mmol (0.18 g) of triethyl amine and 5 ml of tetrahydro-furan under an ice-cooled condition. The resultant mixture was stirred at room temperature for 2 hours. The resultant reacted mixture was poured into water and, then, filtered to recover a generated solid substance. Thereafter, the thus-recovered solid substance was purified through a column chromatography to obtain 0.36 g of a compound (1-27) which is a light yellow solid. The yield rate thereof was 47%.

$[\alpha]_D^{25}$ -161° (c0.10, CHCl$_3$)

Results of identification of the thus-obtained crystal by an analysis using $^1$H-NMR (CDCl$_3$) are shown below.

δ (TMS); 8.23 (d, 4H), 8.05–7.90 (m, 8H), 7.80–7.45 (m, 10H), 7.40 (d, 4H), 7.00–6.90 (m, 2H), 6.62–6.48 (m, 2H), 5.40–5.30 (m, 2H), 5.01–4.91 (m, 1H), 4.64–4.60 (m, 1H), 4.20–3.80 (in, 10H)

Example 13
Synthesis of Illustrative Compound 1-28

An illustrative compound (1-28) was obtained in the same manner as in Example 11 except that benzoyl chloride was changed into 4-methylbenzoyl chloride. The yield rate thereof was 20%.

$[\alpha]_D^{25}$ -148° (c0.10, CHCl$_3$)

Results of identification by using $^1$H-NMR (CDCl$_3$) are shown below.

δ (TMS); 8.20–7.90 (m, 8H), 7.75 (s, 2H), 7.55–7.45 (m, 2H), 7.40–7.28 (m, 2H), 7.00 (d, 2H), 6.65–6.45 (m, 2H), 5.40–5.30 (m, 2H), 4.97 (t, 1H), 4.64 (d, 1H), 4.20–3.75 (m, 8H), 2.45 (s, 6H)

Example 14
Synthesis of Illustrative Compound 1-29

An illustrative compound (1-29) was obtained in the same manner as in Example 11 except that benzoyl chloride was changed into 4-fluorobenzoyl chloride. The yield rate thereof was 40%.

$[\alpha]_D^{25}$ -137° (c0.10, CHCl$_3$)

Results of identification by using $^1$H-NMR (CDCl$_3$) are shown below.

6 (TMS); 8.30–8.20 (in, 4H), 8.05 (s, 2H), 8.00–7.90 (m, 6H), 7.74 (s, 2H), 7.50 (d, 1H), 7.46 (d, 1H), 7.40–7.15 (m, 8H), 6.98 (d, 2H), 6.62–6.42 (m, 2H), 5.40–5.26(m, 2H), 4.97 (t, 1H), 4.62 (d, 1H), 4.20–3.88 (in, 10H)

Example 15
Synthesis of Illustrative Compound 1-30

An illustrative compound (1-30) was obtained in the same manner as in Example 11 except that benzoyl chloride was changed into 4-methoxybenzoyl chloride. The yield rate thereof was 40%.

$[\alpha]_D^{25}$ -130° (c0.10, CHCl$_3$)

Results of identification by using $^1$H-NMR (CDCl$_3$) are shown below.

δ (TMS); 8.15 (d, 4H), 8.05–7.90 (m, 8H), 7.72 (s, 2H), 7.55–7.46 (m, 2H), 7.38 (d, 4H), 7.03–6.95 (m, 6H), 6.62–6.55 (m, 2H), 5.40–5.30 (m, 2H), 4.97 (t, 1H), 4.62 (d, 1H), 4.20–4.00 (m, 4H), 3.95 (s, 6H), 3.90 (s, 6H)

Example 16
Synthesis of Illustrative Compound 2-1

An illustrative compound (2-1) was obtained in the same manner as in Example 6 except that the illustrative compound (A-4) was changed into an illustrative compound (A-10) as described below. The yield rate thereof was 60%.

$[\alpha]_D^{25}$ -182° (c0.10, CHCl$_3$)

Results of identification by using $^1$H-NMR (CDCl$_3$) are shown below.

δ (TMS); 7.72 (d, 1H), 7.65 (d, 1H), 7.60–7.25 (m, 16H), 6.42 (d, 1H), 6.35 (d, 1H), 5.40–5.26 (m, 2H), 4.95 (t, 1H), 4.63 (d, 1H), 4.20–4.00 (m, 8H), 3.20–3.05 (m, 4H)

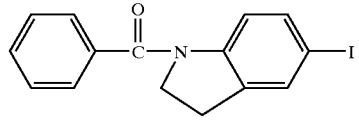

Compound (A-10)

Example 17
Synthesis of Illustrative Compound 2-2

An illustrative compound (2-2) was obtained in the same manner as in Example 6 except that the illustrative compound (A-4) was changed into an illustrative compound (A-11) as described below. The yield rate thereof was 50%.

$[\alpha]_D^{25}$ -181° (c0.10, CHCl$_3$)

Results of identification by using $^1$H-NMR (CDCl$_3$) are shown below.

δ (TMS); 7.70 (d, 1H), 7.65 (d, 1H), 7.46–7.25 (m, 14H), 6.40 (d, 1H), 6.34 (d, 1H), 5.35–5.25 (m, 2H), 4.95 (t, 1H), 4.60 (d, 1H), 4.15–3.85 (m, 8H), 3.20–3.05 (m, 4H), 2.40 (s, 6H)

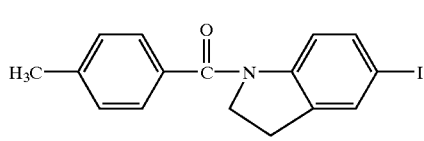

Compound (A-11)

Example 18
Synthesis of Illustrative Compound 2-4

An illustrative compound (2-4) was obtained in the same manner as in Example 6 except that the illustrative compound (A-4) was changed into an illustrative compound (A-12) as described below. The yield rate thereof was 82%.

$[\alpha]_D^{25}$ -166° (c0.10, CHCl$_3$)

Results of identification by using $^1$H-NMR (CDCl$_3$) are shown below.

δ (TMS); 7.70 (d, 1H), 7.65 (d, 1H), 7.55 (d, 4H), 7.40–7.25 (m, 6H), 6.95 (d, 4H), 6.41 (d, 1H), 6.32 (d, 1H), 5.35–5.25 (m, 2H), 4.95 (t, 1H), 4.60 (d, 1H), 4.20–3.65 (m, 14H), 3.20–3.05 (m, 4H)

Compound (A-12)

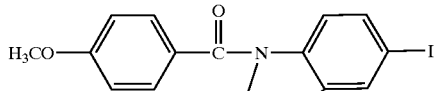

Example 19
Synthesis of Illustrative Compound 2-5

An illustrative compound (2-5) was obtained in the same manner as in Example 6 except that the illustrative compound (A-4) was changed into an illustrative compound (A-13) as described below. The yield rate thereof was 80%.
$[\alpha]_D^{25}$ −160° (c0.10, CHCl$_3$)

Results of identification by using $^1$H-NMR (CDCl$_3$) are shown below.

δ (TMS); 8.25 (d, 2H), 7.70 (d, 1H), 7.65 (d, 1H), 7.42–7.30 (m, 4H), 6.40 (d, 1H), 6.32 (d, 1H), 5.40–5.30 (m, 2H), 4.95 (t, 1H), 4.60 (d, 1H), 4.20–3.80 (m, 8H), 3.25–3.10 (m, 4H), 2.48–2.35 (m, 4H), 1.80–1.65 (m, 4H), 1.40–1.30 (m, 8H), 1.00–0.85 (m, 6H)

Compound (A-13)

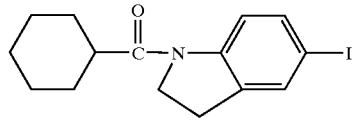

Example 20
Synthesis of Illustrative Compound 2-6

An illustrative compound (2-6) was obtained in the same manner as in Example 6 except that the illustrative compound (A-4) was changed into an illustrative compound (A-14) as described below. The yield rate thereof was 67%.
$[\alpha]_D^{25}$ −121° (c0.10, CHCl$_3$)

Results of identification by using $^1$H-NMR (CDCl$_3$) are shown below.

δ (TMS); 8.32 (d, 2H), 7.70 (d, 1H), 7.65 (d, 1H), 7.50–7.30 (m, 4H), 6.42 (d, 1H), 6.35 (d, 1H), 5.40–5.30 (m, 2H), 4.96 (t, 1H), 4.62 (d, 1H), 4.30–3.80 (m, 8H), 3.25–3.05 (m, 4H), 2.60–2.48 (m, 2H), 1.90–1.20 (m, 16H), 1.00–0.80 (m, 12H)

Compound (A-14)

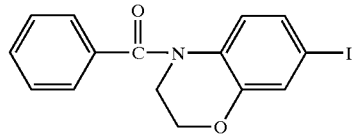

Example 21
Synthesis of Illustrative Compound 2-7

An illustrative compound (2-7) was obtained in the same manner as in Example 6 except that the illustrative compound (A-4) was changed into an illustrative compound (A-15) as described below. The yield rate thereof was 67%.
$[\alpha]_D^{25}$ −167° (c0.10, CHCl$_3$)

Results of identification by using $^1$H-NMR (CDCl$_3$) are shown below.

δ (TMS); 7.70 (d, 1H), 7.64 (d, 1H), 7.55 (d, 4H), 7.42–7.20 (m, 6H), 6.95 (d, 4H), 6.42 (d, 1H), 6.34 (d, 1H), 5.40–5.25 (m, 2H), 4.95 (t, 1H), 4.60 (d, 1H), 4.20–4.00 (m, 12H), 3.20–3.05 (m, 4H), 1.90–1.76 (m, 4H), 1.60–1.44 (m, 4H), 1.05–0.94 (m, 6H)

Compound (A-15)

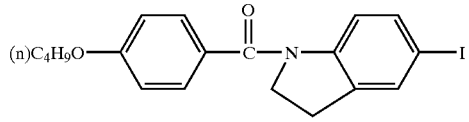

Example 22
Synthesis of Illustrative Compound 2-8

An illustrative compound (2-8) was obtained in the same manner as in Example 6 except that the illustrative compound (A-4) was changed into an illustrative compound (A-16) as described below. The yield rate thereof was 68%.
$[\alpha]_D^{25}$ −166° (c0.10, CHCl$_3$)

Results of identification by using $^1$H-NMR (CDCl$_3$) are shown below.

δ (TMS); 8.40–8.20 (m, 2H), 7.68 (d, 1H), 7.63 (d, 1H), 7.50–7.25 (m, 4H), 6.41 (d, 1H), 6.34 (d, 1H), 5.40–5.25 (m, 2H), 4.95 (t, 1H), 4.60 (d, 1H), 4.30–3.90 (m, 8H), 3.25–3.10 (m, 4H), 2.58–2.40 (m, 2H), 2.00–1.20 (m, 20H)

Compound (A-16)

Example 23
Synthesis of Illustrative Compound 2-20

An illustrative compound (2-20) was obtained in the same manner as in Example 6 except that the illustrative compound (A-4) was changed into an illustrative compound (A-17) as described below. The yield rate thereof was 20%.
$[\alpha]_D^{25}$ −260° (c0.10, CHCl$_3$)

Results of identification by using $^1$H-NMR (CDCl$_3$) are shown below.

δ (TMS); 7.70–7.34 (m, 12H), 7.19–6.80 (m, 6H), 6.45–6.25 (m, 2H), 5.40–5.21 (m, 2H), 4.99–4.89 (m, 1H), 4.62–4.55 (m, 1H), 4.45–4.30 (m, 4H), 4.18–3.79 (m, 8H)

Compound (A-17)

Next, examples are given below to illustrate applications of the optically active isosorbide derivative according to the invention and should not be interpreted as limiting the invention in any way.

Examples 24 to 42
Measurement of Change of Helical Pitch by Light Irradiation 19 types, as shown in Table 1, arbitrarily selected from among illustrative compounds of the optically active isosorbide derivatives (photo-reactive chiral agents) as represented by the general formula (I) were each added to a nematic liquid crystal composition (trade name: ZLI-1132;

available from Merck Corp.) in a quantity as described in Table 1 and, then, each of the resultant mixtures was poured into a wedge type cell (glass thickness: 1.1 mm; blue plate) which has been subjected to a uniaxial orientation treatment by using a polyimide orientation film. A helical pitch of the mixture was measured at room temperature by using a polarization microscope and, then, the thus-measured helical pitch was converted into a helical twisting power (HTP) which was, then, denoted as an initial HTP. Data of such initial HTP's are shown in Table 1.

Next, an ultraviolet ray having an irradiation intensity of 300 mW/cm$^2$ was irradiated on the wedge type cell from a high pressure mercury lamp for 3 minutes. After such irradiation, a helical pitch of the mixture was measured at room temperature in the same manner as described above and, then, the thus-measured helical pitch was converted into an HTP. Thereafter, a change ratio of the thus-converted HTP against the initial HTP was determined. Data of such change ratios of the HTP's are also shown in Table 1.

TABLE 1

| Compound No | Addition quantity (%) | Initial HTP ($\mu m^{-1}$) | HTP after light irradiation ($\mu m^{-1}$) | HTP Change ratio |
| --- | --- | --- | --- | --- |
| 1-2 | 1.0 | 49 | 5.5 | 8.9 |
| 1-7 | 1.0 | 42 | 8.0 | 5.3 |
| 1-8 | 1.0 | 35 | 6.7 | 5.2 |
| 1-9 | 1.0 | 39 | 7.1 | 5.5 |
| 1-21 | 0.5 | 45 | 6.9 | 6.5 |
| 1-26 | 1.0 | 21 | 4.7 | 4.5 |
| 1-27 | 1.0 | 28 | 5.3 | 5.3 |
| 1-28 | 1.0 | 26 | 5.7 | 4.6 |
| 1-29 | 1.0 | 24 | 4.5 | 5.3 |
| 1-30 | 1.0 | 24 | 3.8 | 6.3 |
| 1-32 | 1.0 | 26 | 3.7 | 7.0 |
| 2-2 | 1.0 | 46 | 7.4 | 6.2 |
| 2-4 | 1.0 | 45 | 7.5 | 6.0 |
| 2-5 | 1.0 | 43 | 6.0 | 7.2 |
| 2-6 | 1.0 | 34 | 8.4 | 4.0 |
| 2-7 | 1.0 | 39 | 5.9 | 6.6 |
| 2-8 | 1.0 | 46 | 11 | 4.2 |
| 2-17 | 1.0 | 36 | 5.0 | 7.2 |
| 2-20 | 1.0 | 56 | 22 | 2.5 |

As is apparent from Table 1, the helical twisting power (HTP) was able to be substantially changed by the ultraviolet ray irradiation. Further, when twisting directions before and after the ultraviolet ray irradiation were confirmed, it was found that they were both rightward.

Examples 43 to 50 and Comparative Examples 1 and 2

Change of Helical Pitch by Light Irradiation

In regard to each of 7 types of illustrative compounds of the optically active isosorbide derivatives and 2 types of compounds of Comparative Examples as shown below, a helical pitch change thereof caused by light irradiation was measured in the same manner as described above except that a method of light irradiation was changed into that of irradiation for 10 seconds by an transilluminator (available from Upland; 4.8 mW/cm$^2$) having a center wavelength of the light source near 370 nm. The results are shown in Table 2. It was found that the optically active isosorbide derivative according to the invention was highly sensible to light having the wavelength near 370 nm.

Further, a sample in which the helical pitch had thus been changed was held on a hot plate at 140° C. for 5 minutes and, then, the helical pitch was measured. The results are shown in Table 2. It was found that the optically active isosorbide derivative according to the invention was high in thermal stability.

Comparative Example 1

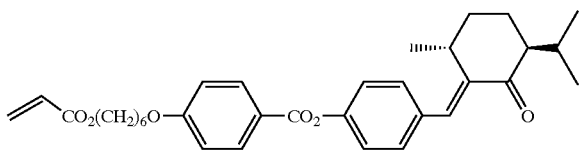

Comparative Example 2

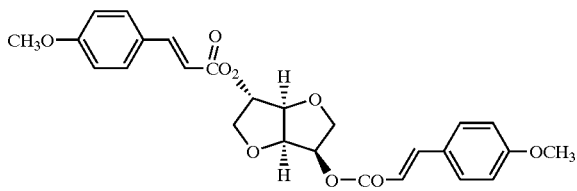

TABLE 2

| Compound No | Addition quantity (%) | Initial HTP ($\mu m^{-1}$) | HTP after light irradiation ($\mu m^{-1}$) | HTP change ratio | HTP after heating ($\mu m^{-1}$) |
| --- | --- | --- | --- | --- | --- |
| 1-21 | 0.5 | 45 | 20 | 2.3 | 20 |
| 1-26 | 1.0 | 21 | 8.4 | 2.5 | 8.4 |
| 1-27 | 1.0 | 28 | 7.7 | 3.6 | 7.7 |
| 1-32 | 1.0 | 25 | 7.0 | 3.6 | 7.0 |
| 2-4 | 1.0 | 45 | 18 | 2.5 | 18 |
| 2-5 | 1.0 | 43 | 14 | 3.1 | 14 |
| 2-8 | 1.0 | 46 | 17 | 2.7 | 17 |
| Comparative Example 1 | 1.0 | 23 | 20 | 1.2 | 20 |
| Comparative Example 2 | 1.0 | 44 | 43 | 1.0 | 43 |

Example 51

Production of Wide Band Circular Polarization Reflection Plate (1) Preparation of Substrate A coating solution for a polyimide orientation film (trade name: LX-1400, available from Hitachi Chemical DuPont Microsystems L.L.C.) was applied on a glass substrate by a spin coater and, then, dried for 5 minutes in an oven at 100° C. and, thereafter, baked for 1 hour in the oven at 250° C. to form an orientation film. Further, a surface of the thus-formed orientation film was subjected to an orientation treatment by means of a rubbing treatment to prepare a glass substrate provided with an orientation film thereon.

(2) Production

On the orientation film on the glass substrate provided with the orientation film thereon, a coating solution prepared in accordance with a prescription as described below was applied by a bar coater. After the resultant glass substrate was maintained on a hot plate at 110° C. for 5 minutes, it was irradiated for 1 minute at that temperature by light emitted from a super high pressure mercury lamp via a band pass filter having a center wavelength of the light source at 365 nm.

Next, the thus-irradiated glass substrate was kept for 5 minutes in a dark place with the temperature maintained at 110° C. Thereafter, the band pass filter was removed there-from and an entire surface thereof was further exposed to light having an irradiation energy of 500 mJ/cm$^2$ by using the same super high pressure mercury lamp as described above while blowing a nitrogen gas to perform polymerize-hardening. Accordingly, a circular polarization reflection plate was produced.

The thus-obtained circular polarization reflection plate has selective reflection in a wide wavelength region of 450 nm to 630 nm and a band characteristic sufficient for a wide band circular reflection plate. Further, the right circular polarization reflection ratio at a selective reflection wavelength of 550 nm was 98%.

[Prescription of Coating solution]

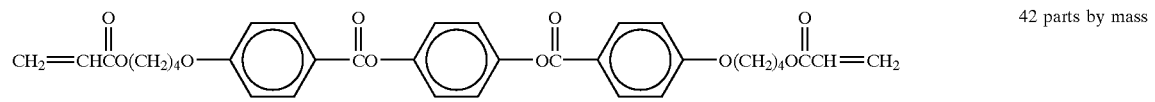

42 parts by mass

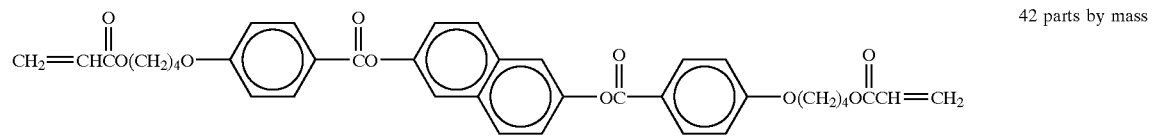

42 parts by mass

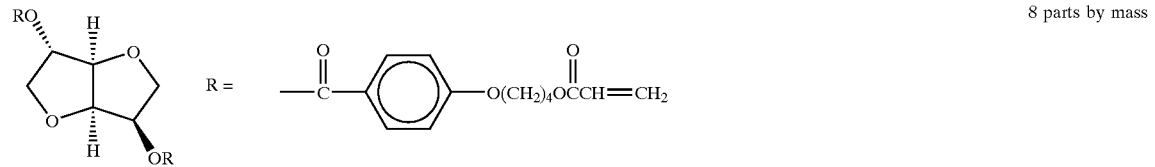

8 parts by mass

Illustrative compound 1-7

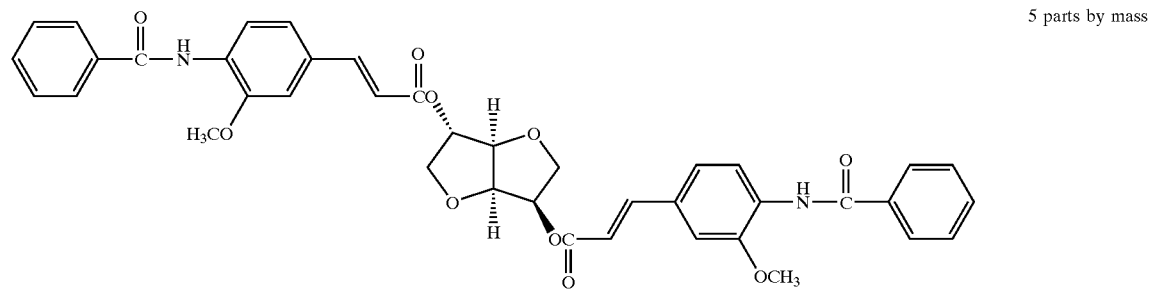

5 parts by mass

2 parts by mass

5 parts by mass

Chloroform 400 parts by mass

Example 52
Production of Liquid Crystal Color Filter
(1) Preparation of Filter Substrate A coating solution for a polyimide orientation film (trade name: LX-1400; available from Hitachi Chemical DuPont Microsystems L.L.C.) was applied on a glass substrate by a spin coater and dried for 5 minutes in an oven at 100° C. and, then, baked for 1 hour in the oven at 250° C. to form an orientation film. Further, a surface of the thus-formed orientation film was subjected to an orientation treatment by means of a rubbing treatment to prepare a glass substrate provided with an orientation film thereon.

(2) Formation of Filter Layer

On the orientation film on the thus-obtained glass substrate provided with the orientation film, a coating solution for a photosensitive resin layer prepared in accordance with a prescription as described below was applied by a spin coater and, then, dried in an oven at 110° C. for 2 minutes to form a photosensitive resin layer.

Next, the photosensitive resin layer was maintained at 110° C. for 5 minutes on a hot plate such that a surface of the glass substrate was allowed to be in contact with the hot plate, thereby forming color in the photosensitive resin layer. Further, a super high pressure mercury lamp was disposed above the photosensitive resin layer via a photo mask having three different types of transmittance (0%, 46%, 92%) which were aligned such that regions thereof were allowed to correspond to those for a blue pixel, a green pixel and a red pixel, respectively, and a band pass filter having a central wavelength at 365 nm whereupon light was irradiated through the photo mask and the band pass filter from the super high pressure mercury lamp to perform patterning. On this occasion, irradiation energy was 120 mJ/cm$^2$ for the red pixel and the irradiation intensity was 30 mW/cm$^2$.

Next, the photo mask and the band pass filter were removed and, instead, a sharp-cut filter allowing light of 400 nm or more to pass therethrough (light at 400 nm: 50%

(Prescription of Coating solution)

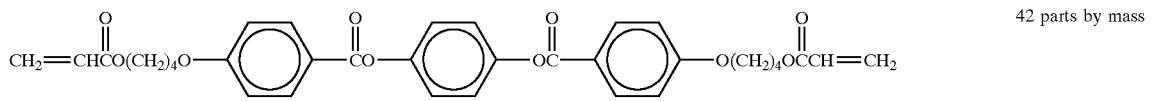

42 parts by mass

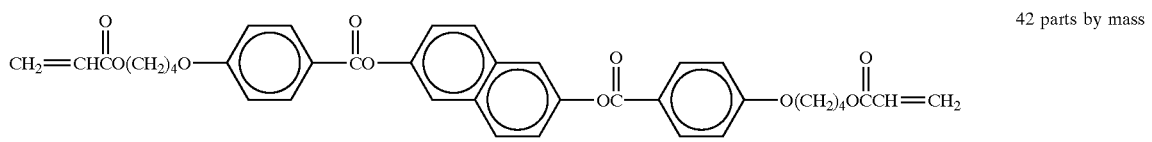

42 parts by mass

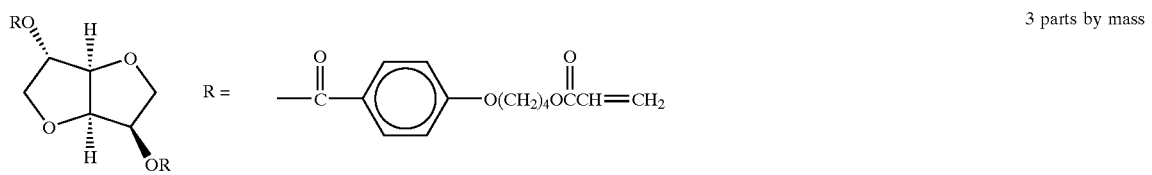

3 parts by mass

Illustrative compound 1-9

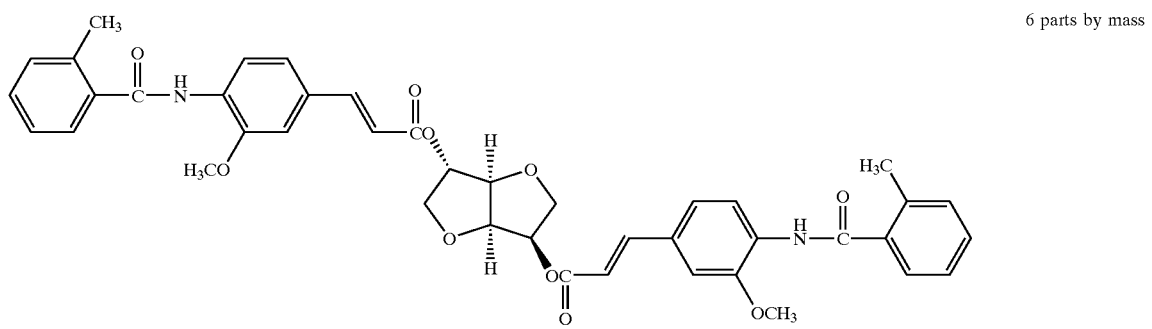

6 parts by mass

2 parts by mass

Dipentaerythritol hexaacrylate     3 parts by mass
Chloroform     400 parts by mass transmission) was provided and, then, an entire surface of the glass substrate was further exposed by light having an irradiation energy of 500 mJ/cm² by using the same super high pressure mercury lamp as described above while blowing a nitrogen gas for polymerize-hardening. Further, the glass substrate was baked for 20 minutes in an oven at 220° C. for promoting hardening of a filter portion (photosensitive resin layer) to obtain a color filter in which the red pixel, green pixel and blue pixel patterns were formed.

At the time of patterning, the liquid crystal helical pitch (liquid crystal helical twisting power) can significantly be changed by the irradiation whereupon pixel patterns comprising red, green and blue colors of high color purity were able to be formed.

spin coater and, then, dried for 5 minutes in an oven at 100° C. and, thereafter, baked for 1 hour in the oven at 250° C. to form an orientation film. Further, a surface of the thus-formed orientation film was subjected to an orientation treatment by means of a rubbing treatment to prepare a glass substrate provided with an orientation film thereon.

(2) Formation of Filter Layer

On the orientation film on the thus-obtained glass substrate provided with the orientation film thereon, a coating solution for a photosensitive resin layer prepared in accordance with a prescription as described below was applied by a spin coater and, then, dried in an oven at 110° C. for 2 minutes to form a photosensitive resin layer.

(Prescription of Coating solution)

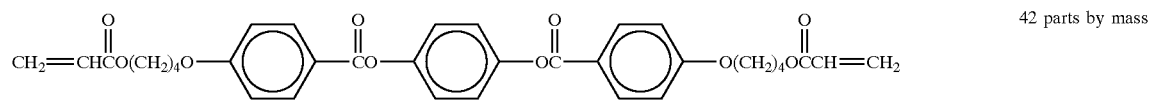

42 parts by mass

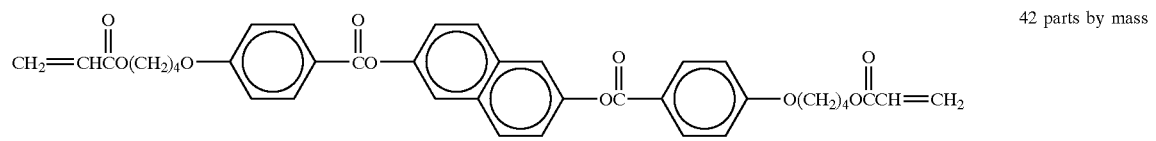

42 parts by mass

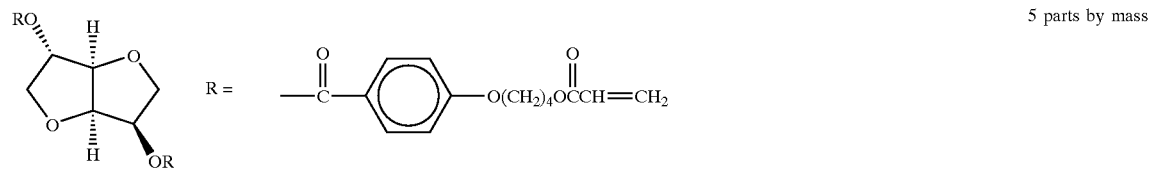

5 parts by mass

Illustrative Compound 1-27

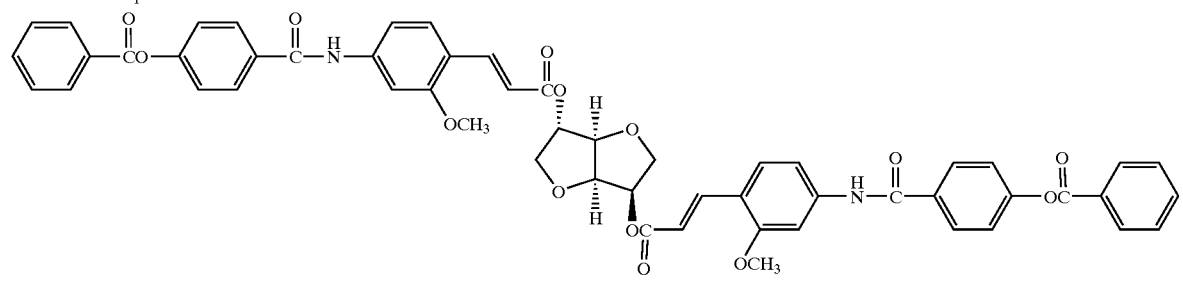

4 parts by mass 2 parts by mass

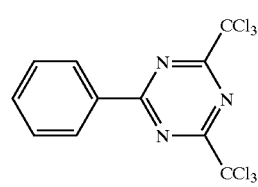

Dipentaerythritol hexaacrylate — 3 parts by mass
Chloroform — 400 parts by mass

Example 53
Production of Liquid Crystal Color Filter
(1) Preparation of Filter Substrate A coating solution for a polyimide orientation film (trade name: LX-1400; available from Hitachi Chemical DuPont Microsystems L.L.C.) was applied on a glass substrate by a Next, the photosensitive resin layer was maintained at 110° C. for 5 minute on a hot plate such that a surface of the glass substrate was allowed to be in contact with the hot plate, thereby forming color in the photosensitive resin layer. Further, a super high pressure mercury lamp was disposed above the photosensitive resin layer via a photo mask having three different types of transmittance (0%, 46%, 92%) which were aligned such that regions thereof were allowed to correspond to those for a blue pixel, a green pixel and a red pixel, respectively, and a band pass filter having a central wavelength at 365 nm whereupon light was irradiated through the photo mask and the band pass filter from the super high pressure mercury lamp to perform patterning. On this occasion, irradiation energy was 120 mJ/cm$^2$ for the red pixel and the irradiation intensity was 30 mW/cm$^2$.

Next, the photo mask and the band pass filter were removed and, then, an entire surface of the glass substrate was further exposed by light having an irradiation energy of 500 mJ/cm$^2$ by using the same super high pressure mercury lamp as described above while blowing a nitrogen gas for polymerize-hardening. Further, the glass substrate was baked for 20 minutes in an oven at 220° C. for promoting hardening of a filter portion (photosensitive resin layer) to obtain a color filter in which the red pixel, green pixel, and blue pixel patterns were formed.

At the time of patterning, the liquid crystal helical pitch (liquid crystal helical twisting power) can significantly be changed by the irradiation whereupon pixel patterns comprising red, green and blue colors of high color purity were able to be formed.

Example 54

Production of Liquid Crystal Color Filter (1) Preparation of Filter Substrate

A coating solution for a polyimide orientation film (trade name: LX-1400; available from Hitachi Chemical DuPont Microsystems L.L.C.) was applied on a glass substrate by a spin coater and, then, dried for 5 minutes in an oven at 100° C. and, thereafter, baked for 1 hour in the oven at 250° C. to form an orientation film. Further, a surface of the thus-formed orientation film was subjected to an orientation treatment by means of a rubbing treatment to prepare a glass substrate provided with an orientation film thereon.

(2) Formation of Filter Layer

On the orientation film on the thus-obtained glass substrate provided with the orientation film thereon, a coating solution for a photosensitive resin layer prepared in accordance with a prescription as described below was applied by a spin coater and, then, dried in an oven at 110° C. for 2 minutes to form a photosensitive resin layer.

(Prescription of Coating solution)

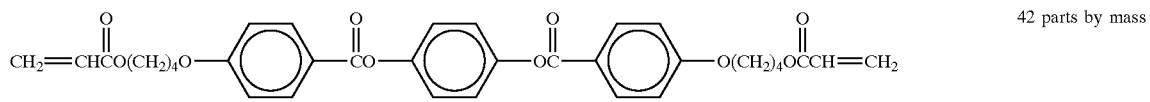

42 parts by mass

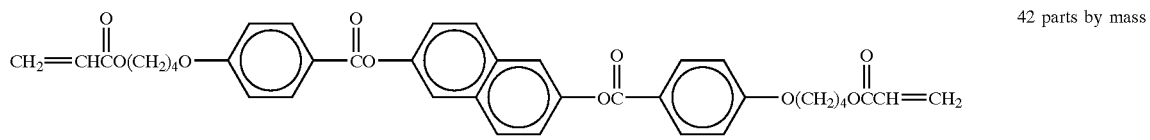

42 parts by mass

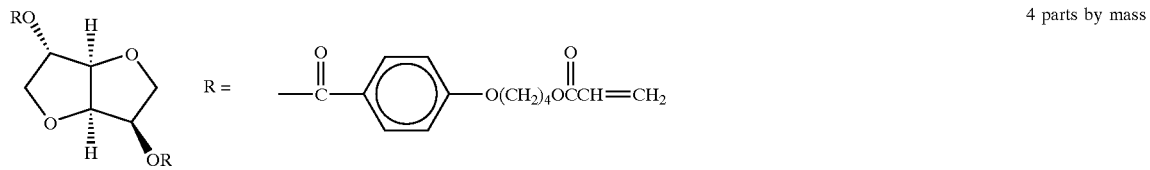

4 parts by mass

Illustrative compound 2-8

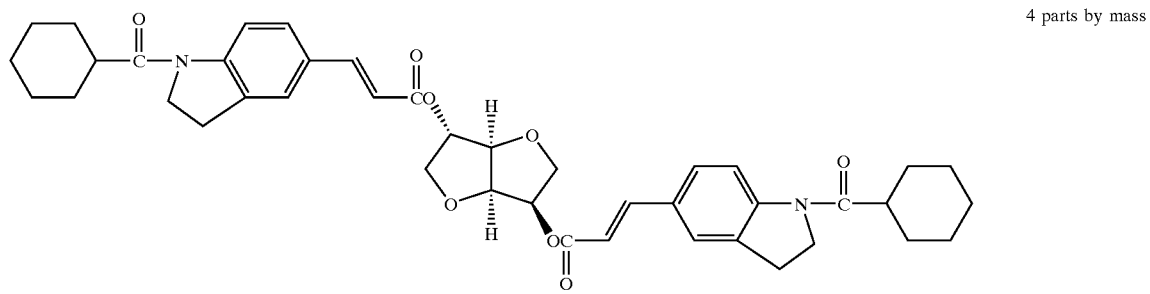

4 parts by mass

2 parts by mass

Dipentaerythritol hexaacrylate — 3 parts by mass
Chloroform — 400 parts by mass

Next, the photosensitive resin layer was maintained at 110° C. for 5 minute on a hot plate such that a surface of the glass substrate was allowed to be in contact with the hot plate to form color in the photosensitive resin layer. Further, a super high pressure mercury lamp was disposed above the photosensitive resin layer via a photo mask having three different types of transmittance (0%, 46%, 92%) which were aligned such that regions thereof were allowed to correspond to those for a blue pixel, a green pixel and a red pixel, respectively, and a band pass filter having a central wavelength at 365 nm whereupon light was irradiated through the photo mask and the band pass filter from the super high pressure mercury lamp to perform patterning. On this occasion, irradiation energy was 110 mJ/cm$^2$ for the red pixel and the irradiation intensity was 30 mW/cm$^2$.

Next, the photo mask and the band pass filter were removed and, then, an entire surface of the glass substrate was further exposed by light having an irradiation energy of 500 mJ/cm$^2$ by using the same super high pressure mercury lamp as described above while blowing a nitrogen gas for polymerize-hardening. Further, the glass substrate was baked for 20 minutes in an oven at 220° C. for promoting hardening of a filter portion (photosensitive resin layer) to obtain a color filter in which the red pixel, green pixel, and blue pixel patterns were formed.

At the time of patterning, the liquid crystal helical pitch (liquid crystal helical twisting power) can significantly be changed by the irradiation whereupon pixel patterns comprising red, green and blue colors of high color purity were able to be formed.

Example 55

Production of Optical Compensation Film for an STN Element

A polyvinyl alcohol (PVA) film having a saponification degree of 99.5% was formed on triacetyl cellulose (TAC) having a thickness of 80 μm by a bar coat method and heated for 3 minutes at 110° C. A surface of the thus-baked PVA film was subjected to a rubbing treatment and, then, a coating solution prepared in accordance with a prescription described below was applied thereon by a bar coater while heated and, thereafter, dried for 3 minutes in an oven at 120° C. to form a film.

(Prescription of Coating solution)

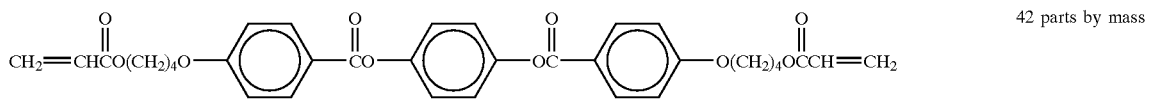 42 parts by mass

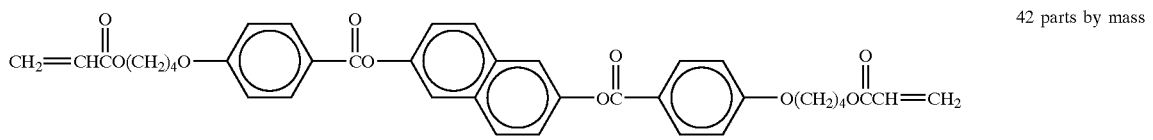 42 parts by mass

Illustrative compound 1-2

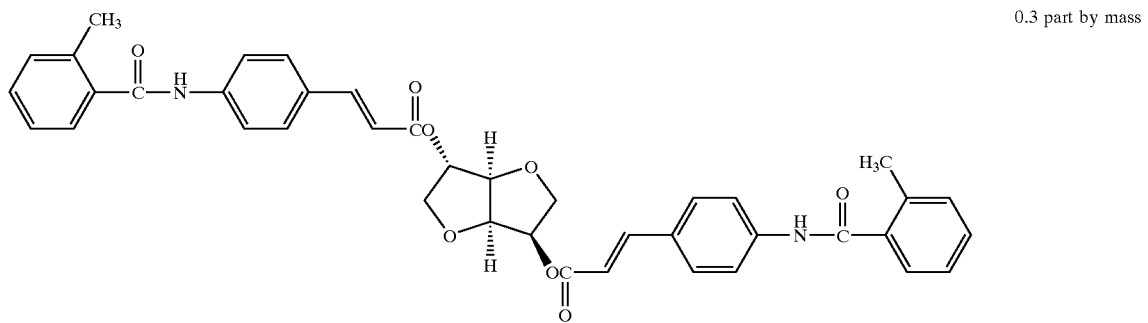 0.3 part by mass

 2 parts by mass

Chloroform  400 parts by mass

Next, the film was subjected to ultraviolet light irradiation (irradiation energy: 1000 mJ/cm$^2$) under a temperature of 100° C. using a super high pressure mercury lamp disposed above the film for polymerize-hardening to produce an optical compensation film for an STN element (hereinafter also referred to as "STN compensation film"). Film thickness of the STN compensation film measured on this occasion was 5.0 μm. Further, according to a polarized light transmission spectrum profile of the STN compensation film, it was found that the liquid crystal molecule orientation (helical structure) was twisted in a direction of film thickness by 240 degrees and the helical twist angle (rotation angle) was 240 degrees.

Still further, another STN compensation film having the twist angle opposite to the film (−240 degrees) was prepared. Both films were superimposed one on the other such that the liquid crystal molecules in respective portions which met with each other were disposed orthogonal to each other and were inserted between two polarizing plates whose absorption axes were orthogonal to each other and, then, were subjected to a visual observation to find that a favorable black color was exhibited. Therefore, it was confirmed that the film (STN compensation film) formed in a manner as described above functions as an optical compensation film for an STN element.

Example 56
Prevention of Generation of Reverse Twist Domain for TN Element

On an ITO film of a glass substrate provided with the ITO film, a coating solution for a polyimide orientation film (trade name: LX-1400; available from Hitachi Chemical DuPont Microsystems L.L.C.) was applied by a spin coater and, then, dried for 5 minutes in an oven at 100° C. and, thereafter, baked for 1 hour in the oven at 250° C. to form an orientation film. Further, a surface of the thus-baked film was subjected to an orientation treatment by means of a rubbing treatment such that a rubbing angle was allowed to be 90 degrees, thereby producing two glass substrates provided with respective orientation films.

The thus-produced glass substrates having respective orientation films were disposed such that such orientation films face to each other and bonded with each other by two-component epoxy resin adhesive mixed with spacer beads each having a diameter of 6 μm to form a drive cell. When thickness of the cell was measured by a light interference method, it was found to be 5.4 μm.

A composition comprising components described below was injected into the cell.

| Composition | |
|---|---|
| Nematic liquid crystal composition (trade name: ZLI-1132; available from Merck Corp.) | 99.9% |
| Photo-reactive chiral agent according to the invention (the illustrative compound 2-20) | 0.1% |

Next, the drive cell after being injected with the composition was inserted between two polarizing plates in which the absorption axes are disposed orthogonal to each other and, then, was subjected to a visual observation whereupon generation of a reverse twist domain was not observed. Therefore, an image display excellent in contrast and color purity without deteriorating the contrast due to the generation of the reverse twist can be expected.

Hereinafter, illustrative syntheses of the optically active isomannide derivative according to the invention are described and should not be interpreted as limiting the invention in any way. Unless otherwise stated, all parts and percentages (%) in examples are given by mass.

Example 57
Synthesis of Illustrative Compound (2'-8)

A mixture of 5.5 mmol (0.62 g) of a compound (B-1) as described below, 12.1 mmol (1.73 g) of an illustrative compound (B-2), 0.02 g of palladium acetate, 1.0 ml of triethyl amine and 10 ml of THF was stirred while heated for 3 hours, wherein an external temperature was 70° C. The resultant reaction product was cooled and, then, poured into diluted hydrogen chloride to generate a solid. The thus-generated solid was filtered to recover the solid. The thus-recovered solid was purified by a column chromatography to obtain 1.24 g of an illustrative compound (2'-8) which was a light yellow solid. The yield rate thereof was 73%.

$[\alpha]_D^{25}$ +322° (c0.10, CHCl$_3$)

Results of identification of the thus-obtained crystal by an analysis using $^1$H-NMR (CDCl$_3$) are shown below.

δ (in ppm from TMS); 8.35–5.18 (m, 2H), 7.70 (d, 2H), 7.40–7.36(m, 4H), 6.40 (d, 2H), 5.30–5.20 (m, 2H), 4.83–4.77 (m, 2H), 4.20–3.82 (m, 8H), 3.25–3.10 (m, 4H), 2.50–2.40 (m, 2H), 1.90–1.10 (m, 20H)

Compound (B-1)

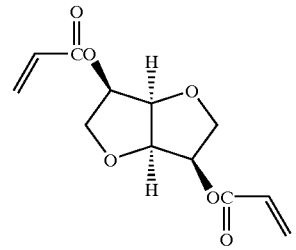

Next, examples are given below to illustrate applications of the optically active isomannide derivative according to the invention and should not be interpreted as limiting the invention in any way.

Example 58

Measurement of Change of Helical Pitch by Light Irradiation

The illustrative compound (2'-8) as synthesized above, as the optically active isomannide derivative (photo-reactive chiral agent) as represented by the general formula (V), was added to a nematic liquid crystal composition (trade name: ZLI-1132; available from Merck Corp.) in a quantity of 1.0% and, then, the resultant mixture was poured into a wedge type cell (glass thickness: 1.1 mm; blue plate) which has been subjected to a uniaxial orientation treatment by using a polyimide orientation film. A helical pitch of the mixture was measured at room temperature by using a polarization microscope and, then, the thus-measured helical pitch was converted into a helical twisting power (HTP) which was, then, denoted as an initial HTP. Data of such initial HTP's at 31 μm$^{-1}$ thereof were obtained.

Next, an ultraviolet ray having an irradiation intensity of 300 mW/cm$^2$ was irradiated on the wedge type cell from a high pressure mercury lamp for 3 minutes. After such irradiation, a helical pitch of the mixture was measured at room temperature in the same manner as described above and, then, the thus-measured helical pitch was converted into an HTP. HTP was 17 μm$^{-1}$ after the irradiation.

Calculated from a difference between the initial HTP and the HTP after the irradiation, a value of 1.8 was obtained as the HTP change ratio whereupon the helical twisting power (HTP) was allowed to be substantially changed by the ultraviolet ray irradiation. Further, when a twisting directions before and after the ultraviolet ray irradiation were confirmed, it was found that they were both leftward.

Example 59

Measurement of Change of Helical Pitch by Light Irradiation

In regard to the illustrative compound (2'-8) as the optically active isomannide derivative, a helical pitch change thereof caused by light irradiation was measured in the same manner as in Example 2 except that a method of light irradiation was changed into that of irradiation for 10 seconds by an transilluminator (available from Upland; 4.8 mW/cm$^2$) having a center wavelength of the light source near 370 nm. As a result, the initial HTP of 31 $\mu$m$^{-1}$, the HTP of 20 $\mu$m$^{-1}$ after the light irradiation and the HTP change ratio of 1.6 were obtained. It was found that the optically active isomannide derivative according to the invention is highly sensible to light at 370 nm and the vicinity thereof.

Example 60

Production of Wide Band Circular Polarization Reflection Plate (1) Preparation of Substrate A glass substrate provided with an orientation film thereon was prepared in accordance with Example 51(1).

(2) Production

A circular polarization reflection plate was produced in accordance with Example 51(2) except that the prescription of the coating solution was changed to that as described below.

---

(Prescription of Coating solution)

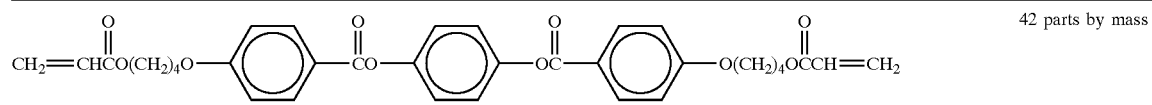

42 parts by mass

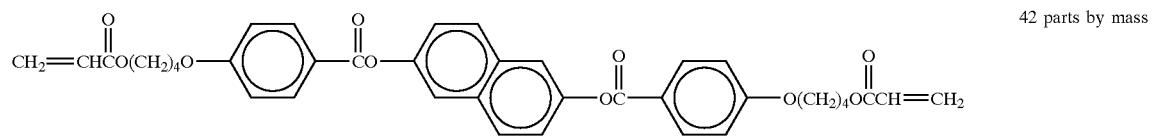

42 parts by mass

Illustrative compound 2'-8

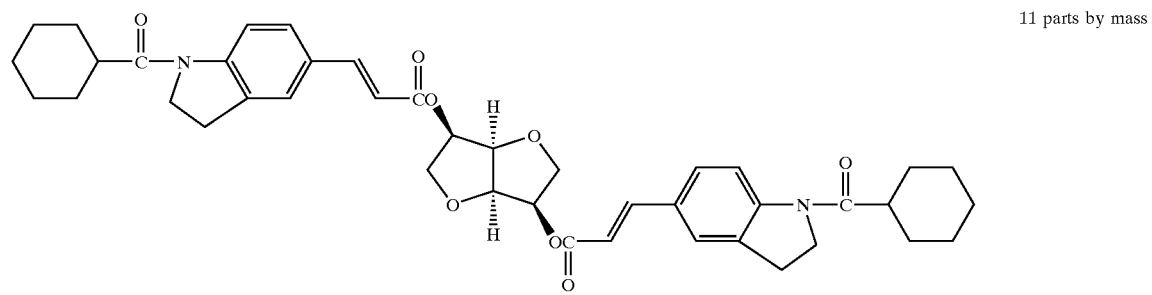

11 parts by mass

2 parts by mass

5 parts by mass

Chloroform 400 parts by mass

---

The thus-obtained circular polarization reflection plate showed a selective reflection in a wide wavelength region of 450 nm to 650 nm whereupon it had sufficient band characteristics as a wide band circular polarization reflection plate. Further, a leftward circular polarization reflectance at a selective reflection wavelength of 550 nm was 96%.

Example 61

Production of Liquid Crystal Color Filter (1) Preparation of Filter Substrate

A glass substrate provided with an orientation film thereon was prepared in accordance with Example 52(1).

(2) Formation of Filter Layer

A color filter was produced in accordance with Example 52(2) except that the prescription of the coating solution for the photosensitive resin layer was changed into that as described below.

twisting power) was allowed to be substantially changed by light irradiation, thereby forming pixel patterns comprising the red, green and blue colors of high color purity.

Example 62

Production of Optical Compensation Film for an STN Element

An optical compensation film for an STN element was produced in accordance with Example 55 except that the prescription of the coating solution was changed into that as described below.

(Prescription of Coating solution)

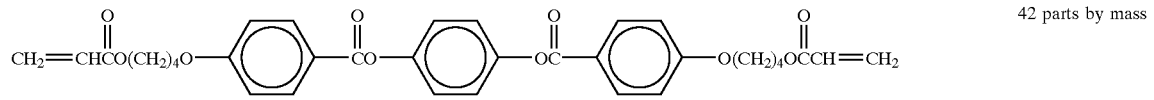
42 parts by mass

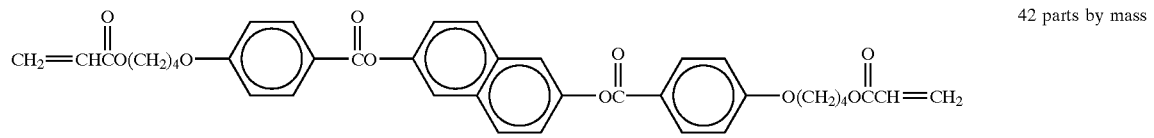
42 parts by mass

Illustrative compound 2'-8

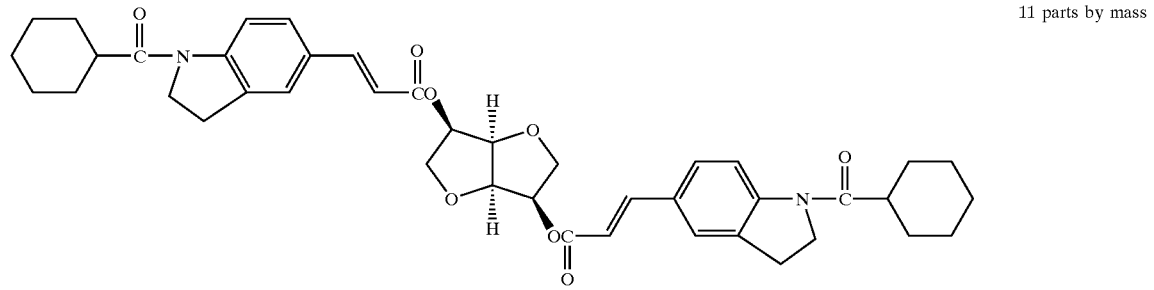
11 parts by mass

2 parts by mass

Dipentaerythritol hexaacrylate — 3 parts by mass
Chloroform — 400 parts by mass

At the time of performing the patterning (see Example 52(2)), the liquid crystal helical pitch (liquid crystal helical (Prescription of Coating solution)

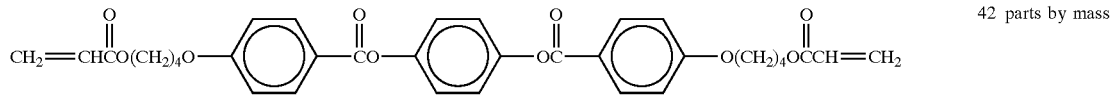
42 parts by mass

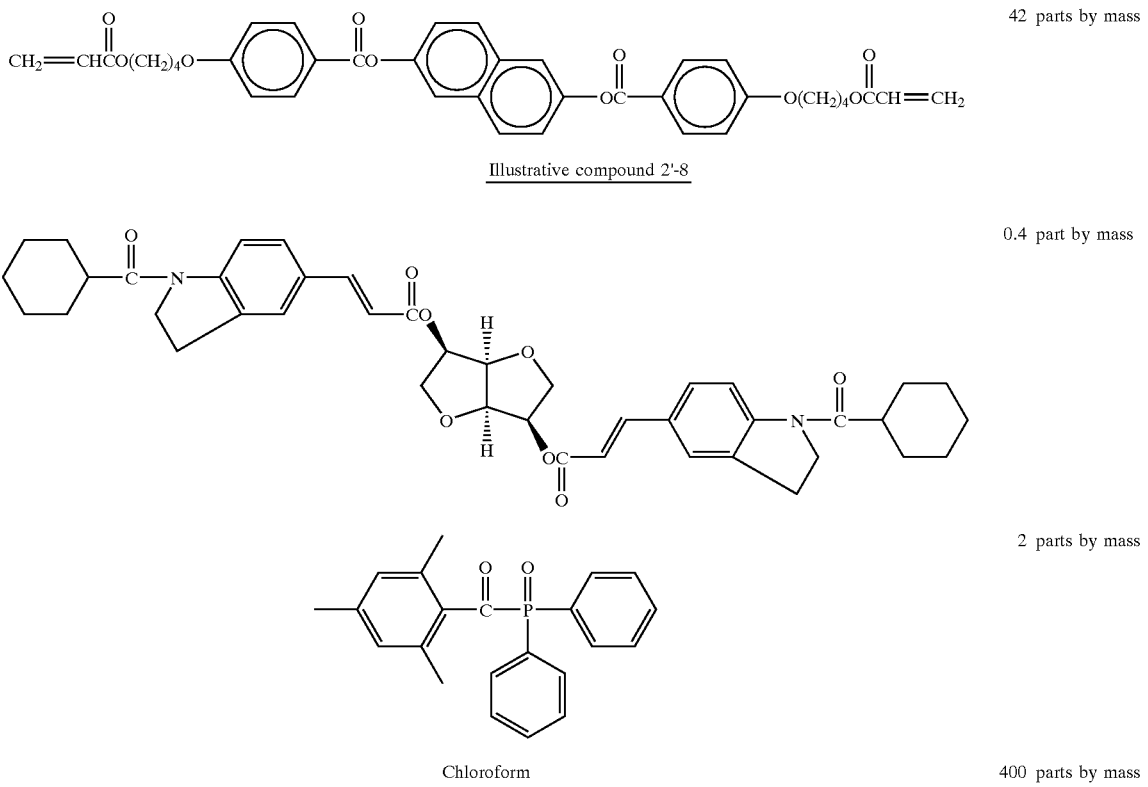

When film thickness of the STN compensation film was measured on this occasion, it was 5.0 μm. Further, according to a polarized light transmission spectrum profile of the STN compensation film, it was found that the liquid crystal molecule orientation (helical structure) was twisted in a direction of film thickness by −240 degrees and the helical twist angle (rotation angle) thereof was −240 degrees.

Still further, another STN compensation film having the twist angle (+240 degrees) opposite to the film was prepared. Both films were superimposed one on the other such that the liquid crystal molecules in respective portions which met with each other were disposed orthogonal to each other and were inserted between two polarizing plates whose absorption axes were orthogonal to each other and, then, were subjected to a visual observation to find that a favorable black color was exhibited. Therefore, it was confirmed that the film (STN compensation film) formed in a manner as described above functions as an optical compensation film for an STN element.

Example 63
Prevention of Generation of Reverse Twist Domain for TN Element

On an ITO film of a glass substrate provided with the ITO film, a coating solution for a polyimide orientation film (trade name: LX-1400; available from Hitachi Chemical DuPont Microsystems L.L.C.) was supplied by a spin coater and, then, dried for 5 minutes in an oven at 100° C. and, thereafter, baked for 1 hour in the oven at 250° C. to form an orientation film. Further, a surface of the thus-baked film was subjected to an orientation treatment by means of a rubbing treatment such that a rubbing angle was allowed to be 90 degrees, thereby producing two glass substrates provided with respective orientation films.

The thus-produced glass substrates having respective orientation films were disposed such that such orientation films face to each other and bonded with each other by two-component epoxy resin adhesive mixed with spacer beads each having a diameter of 6 μm to form a drive cell. When thickness of the cell was measured by a light interference method, it was found to be 5.4 μm.

A composition comprising components described below was injected into the cell.

| Composition | |
|---|---|
| Nematic liquid crystal composition (trade name: ZLI-1132; available from Merck Corp.) | 99.9% |
| Photo-reactive chiral agent according to the invention (the illustrative compound 2'-8) | 0.1% |

Next, the drive cell after being injected with the composition was inserted between two polarizing plates in which the absorption axes are disposed orthogonal to each other and, then, was subjected to a visual observation whereupon generation of a reverse twist domain was not observed. Therefore, an image display excellent in contrast and color purity without deteriorating the contrast due to the generation of the reverse twist can be expected.

According to the invention, there can be provided a novel optically active compound, having photosensitivity to light having a wavelength near 365 nm, which is capable of changing a structure thereof by being isomerized by light and, further, excellent in thermal stability of a cis-form to be generated after photo-isomerization is performed.

According to the invention, there can be provided a photo-reactive chiral agent which can control an orientation of a liquid crystalline compound, has a large change ratio of a helical pitch (helical twisting power) (hereinafter also referred to as "helical twisting change ratio") of liquid crystal by light, for example, in a case of using a nematic liquid crystal compound, can perform a wide selective reflection of colors comprising three primary colors (B, G, R) and can display three primary colors of high color purity.

According to the invention, there is provided a liquid crystal composition capable of changing a helical pitch (helical twisting power) of liquid crystal by light, and comprising a photo-reactive chiral agent which has a large helical twisting change ratio and can change optical properties by substantially controlling an orientation state of a liquid crystal molecule by light in a three-dimensional manner. For example, in a case of a cholesteric liquid crystal, there is provided the liquid crystal composition which shows a wide range of selectively reflected colors comprising three primary colors by light irradiation and is capable of displaying three primary colors excellent in color purity.

According to the invention, there is provided a method capable of substantially changing a helical pitch (helical twisting power) of liquid crystal by irradiating light on a liquid crystal composition comprising a photo-reactive chiral agent having a large helical twisting change ratio and capable of changing a helical structure of liquid crystal.

According to the invention, there is provided a method of fixing a helical structure of a liquid crystal, comprising the steps of:

exposing imagewise a liquid crystal composition containing a photo-reactive chiral agent having a large helical twisting change;

allowing the resultant patterned helical pitch to be fixed such that it is maintained without being damaged; and particularly in a case in which the liquid crystal phase is a cholesteric liquid crystal phase, fixing a helical structure of liquid crystal in a desired selectively reflected color to obtain a hue of high color purity.

According to the invention, there is provided a liquid crystal color filter of high color purity comprising a photo-reactive chiral agent which can substantially change a helical pitch (helical twisting power) of liquid crystal by light irradiation.

According to the invention, there is provided an optical film of non-light absorption type comprising a photo-reactive chiral agent which can substantially change a helical pitch (helical twisting power) of liquid crystal by light irradiation. Particularly in a case of a cholesteric liquid crystal phase, there is provided the optical film in which a selective reflection range is wide and color purity is high.

According to the invention, there is provided a recording medium comprising a photo-reactive chiral agent which can substantially change a helical twisting power of liquid crystal by light irradiation to form a sharp image by changing a light quantity imagewise. For example, when a liquid crystal phase is a cholesteric crystal liquid phase, there is provided the recording medium which can form an image which comprises selectively reflected colors having a wide hue range and high color purity.

What is claimed is:

1. An optically active isosorbide derivative represented by the following general formula (I):

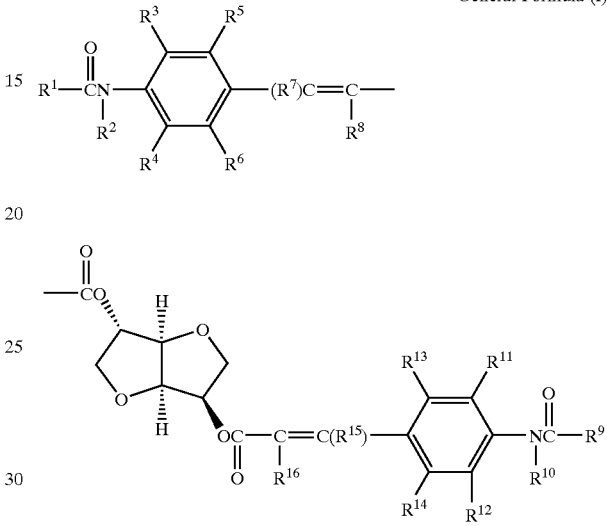

General Formula (I)

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

2. A method of producing an optically active isosorbide derivative represented by the following general formula (I), wherein aryl halides represented by the following general formulae (II) and (III) and an isosorbide derivative represented by the following general formula (IV) are made to react with each other:

General Formula (I)

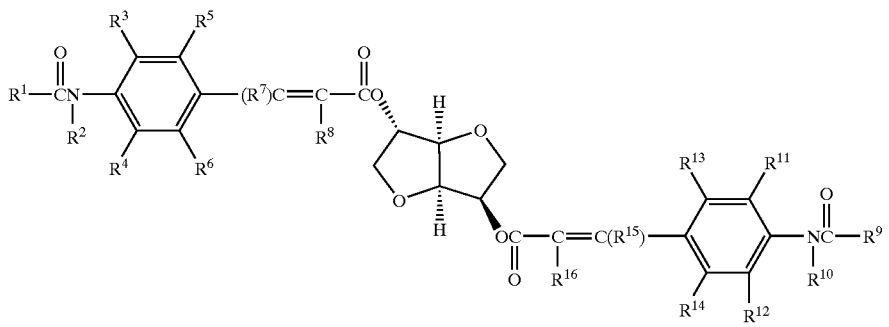

General formula (II)

General formula (III)

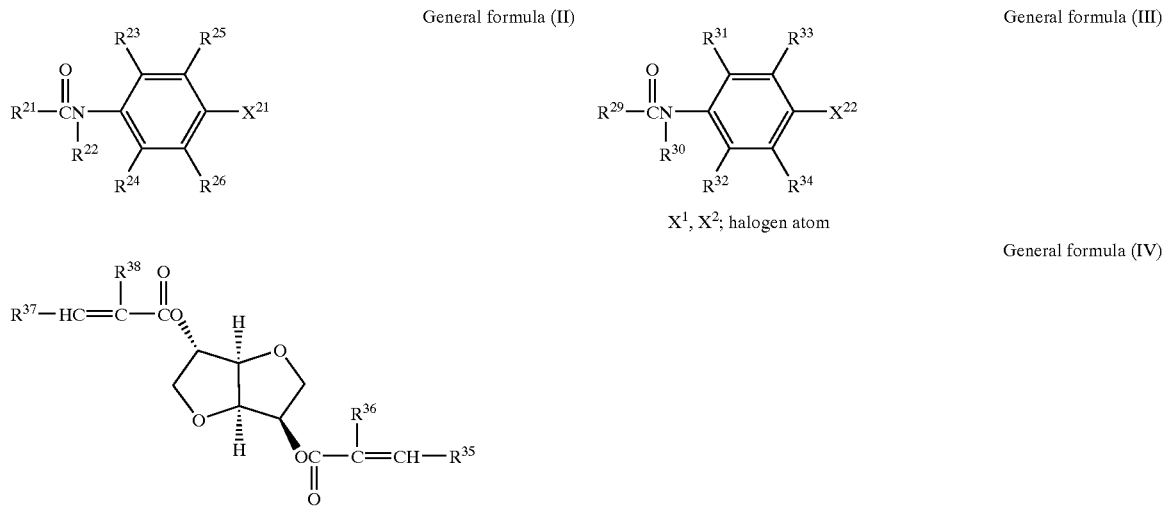

$X^1$, $X^2$; halogen atom

General formula (IV)

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group;

$R^2$ and $R^4$, and $R^{10}$ and $R^{12}$ may in each combination be combined with each other to form a 5- or 6-membered ring;

$R^{31}$ to $R^{46}$ each respectively and independently represent members that are equivalent to those represented by $R^1$ to $R^{16}$ in the general formula (I); and $X^{21}$ and $X^{22}$ each independently represent a halogen atom.

3. A photo-reactive chiral agent comprising an optically active isosorbide derivative represented by the following general formula (I)

General Formula (I)

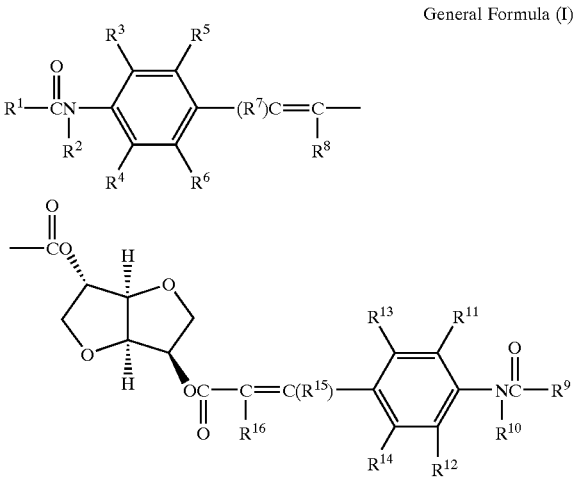

wherein $R^1$ and $R^9$ each independently represent a member selected from the group consisting of an alkyl group, an alkenyl group, an aryl group, a heterocyclic group, an alkoxy group, an aryloxy group and —$NR^{17}R^8$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

4. A liquid crystal composition comprising at least one liquid crystalline compound and at least one type of an optically active isosorbide derivative represented by the following general formula (I)

General Formula (I)

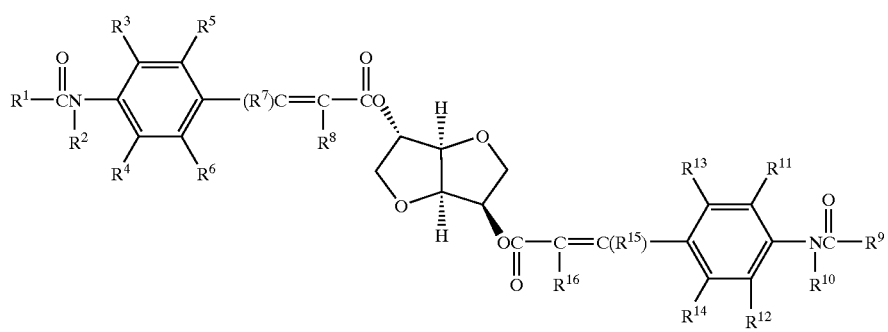

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

5. The liquid crystal composition according to claim 4, further comprising a photo-polymerization initiator, wherein the liquid crystalline compound has at least one polymerizable group.

6. The liquid crystal composition according to claim 5, wherein the optically active isosorbide derivative and the photo-polymerization initiator each have a different photo-sensitive wavelength region from each other.

7. A method for changing a helical structure of liquid crystal, wherein a structure of an optically active isosorbide derivative represented by the following general formula (I) is changed by irradiating light to a liquid crystal composition comprising at least one liquid crystalline compound and at least one type of the optically active isosorbide derivative represented by the following general formula (I)

General Formula (I)

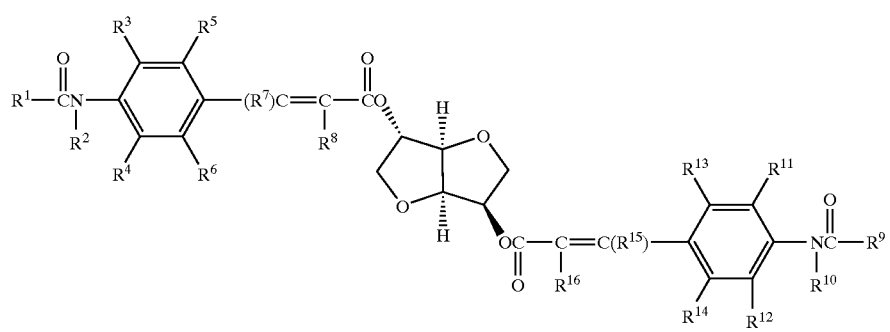

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

8. A method for fixing a helical structure of liquid crystal, the method comprising the steps of:

imagewise irradiating light having a wavelength within a photosensitive wavelength region of an optically active isosorbide derivative represented by the following general formula (I) to a liquid crystal comprising at least one liquid crystalline compound having at least one polymerizable group, at least one type of the optically active isosorbide derivative represented by the general formula (I), and a photo-polymerization initiator; and irradiating light having a wavelength region within a photosensitive wavelength region of the photo-polymerization initiator agent to the thus-irradiated liquid crystal composition to perform photo-polymerization General Formula (I)

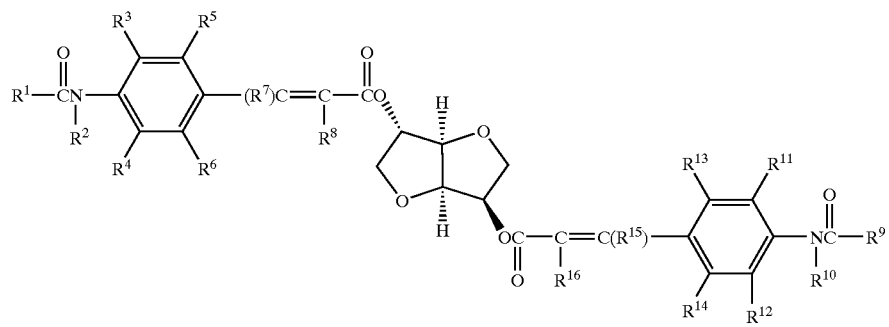

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

9. A liquid crystal color filter comprising at least one liquid crystalline compound and at least one type of an optically active isosorbide derivative represented by the following general formula (I)

General Formula (I)

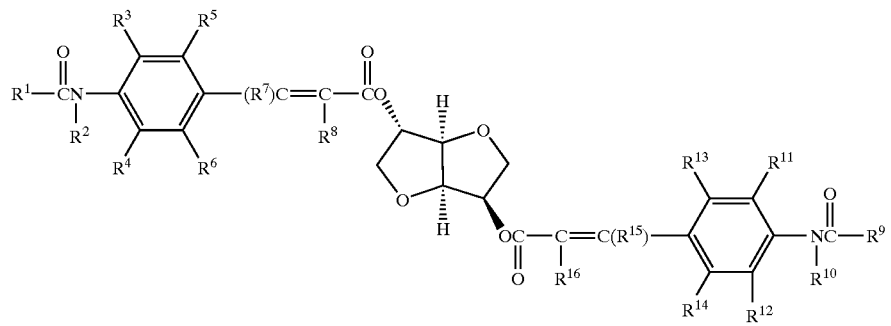

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

10. An optical film comprising at least one liquid crystalline compound and at least one type of an optically active isosorbide derivative represented by the following general formula (I)

General Formula (I)

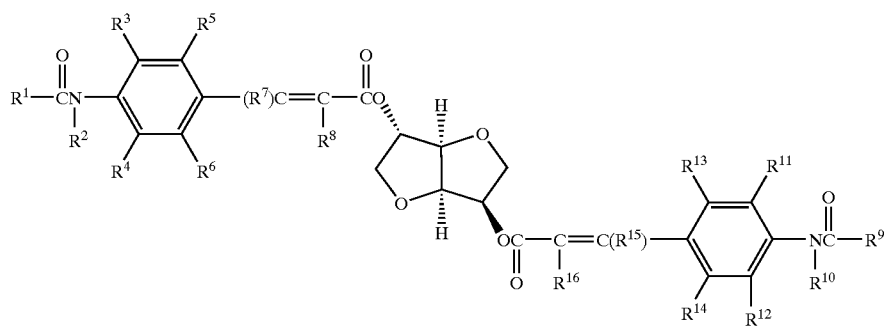

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

11. A recording medium comprising at least one liquid crystalline compound and at least one type of an optically active isosorbide derivative represented by the following general formula (I)

General Formula (I)

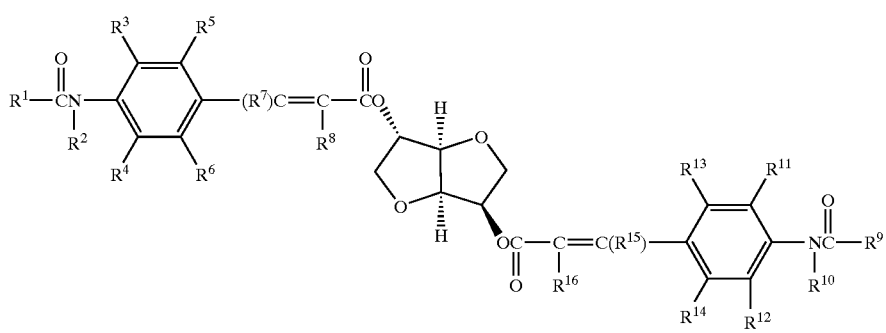

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

12. An optically active isomannide derivative represented by the following general formula (V):

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

General Formula (V)

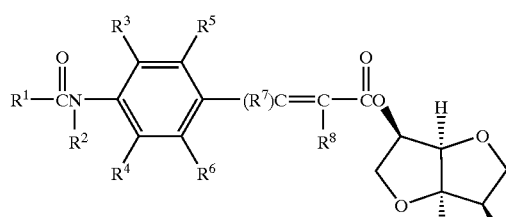
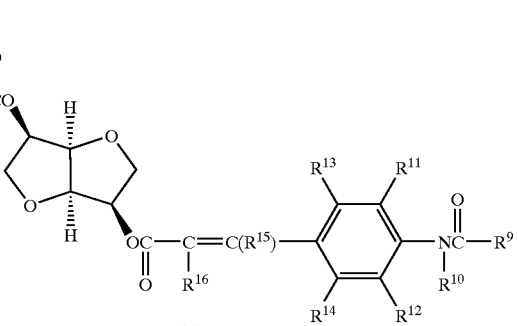

wherein $R^1$ and $R^9$ each independently represent a member selected from the group consisting of an alkyl group, an alkenyl group, an aryl group, a heterocyclic group, an alkoxy group, an aryloxy group and $-NR^{17}R^8$, wherein $R^{17}$ and $R^{18}$ each independently represent a member selected from the group consisting of a hydrogen atom, an alkyl group and an aryl group;

13. A method of producing an optically active isomannide derivative represented by the following general formula (V), wherein aryl halides represented by the following general formulae (II) and (III) and an isomannide derivative represented by the following general formula (VI) are made to react with each other:

General Formula (V)

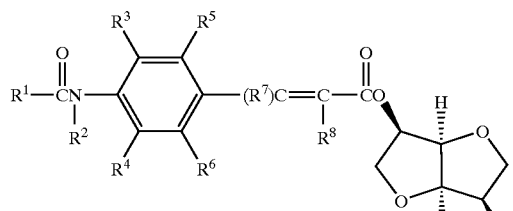
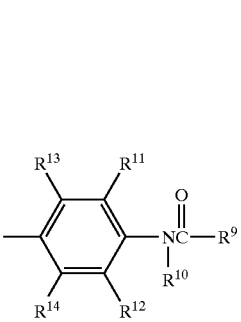

General formula (II)

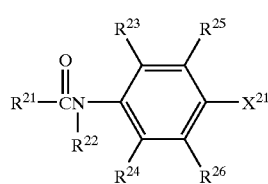

General formula (III)

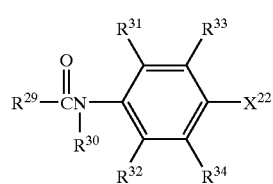

$X^1$, $X^2$; halogen atom

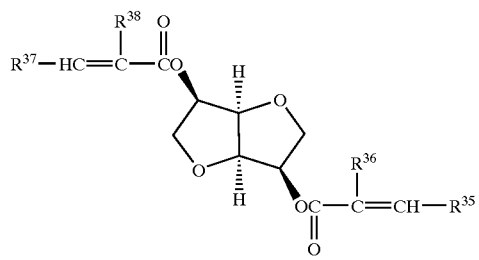

General formula (VI)

wherein $R^1$ and $R^9$ each independently represent a member selected from the group consisting of an alkyl group, an alkenyl group, an aryl group, a heterocyclic group, an alkoxy group, an aryloxy group and $-NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group;

$R^2$ and $R^4$, and $R^{10}$ and $R^{12}$ may in each combination be combined with each other to form a 5- or 6-membered ring;

$R^{31}$ to $R^{46}$ respectively and independently represent members that are equivalent to those represented by $R^1$ to $R^{16}$ in the general formula (V); and $X^{21}$ and $X^{22}$ each independently represent a halogen atom.

14. A photo-reactive chiral agent comprising an optically active isomannide derivative represented by the following general formula (V)

wherein $R^1$ and $R^9$ each independently represent a member selected from the group consisting of an alkyl group, an alkenyl group, an aryl group, a heterocyclic group, an alkoxy group, an aryloxy group and $-NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

15. A liquid crystal composition comprising at least one liquid crystalline compound and at least one type of an optically active isomannide derivative represented by the following general formula (V)

General Formula (V)

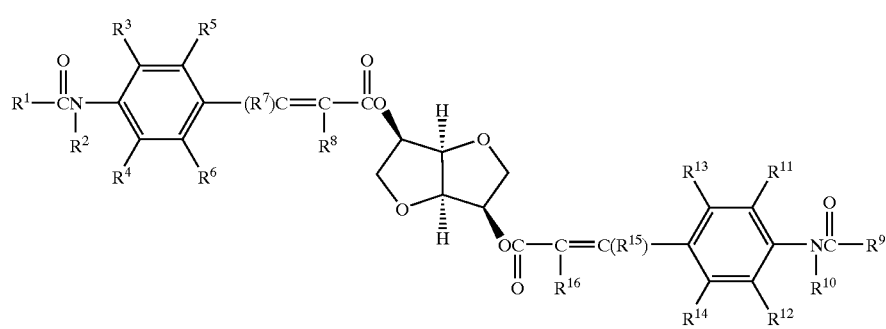

General Formula (V)

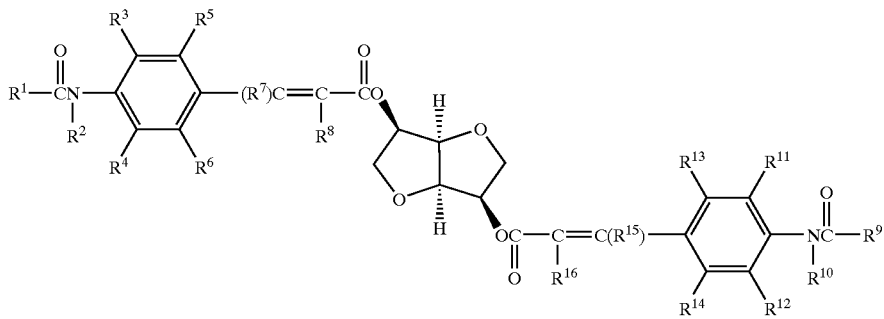

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

16. The liquid crystal composition according to claim 15 comprising a photo-polymerization initiator, wherein the liquid crystalline compound has at least one polymerizable group.

17. The liquid crystal composition according to claim 16, wherein the optically active isomannide derivative and the photo-polymerization initiator each have a different photosensitive wavelength region from each other.

18. A method for changing a helical structure of liquid crystal, wherein a structure of an optically active isomannide derivative represented by the following general formula (V) is changed by irradiating light to a liquid crystal composition comprising at least one liquid crystalline compound and at least one type of an optically active isosorbide derivative represented by the following general formula (V)

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

19. A method for fixing a helical structure of liquid crystal, the method comprising the steps of:

imagewise irradiating light having a wavelength within a photosensitive wavelength region of an optically active isomannide derivative represented by the following general formula (V) to a liquid crystal composition comprising at least one liquid crystalline compound having at least one polymerizable group, at least one type of the optically active isosorbide derivative represented by the general formula (V) and a photo-polymerization initiator; and irradiating light having a wavelength within a photosensitive wavelength region of the photo-polymerization initiator agent to the thus-irradiated liquid crystal composition to perform photo-polymerization General Formula (V)

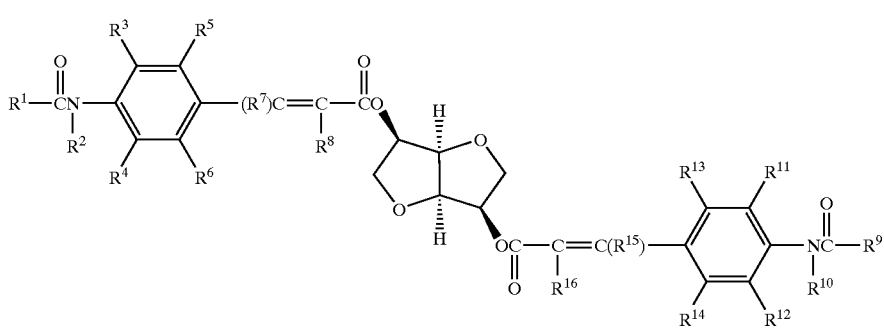

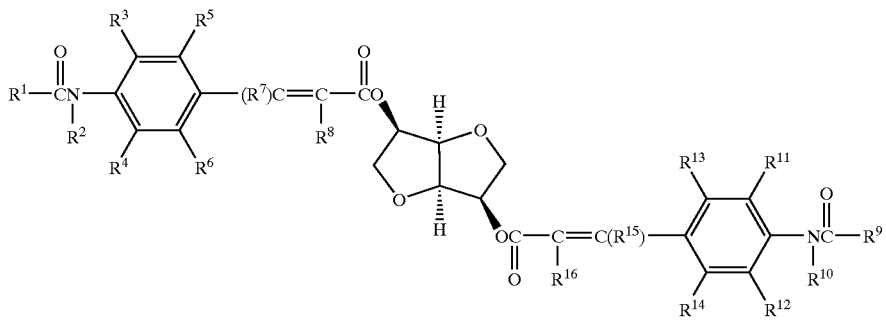

General Formula (V)

wherein $R^1$ and $R^9$ each independently represent a member selected from the group consisting of an alkyl group, an alkenyl group, an aryl group, a heterocyclic group, an alkoxy group, an aryloxy group and $-NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

20. A liquid crystal color filter comprising at least one liquid crystalline compound and at least one type of an optically active isomannide derivative represented by the following general formula (V)

wherein $R^1$ and $R^9$ each independently represent a member selected from the group consisting of an alkyl group, an alkenyl group, an aryl group, a heterocyclic group, an alkoxy group, an aryloxy group and $-NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

21. An optical film comprising at least one liquid crystalline compound and at least one type of an optically active isomannide derivative represented by the following general formula (V)

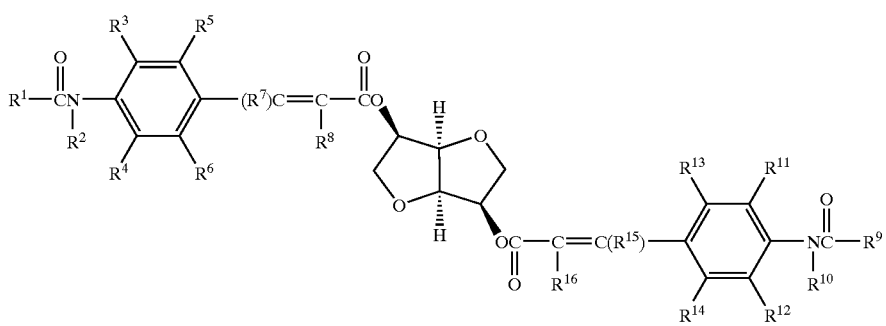

General Formula (V)

General Formula (V)

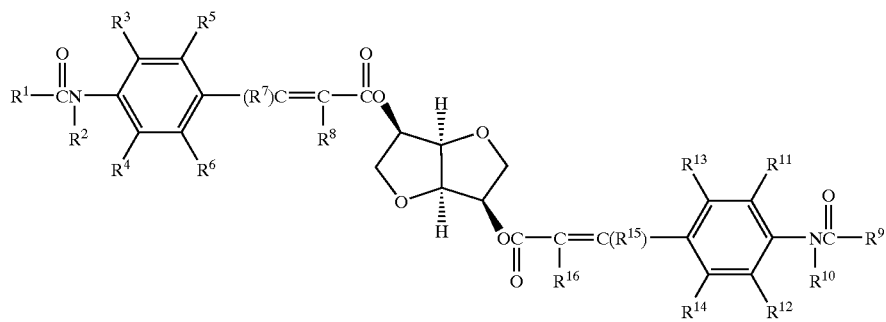

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

22. A recording medium comprising at least one liquid crystalline compound and at least one type of an optically active isomannide derivative represented by the following general formula (V)

General Formula (V)

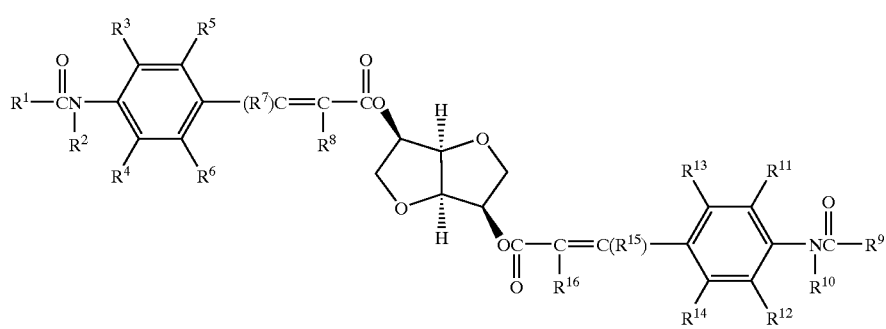

wherein $R^1$ and $R^9$ each independently represent a member selected from the group consisting of an alkyl group, an alkenyl group, an aryl group, a heterocyclic group, an alkoxy group, an aryloxy group and —$NR^{17}R^{18}$, wherein $R^{17}$ and $R^{18}$ each independently represent a member selected from the group consisting of a hydrogen atom, an alkyl group and an aryl group;

$R^2$ and $R^{10}$ each independently represent a member selected from the group consisting of a hydrogen atom, an alkyl group and an aryl group;

$R^3$ to $R^6$ and $R^{11}$ to $R^{14}$ each independently represent a member selected from the group consisting of a hydrogen atom, a halogen atom, an alkyl group and an alkoxy group;

$R^7$, $R^{15}$, $R^8$ and $R^{16}$ each independently represent a hydrogen atom or an alkyl group; and $R^2$ and $R^4$, and $R^{10}$ and $R^{12}$ may in each combination be combined with each other to form a 5- or 6-membered ring.

* * * * *